(12) United States Patent
Uvarkina et al.

(10) Patent No.: US 8,288,142 B2
(45) Date of Patent: Oct. 16, 2012

(54) HYALURONIDASE AND METHOD OF USE THEREOF

(76) Inventors: Tamara P. Uvarkina, Moscow (RU); Eugene G. Kahojan, Moscow (RU)

( * ) Notice: Subject to any disclaimer, the term of this patent is extended or adjusted under 35 U.S.C. 154(b) by 230 days.

(21) Appl. No.: 12/664,667

(22) PCT Filed: Jun. 19, 2008

(86) PCT No.: PCT/IB2008/002688
§ 371 (c)(1),
(2), (4) Date: Dec. 15, 2009

(87) PCT Pub. No.: WO2009/037566
PCT Pub. Date: Mar. 26, 2009

(65) Prior Publication Data
US 2010/0172892 A1    Jul. 8, 2010

Related U.S. Application Data

(60) Provisional application No. 60/945,037, filed on Jun. 19, 2007.

(51) Int. Cl.
*C12N 9/00* (2006.01)
*C12N 9/10* (2006.01)
*C12N 1/20* (2006.01)
*C12N 15/00* (2006.01)
*C07H 21/04* (2006.01)

(52) U.S. Cl. .................... 435/193; 435/183; 435/252.3; 435/320.1; 536/23.2

(58) Field of Classification Search ........................ None
See application file for complete search history.

(56) References Cited

OTHER PUBLICATIONS

SU 1723121. Jan. 19, 1990 (CAS Document No. 118:58232).*
Chica et al. Curr Opin Biotechnol. Aug. 2005;16(4):378-84.*
Sen et al. Appl Biochem Biotechnol. Dec. 2007;143(3):212-23.*

* cited by examiner

*Primary Examiner* — Christian Fronda
(74) *Attorney, Agent, or Firm* — Fish & Richardson P.C.

(57) ABSTRACT

The present invention provides a tnaluronidase. The hyaluronidase can be produced by the strain *Streptomyces* aitinocidm 77, Exemplary characteristics of the hyaluronidase include specific C-terminal or other amino acid sequences, including full-length sequences, and improved physicochemical and actix itj properties as compared to known h> aluronidase preparatkiiis. Described are also various uses of the hyaiurunidasc, including topical administration of the h> aiuronidasc to improve skin penetration of a co-administered active substance.

6 Claims, 16 Drawing Sheets

A                               B

1 - hexasaccharide    2 - terasaccharide

Figure 1A:
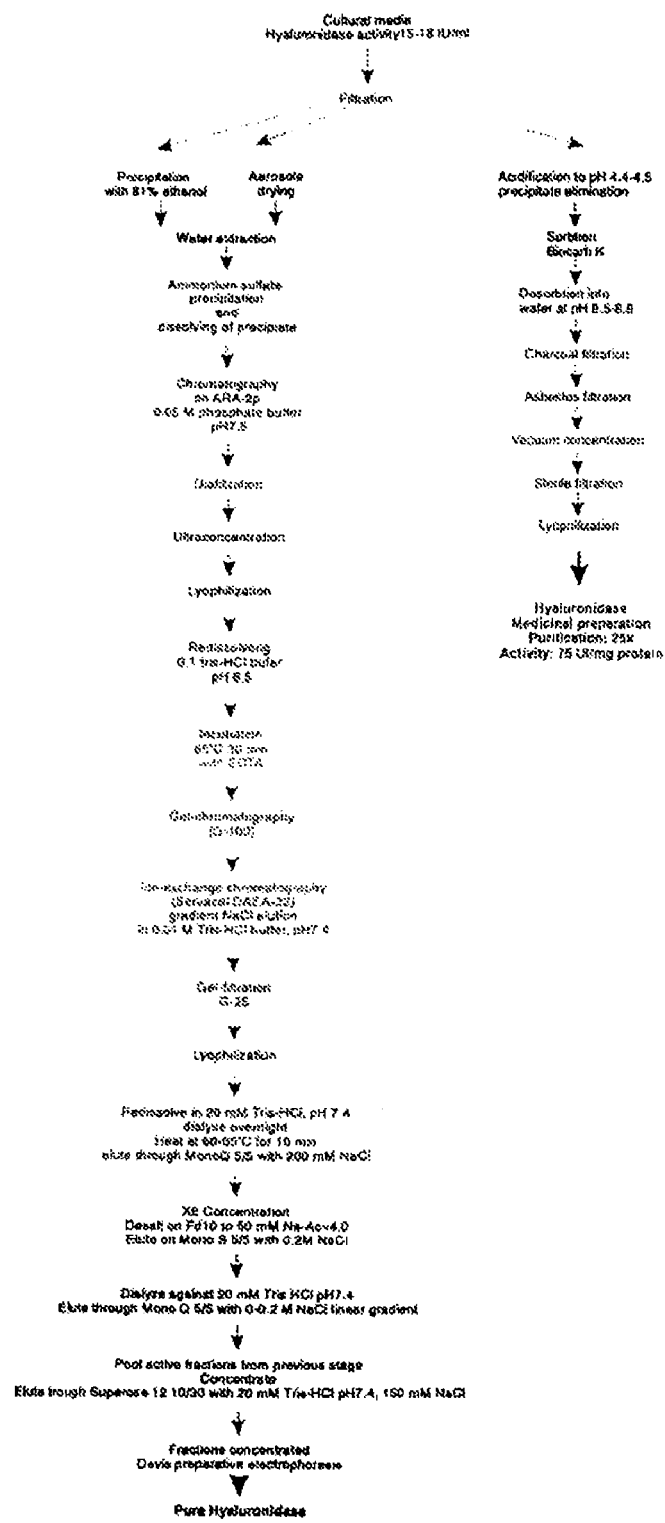

```
1    ggc gag tac acg ctc tac acs agc ccc gcs cag ttc taC GGC TCG TCG ACG
      G   E   Y   T   L   Y   T   S   P   A   Q   F   Y   G   S   S   T
52   ACG GCG CAC ACG GTC ACG ATC AAC CAC AAG GCT TCG TCC GGG GAC ACC GCG
      T   A   H   T   V   T   I   N   H   K   A   S   S   G   D   T   A
103  GCG CTG AAC GTC ACC TCG GAC AAC CCG GCC ACC TCG GCC ATG TAC CTG ACC
      A   L   N   V   T   S   D   N   P   A   T   S   A   M   Y   L   T
154  GGC GTG GAG ACC TCG CGC GGG ACG CTG AAG ATA TCC CAC AAG GGG TAC GCC
      G   V   E   T   S   R   G   T   L   K   I   S   H   K   G   Y   A
205  GAC GGT TCG GAC CCG GGG GCC TCC GGA CTC TCG ATC GAT CTC AGG ACC TCG
      D   G   S   D   P   G   A   S   G   L   S   I   D   L   R   T   S
256  ggg acc gcc gcg cag ggc atc ttc gtc acc gcg acc gac ggc ccg acc aag
      G   T   A   A   Q   G   I   F   V   T   A   T   D   G   P   T   K
307  GGA GCC CTG ATC GTC CTG CGG AAC AAC CCG GGC GTG GAC GAC TTC GTG GTC
      G   A   L   I   V   L   R   N   N   P   G   V   D   D   F   V   V
358  AAG GGC ACG GGC CGG ACG GGC ATC GGG ATC GGC CGC GGT GAC ACG CCC CAG
      K   G   T   G   R   T   G   I   G   I   G   R   G   D   T   P   Q
409  TCC CAG CTC CAC gtc gtc gcc gcs gcc ggc gcc ccs agc gc
      S   Q   L   H   V   V   A   A   A   G   A   P   S   A
```

Fig. 15

```
                        SEQUENCE LISTING

<160> NUMBER OF SEQ ID NOS: 9

<210> SEQ ID NO 1
<211> LENGTH: 15
<212> TYPE: PRT
<213> ORGANISM: Streptomyces actinocidus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Gly Asp Pro Xaa Asn Ser Leu Ser Pro Ala Leu Phe Tyr Gly Asp
1               5                   10                  15

<210> SEQ ID NO 2
<211> LENGTH: 15
<212> TYPE: PRT
<213> ORGANISM: Streptomyces actinocidus
<220> FEATURE:
<221> NAME/KEY: MISC_FEATURE
<222> LOCATION: (1)..(1)
<223> OTHER INFORMATION: Xaa is Asp or Gly

<400> SEQUENCE: 2

Xaa Asn Gly Glu Tyr Thr Leu Tyr Thr Ser Pro Ala Gln Phe Tyr
1               5                   10                  15

<210> SEQ ID NO 3
<211> LENGTH: 449
<212> TYPE: DNA
<213> ORGANISM: Streptomyces actinocidus

<400> SEQUENCE: 3
ggcgagtaca cgctctacac sagcccgcs cagttctacg gctcgtcgac gacggcgcac       60
acggtcacga tcaaccacaa ggcttcgtcc ggggacaccg cggcgctgaa cgtcacctcg      120
gacaacccgg ccacctcggc catgtacctg accggcgtgg agacctcgcg cgggacgctg      180
aagatatccc acaaggggta cgccgacggt tcggacccgg gggcctccgg actctcgatc      240
gatctcagga cctcggggac cgccgcgcag ggcatcttcg tcaccgcgac cgacggcccg      300
accaagggag ccctgatcgt cctgcggaac aacccgggcg tggacgactt cgtggtcaag      360
ggcacgggcc ggacgggcat cgggatcggc cgcggtgaca cgccccagtc ccagctccac      420
gtcgtcgccg csgccggcgc cccsagcgc                                        449
```

<210> SEQ ID NO 4
<211> LENGTH: 150
<212> TYPE: PRT
<213> ORGANISM: Artificial Sequence
<220> FEATURE:
<223> OTHER INFORMATION: synthetic peptide

<400> SEQUENCE: 4

Gly Glu Tyr Thr Leu Tyr Thr Ser Pro Ala Gln Phe Tyr Gly Ser Ser
1               5                   10                  15

Thr Thr Ala His Thr Val Thr Ile Asn His Lys Ala Ser Ser Gly Asp
            20                  25                  30

Thr Ala Ala Leu Asn Val Thr Ser Asp Asn Pro Ala Thr Ser Ala Met
        35                  40                  45

Tyr Leu Thr Gly Val Glu Thr Ser Arg Gly Thr Leu Lys Ile Ser His
    50                  55                  60

Lys Gly Tyr Ala Asp Gly Ser Asp Pro Gly Ala Ser Gly Leu Ser Ile
65                  70                  75                  80

Asp Leu Arg Thr Ser Gly Thr Ala Ala Gln Gly Ile Phe Val Thr Ala
                85                  90                  95

Thr Asp Gly Pro Thr Lys Gly Ala Leu Ile Val Leu Arg Asn Asn Pro
            100                 105                 110

Gly Val Asp Asp Phe Val Val Lys Gly Thr Gly Arg Thr Gly Ile Gly
        115                 120                 125

Ile Gly Arg Gly Asp Thr Pro Gln Ser Gln Leu His Val Val Ala Ala
    130                 135                 140

Ala Gly Ala Pro Ser Ala
145                 150

<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
ggcgagtaca csctctacac swssccsgcs cagttcta                             38

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
gtgsatctcs wwctcctcsg gsgtgtcgcc                                      30

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
satsatsgcs swsggsgcgc csgcsgcsgc sacsac                               36

<210> SEQ ID NO 8
<211> LENGTH: 24

-continued

```
<212> TYPE: DNA
<213> ORGANISM: Artificial Sequence
<220> FEATURE:
<223> OTHER INFORMATION: primer

<400> SEQUENCE: 8
gaasatgccc tgsgcsgcsg tgcc                                           24

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
cttsacsacg ccgtcsgtsg csgtsacgaa                                     30
```

HYALURONIDASE AND METHOD OF USE THEREOF

CROSS REFERENCE TO PRIOR APPLICATIONS

This is a U.S. National Phase application under 35 U.S.C. §371 of International Patent Application No. PCT/IB2008/002688, filed Jun. 19, 2008, and claims the benefit of U.S. Provisional Application No. 61/945,037, filed Jun. 19, 2007 both of which are incorporated by reference herein. The International Application published in English on Mar. 26, 2009 as WO 2009/037566 under PCT Article 21(2).

FIELD OF THE INVENTION

The present invention relates to a hyaluronidase. The invention also relates to methods of thing the hyaluronidase for modifying skin or connective tissue.

BACKGROUND OF THE INVENTION

The publications and reference materials noted herein are each incorporated by reference in their entirety.

The hyaluronidase enzyme family consists of enzymes capable of hydrolyzing or "breaking down" the polysaccharide hyaluronic acid. Hyaluronic acid is an important constituent of connective tissue. Thus, hyaluronidases, which can spread and diffuse rapidly through tissues, can modify the permeability and viscosity of the intercellular cement by hydrolyzing hyaluronic acid.

Hyaluronidases can be found in various animal tissues, e.g., mammalian testicular and spleen tissue, and in snake venom, and in certain species of *Streptococcus* and *Staphylococcus*. Basically, the enzyme family comprises three major groups: the testicular type (hyaluronoglucoronidase) (International Union of Biochemistry and Molecular Biology (IUMB) No. EC 3.2, 1.35); the leech type (hyaluronoglucoronidase) (IUMB EC. 3.2.1.36); and the bacterial type (hyaluronate lyase) (IUMB EC. 4.2.2.1). Between these groups, there are chemical and biological differences in, for example, substrate specificity, optimum pH, stability in aqueous and non-aqueous solutions, and thermal stability. For example, many bacterial hyaluronidases are only active towards hyaluronic acid or hyaluronate while testicular hyaluronidases hydrolyses both hyaluronic acid and other mucopolysaccharides (chondroitin, chondroitin sulfate). However, there are even greater variations within each group, in part related to the source of the enzyme.

Various hyaluronidases and methods for preparing and using them are known in the art (Linker A., Hyaluronidase. In: Methods of enzymatic analysis, Eds. Bergmeyer H U, Bergmeyer J, Grasl M, Verlag, Chemie Gmbh, Weinheim, 1984, pp. 256-262; King T P, Spar M D, Int Arch Allergy Immunol. 2000 October; 123(2):99-106; Jedrzejas M J, Crit. Rev Biochem Mol Biol, 2000; 35(3):221-51; Hynes W L, Walton S L, FEMS Microbiol Lett. 2000 Feb. 15; 183(2):201-7; Menzel E J, Farr C; Cancer Lett 1998; 131(1):3-11). For example, U.S. Pat. No. 4,258,134 relates to hyaluronidase from *Streptomyces koganeiensis*, having optimal activity at about pH 4.0; and Japanese Patent Nos. 63044883 and 62104579 provide hyaluronidase from *Streptococcus dysgalactiae*, the enzyme having a molecular weight of about 80 kD, and an optimum pH range of 5.8 to 6.6, which is inhibited by $Fe^{2+}$ and $Cu^{2+}$, Russian Federation Patent No. 2005488 describes a *Streptomyces actinocidus* hyaluronidase preparation termed Actinogial, which has a pH optimum of about 6.5 and a specific activity of about 30-40 IU/mg. Regarding hyaluronidase from non-bacterial origin, U.S. Pat. Nos. 4,904,594 and 5,061,627 relate to preparations of hyaluronidase from krill and other crustaceans; U.S. Pat. No. 5,593,877 is concerned with hyaluronidases and other proteins from vespid venom nucleic acids; U.S. Pat. Nos. 5,747,877 and 5,827,721 describe purified hyaluronidase of mammalian origin; and U.S. Pat. No. 5,854,046 and PCT publication WO 99/29841 are directed to human hyaluronidases.

Methods for producing and purifying hyaluronidases from various sources have been developed, as described in, e.g., U.S. Pat. No. 4,410,531, disclosing a method for purifying an enzyme from a crude hyaluronidase preparation: Swiss Patent No. CH628088, providing a method for purifying hyaluronate lyase and other proteins from Streptococci cultures; and U.S. Pat. No. 1,060,513, describing a method for preparing hyaluronidase from animal organs. See also SU1723121. U.S. Pat. No. 4,897,349 provides a method for increasing microbial biosynthesis of hyaluronidase by regulating oxygen concentration. Various types of hyaluronidase can be obtained commercially, e.g., from Wyeth-Ayerst (Wydase®), Abbot (Hyazyme), Bristol-Myers Squibb (Enzodase), and Pharmaceuticals (Diffusin).

One useful property of hyalurodinase is that it can reduce formation of scar tissue of varying etiologies and "soften" the skin. For example, methods for dissolving mammalian scar tissue by administering hyaluronidase and collagenase into the lesion are disclosed in U.S. Pat. Nos. 4,524,065 and 4,645,668; and methods for improving skin penetration of various topically applied drugs have been suggested by PCT publications WO 00/38732: WO 01/45743; and German Patent No. 19963538. Topically or parenteral administration of hyaluronidase can also be used to promote diffusion of substances, whether applied topically or injected. This has been applied clinically, where hyaluronidases have been used to facilitate the distribution of drugs or biological agents, usually in skin (Nara et al., Chem Pharm Bull (Tokyo) 1992; 40:737-40; Costello and Jeske, Phys Ther 1995; 75:554-63; Laugier, Br J Dermatol 2000 February; 142(2):226-33).

Hyaluronidases have also shown useful in a wide range of other medical applications, including blocking lymph node invasion of tumor cells (PCT publication WO 95/30439); treatments of vascular diseases (German Patent No. 19860541 and U.S. Pat. No. 4,568,543) and prostatic hypertrophy (U.S. Pat. No. 5,116,615); vaccination against helminth infection (U.S. Pat. No. 5,811,100); and for various opthalmologic applications (U.S. Pat. Nos. 5,292,509; 5,856,120; and 5,866,120). For example, hyaluronidase has been used to reduce intraocular pressure in the eyes of glaucoma patients through degradation of hyaluronan within the vitreous humor (U.S. Pat. No. 4,820,516).

Hyaluronidase has also been used in cancer therapy as a "spreading agent" to enhance the efficacy of chemotherapeutics and/or the accessibility of tumors to chemotherapeutics (Schuller et al., Proc. Amer. Assoc. Cancer Res. 1991; 32:173, abstract no. 1034; Czejka et al., Pharmazie 1990; 45:H.9) and has been used in combination with other chemotherapeutic agents in the treatment of a variety of cancers including urinary bladder cancer (Horn et al., 1985, J. Surg. Oncol., 2; 304-307), squamous cell carcinoma (Kohno et al., 94, J. Cancer Res. Oncol., 120:293-297), breast cancer (Beckenlehner et. al., 1992, J. Cancer Res. Oncol, 11.8:591-596), and gastrointestinal cancer (Scheithauer et al., 1988, Anticancer Res. 8:391-396). Administration of hyaluronidase also induces responsiveness of previously chemotherapy resistant tumors of the pancreas, stomach, colon, ovaries, and breast (Baumgartner et al., Reg. Cancer Treat. 1988; 1:55-58; canker et al., Proc. Amer, Assoc. Cancer Res. 1986; 27:390). In addition, serum hyaluronidase prevents growth of tumors transplanted into mice (De Macyer et al., Int. J. Cancer 1992; 51:657-660), while injection of hyaluronidase inhibits tumor formation caused by exposure to carcinogens (Pawlowsli et al., Int. J. Cancer 1979; 23:105-109; Haberman et al., Proceedings of the 17th Annual Meeting of the American Society of Clinical Oncology. Washington, D.C., 1981; 22:105, abstract no. 415). Intravenous or intramuscular injection of hyaluronidase is also effective in the treatment of brain cancer (gliomas) (PCT published application No. WO88/02261).

While there is a vast number of existing and potential therapeutic and cosmetic applications for hyaluronidase, a remaining problem is that currently available hyaluronidases are usually chemically and thermally unstable, often have significant non-specific activity, and show peak activity at an acidic pH, thus having suboptimal properties for in vivo applications. There is therefore a need in the art for hyaluronidase preparations that are stable in various formulations, and that show a high stability and activity at physiological temperatures and pH. The present invention addresses these and other needs in the art.

SUMMARY OF THE INVENTION

A hyaluronidase, isolated from a *Streptomyces actinocidus* strain, has been found to have important advantages over prior art hyaluronidases. The isolated enzyme of the invention preferably comprises a dialer of two symmetrical subunits, wherein the C-terminal sequence is GDPXNSLSPALFYGD (SEQ ID NO:1) or a function-conservative variant thereof. In one embodiment, the hyaluronidase also comprises the amino acid sequence (D/G)NGEYTLYTSPAQFY (SEQ ID NO:2) or a function-conservative variant thereof. The invention also provides for a hyaluronidase comprising the sequence of a full-length *Streptomyces actinocidus*.

Accordingly, the invention provides an isolated hyaluronidase comprising the sequence of SEQ. ID NO:1, and/or SEQ ID NO:2 and/or SEQ ID NO:4. In one embodiment, the hyaluronidase is a full-length, wild-type hyaluronidase comprising one or more physico-chemical, structural, functional, or immunological characteristics. In another embodiment, the hyaluronidase is variant of a full-length, wild-type enzyme, possessing one or more physico-chemical, structural, functional, or immunological characteristics of the full-length, wild-type enzyme, and comprising SEQ ID NO:1 or a function-conservative variant thereof, and/or SEQ NO:2 or a function-conservative variant thereof and/or SEQ ID NO:4 or a function-conservative, variant thereof.

The invention also provides compositions comprising the enzyme of the invention. Such compositions include, without limitation, formulations suitable for medical, pharmaceutical, and cosmetic applications. The compositions of the invention can also comprise one or more drugs, stabilizers, or excipients. Hydrocortisone and mannite (mannitol) are preferred, hut non-limiting, examples of drugs and stabilizers, respectively. Preferred formulations are those comprising suitable topical carriers for ointments, cosmetic creams, viscous formulations, or gels. Other preferred compositions include transdermal patches, bandages, pads, or tampons comprising the enzyme, with or without a drug.

In addition, the invention provides methods of using the enzyme of the invention for various cosmetic and medical purposes, including, without limitation, reduction and prevention of wrinkles and scars; enhancement of tissue or skin penetration of drugs; reduction of discomfort from rheumatoid arthritis, scleroderma, tendosynoviitis, or tendovaginitis; helping reduce chronic vaginal inflammation after surgical and non-surgical treatment; and as pre- or post-surgical treatment in conjunction with plastic surgery to improve the outcome.

The above features and many other attendant advantages of the invention will become better understood by reference to the following detailed description when taken in conjunction with the accompanying drawings.

BRIEF DESCRIPTION OF HE DRAWINGS

Figure 1B:
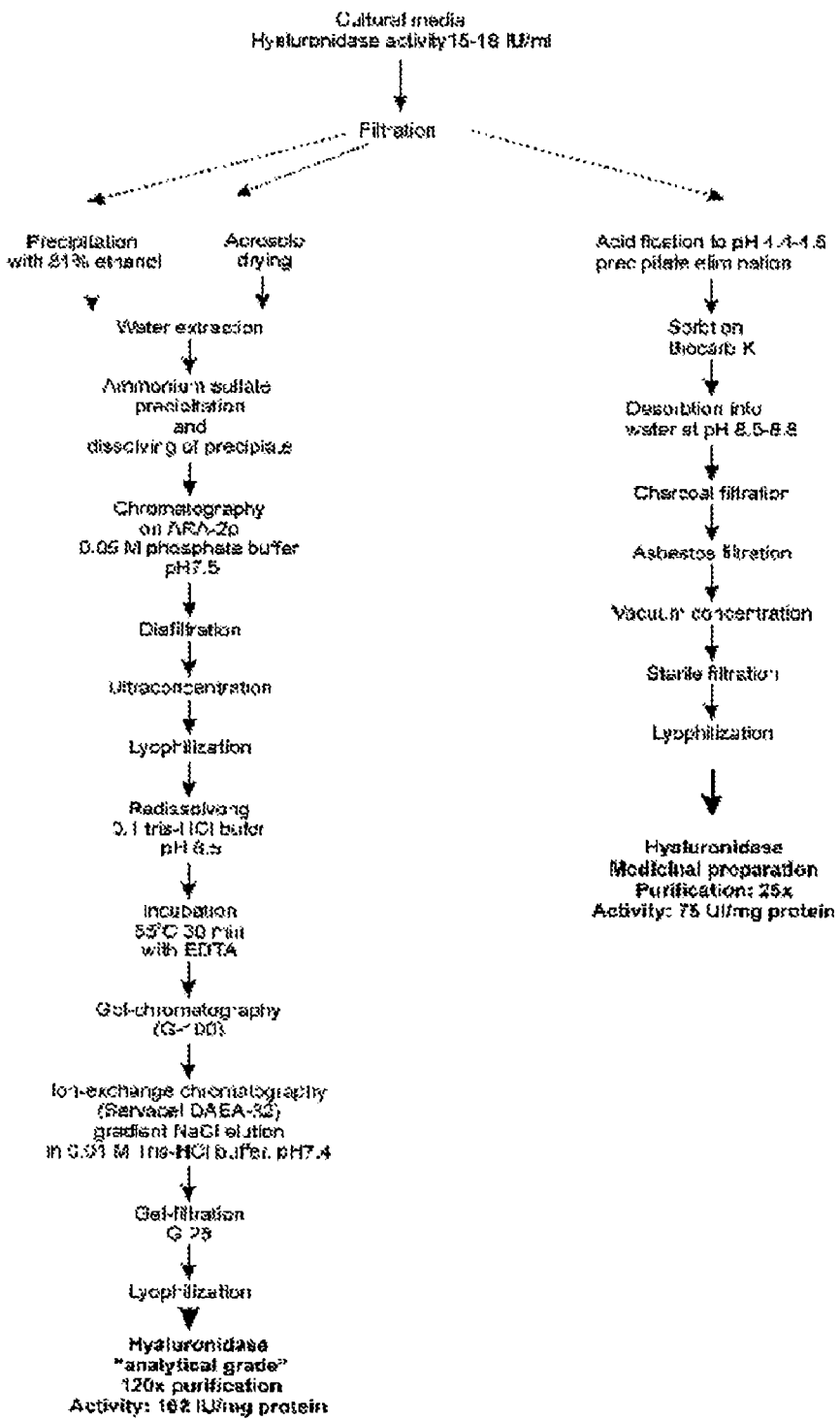

FIGS. 1A and 1B. Preparation of the hyaluronidase from *Streptomyces actinocidus* cultures. (A) This figure shows three different purification schemes for production of the microbial hyaluronidase of the invention. Precipitation in ethanol and aerosole drying followed by a series of chromatography and filtration steps yield preparations typically suitable for the preparation of pure enzyme for general experimental purposes, while acidification of the filtered culture medium followed by adsorption and filtration steps yields a preparation of the hyaluronidase suitable for medicinal applications. i.e., pharmaceutical preparations. (B) This figure shows an alternative purification route, which can lead to analytical grade hyaluronidase with an activity of about 162 IU per mg protein.

Figure 2:
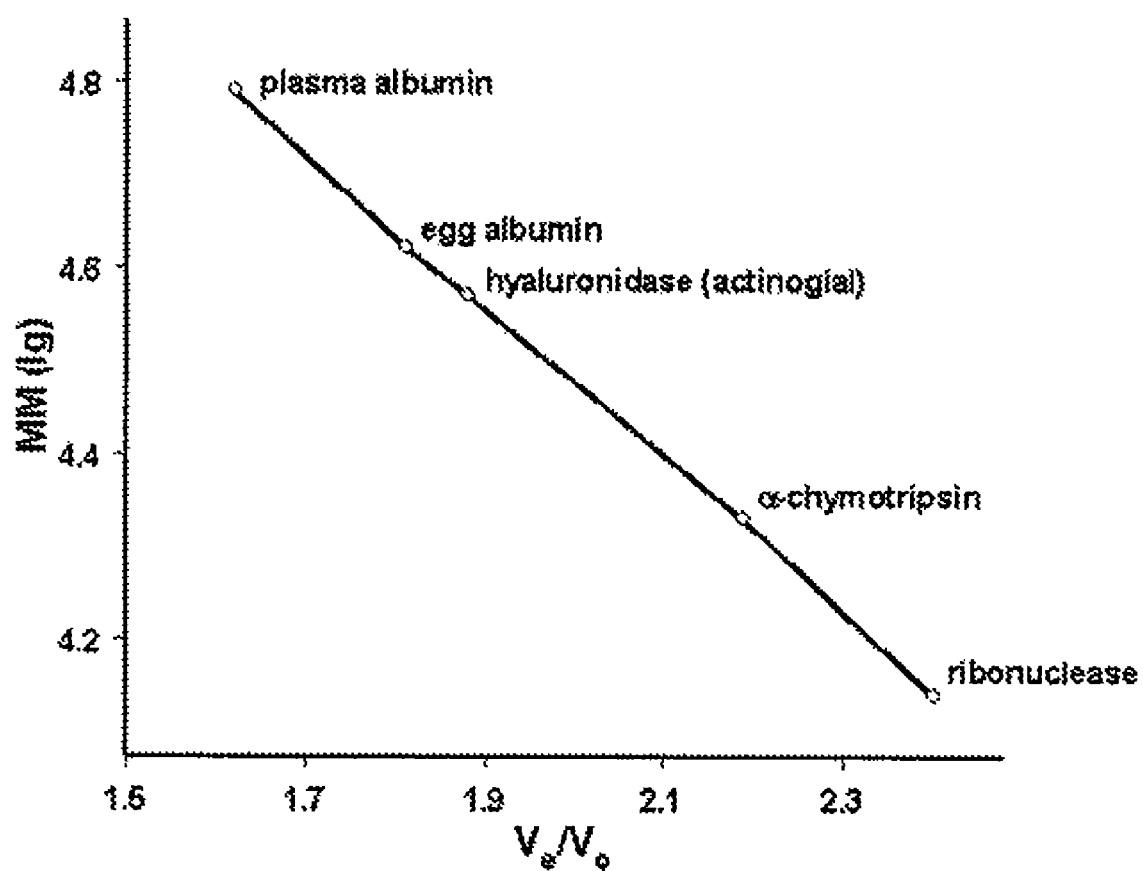

FIG. 2. Determination of the molecular weight of the hyaluronidase by gel-filtration. Column 1×50, Biogel P-100, PBS 0.05, pH 6.5, 5 mg/ml. 10 ml/hr.

Figure 3:
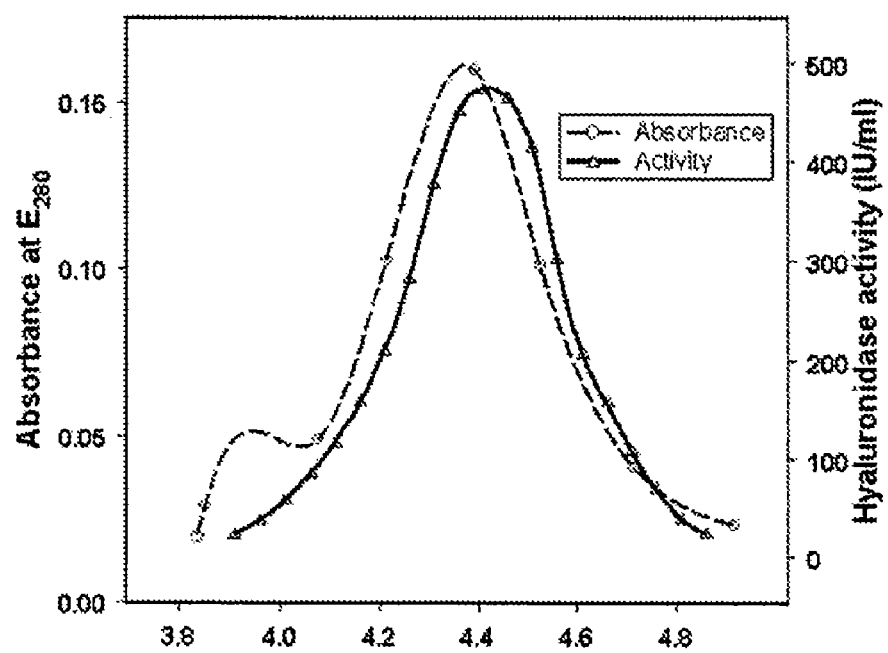

FIG. 3. Isoelectric focusing, of microbial hyaluronidase (10 mg) in pH gradient 4-6. Dashed line represents absorption at 280 nm. Triangles represent hyaluronidase activity.

Figure 4:
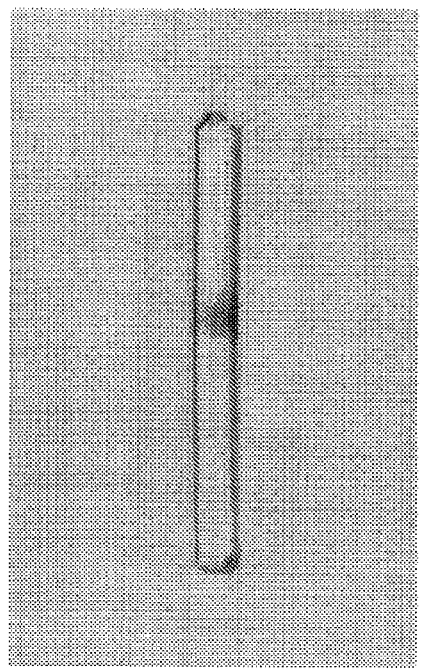
Figure 4:
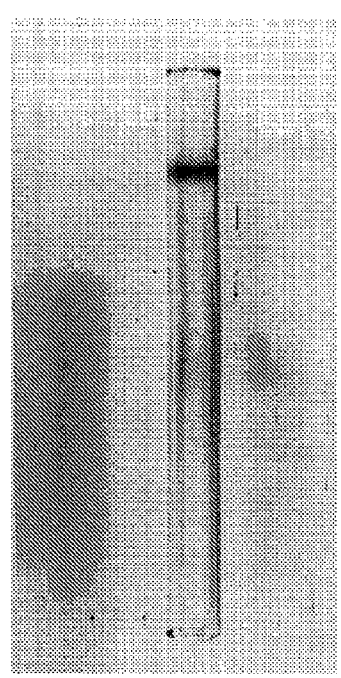

FIGS. 4A and 4B. Electrophoregram of homogenous hyaluronidase obtained from *Streptomyces*. (A) 150 μg of protein without addition of sodium dodecylsulfate and mercaptoethanol: (B) 80 μg of protein with addition of sodium dodecylsulfate and mercaptoethanol.

Figure 5:
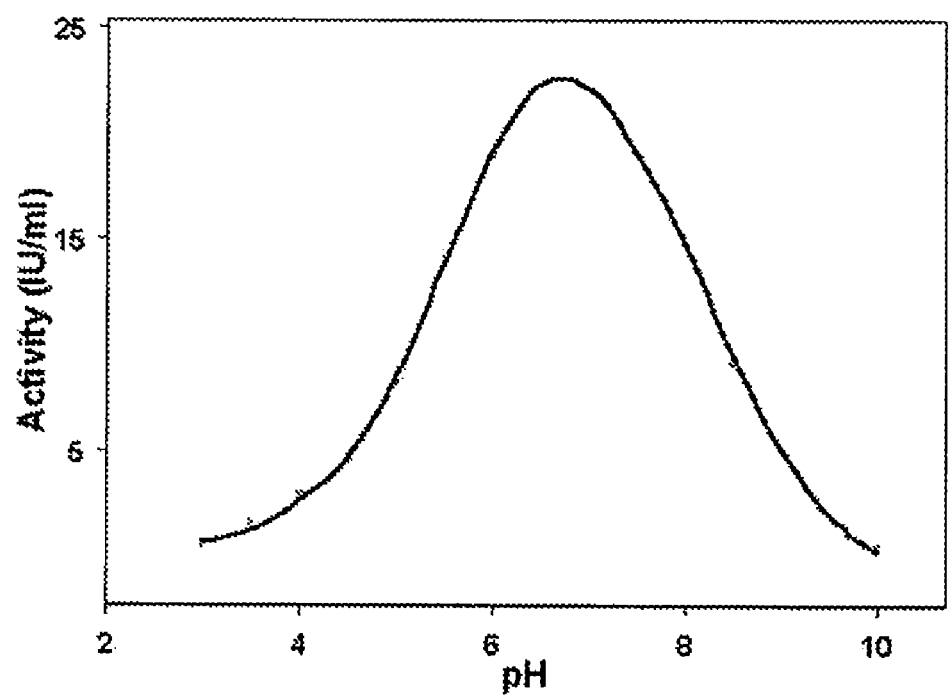

FIG. 5. Effect of pH on the activity of the hyaluronidase.

Figure 6:
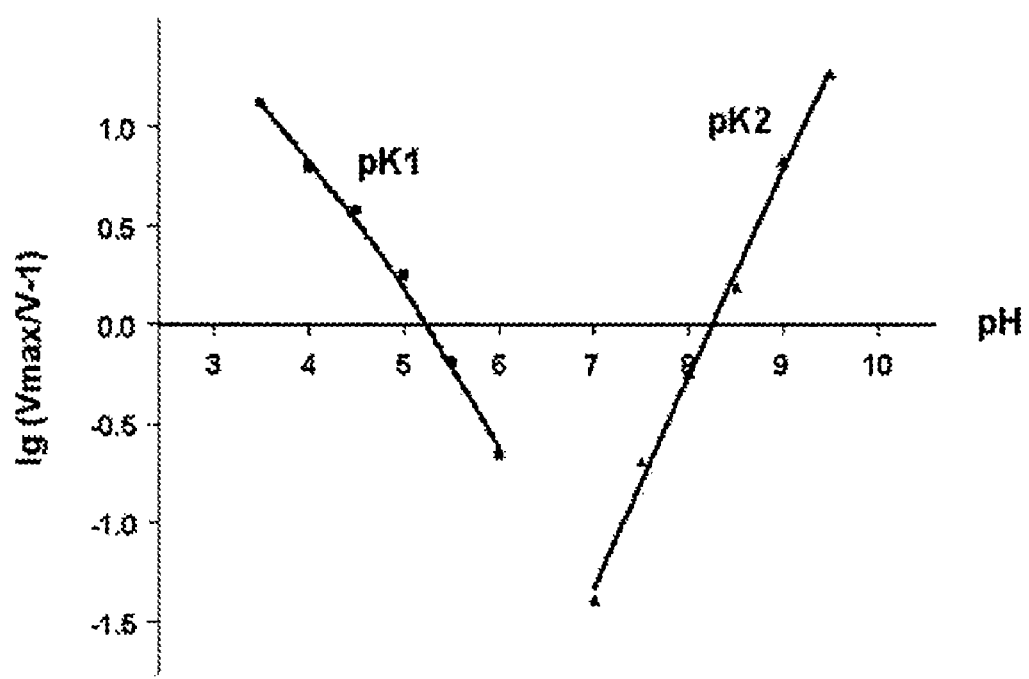

FIG. 6. Analysis of apparent dissociation constants of the hyaluronidase.

Figure 7:
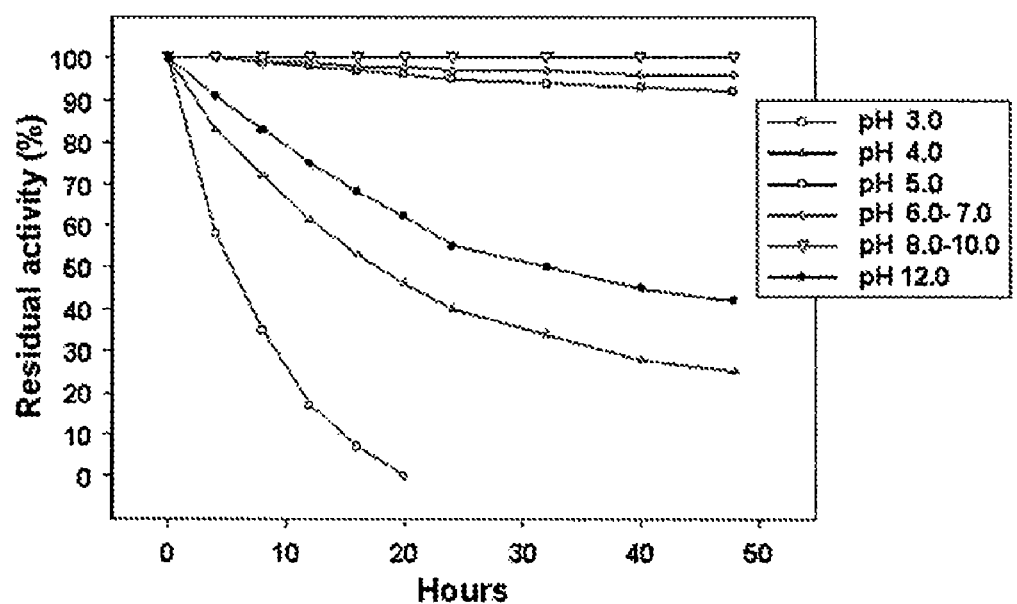

FIG. 7. Stability of the hyaluronidase (5×<10−4 g/ml) at 20° C. and different pH. (1) pH 6.0; (2) pH 7.0; (3) pH 8M; (4) pH 9.0 (5) pH 10.0; (6) pH 11.0; (7) pH 5.0 (8) pH 12.0; (9) pH 4.0; (10) pH 3.0.

Figure 8:
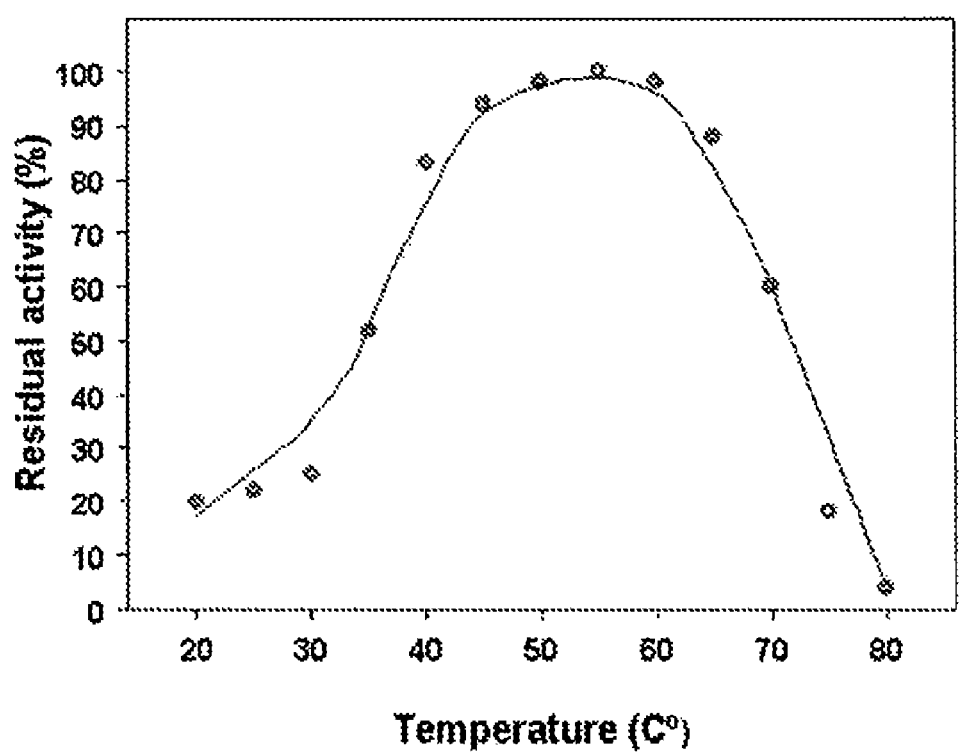

FIG. 8. Temperature optimum of the activity of the hyaluronidase activity (0.01 M PBS, pH 6.5).

Figure 9:
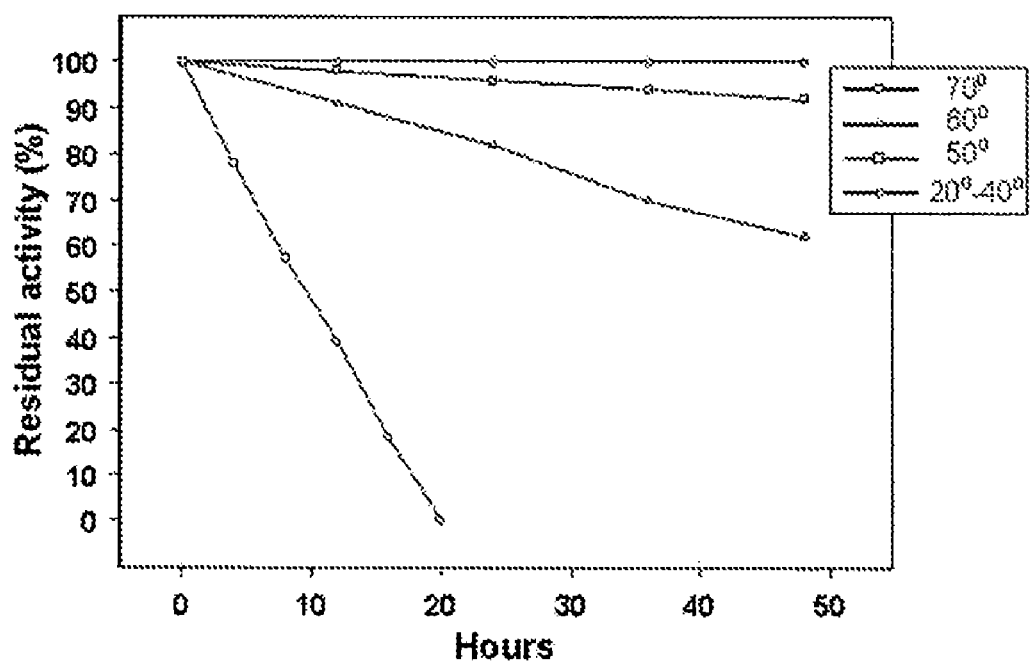

FIG. 9. Thermostability of the hyaluronidase (solution pH 6.5). 1-20° C.; 2-30° C. 3-40° C.; 4-50° C.; 5-60° C.; 6-70° C.

Figure 10:
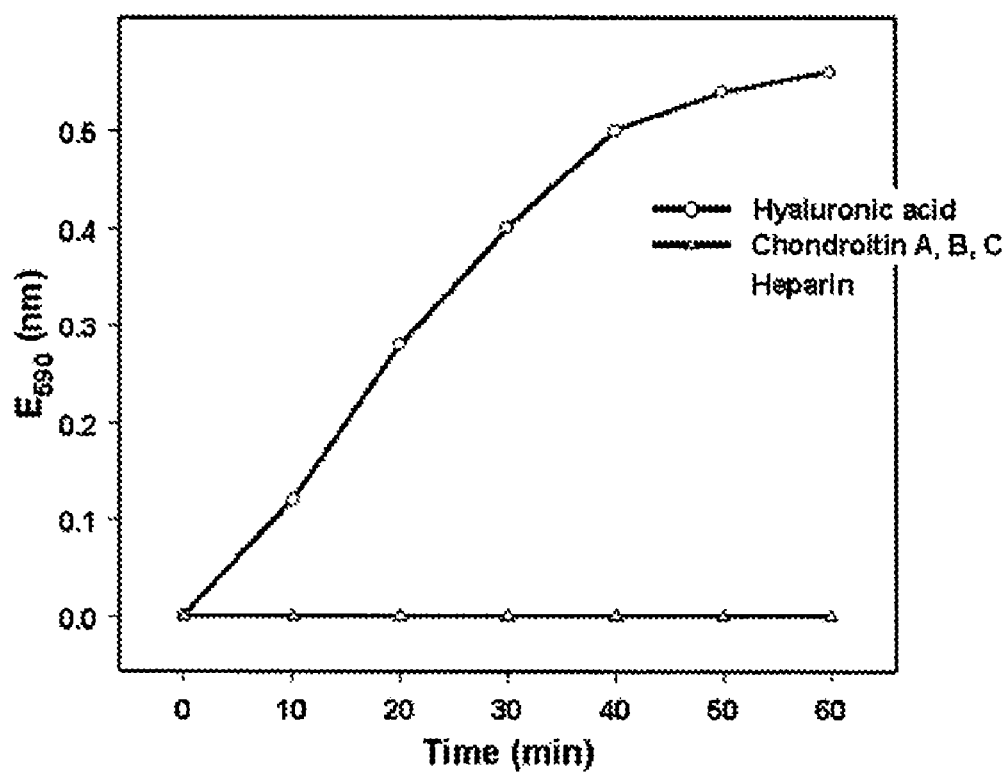

FIG. 10. Rate of hydrolysis of hyaluronic acid (I) and chondroitinsulfates A, B, C (2) by the hyaluronidase.

Figure 11:
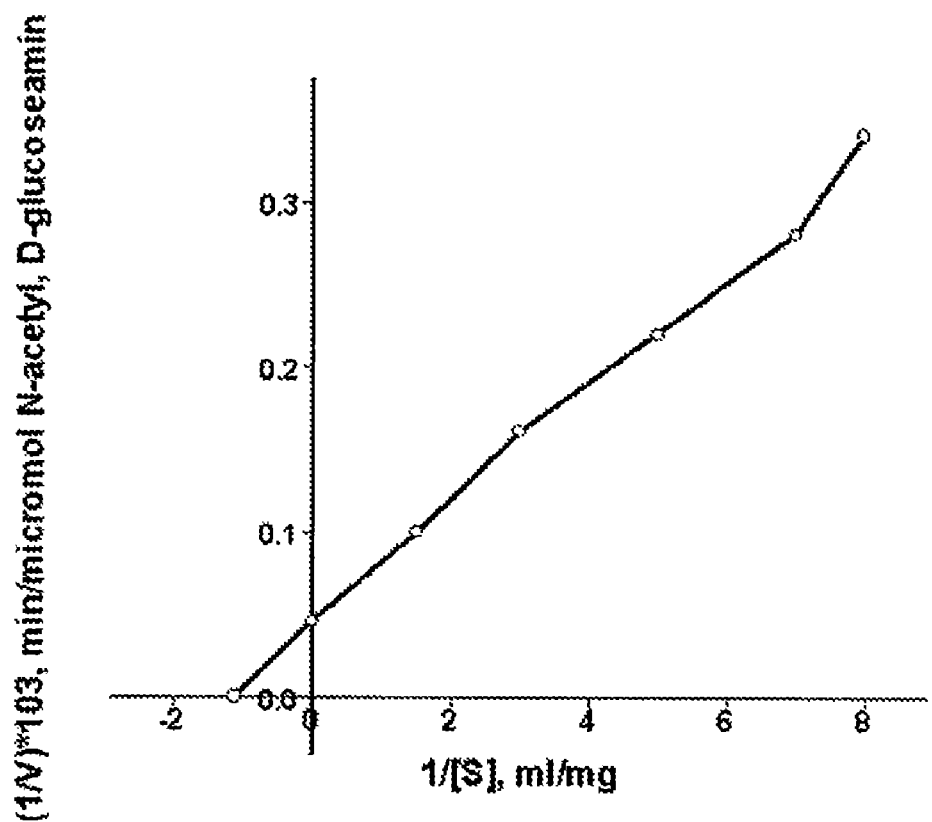

FIG. 11. Dependency of hyaluronic acidhydrolysis on substrate concentration (enzyme: 0.5 mg/ml; 0.1 M. PBS, pH 6.5).

Figure 12:
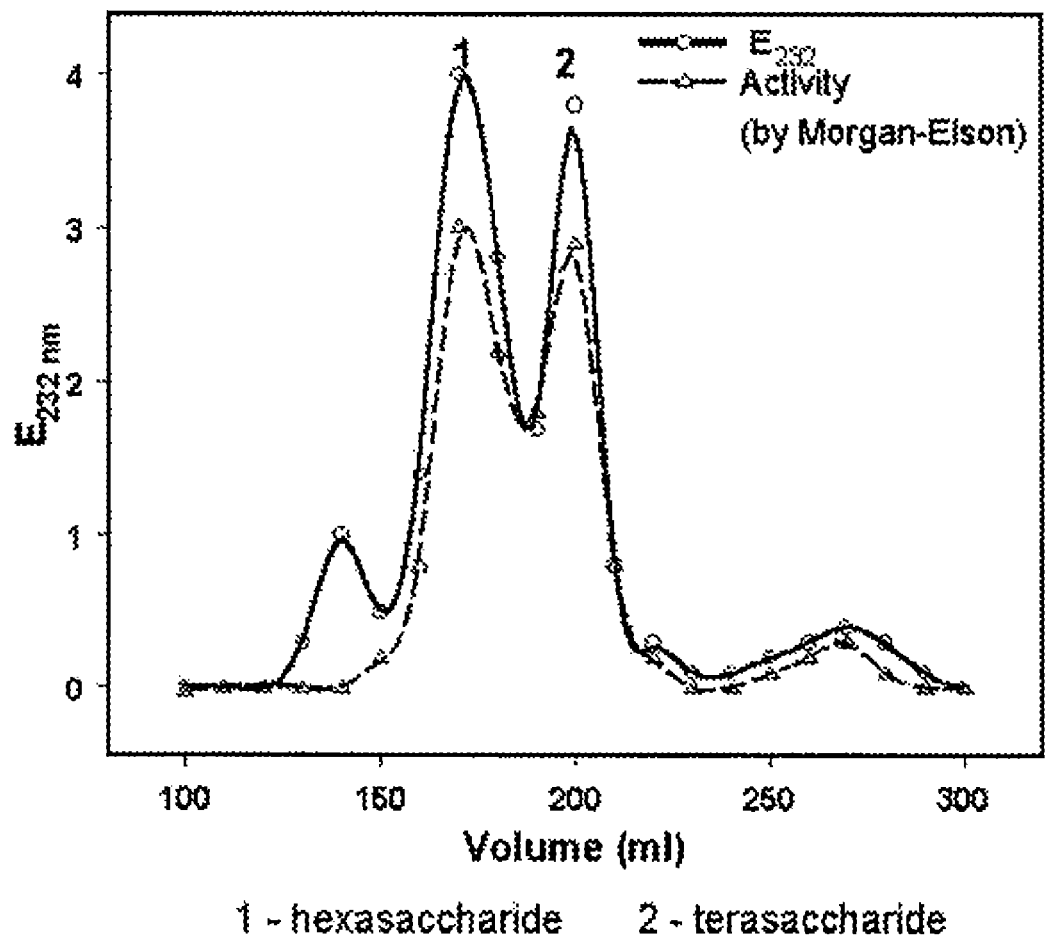

FIG. 12. Gel-filtration of the hydrolysis products after enzyme hydrolysis of hyaluronic acid.

Figure 13:
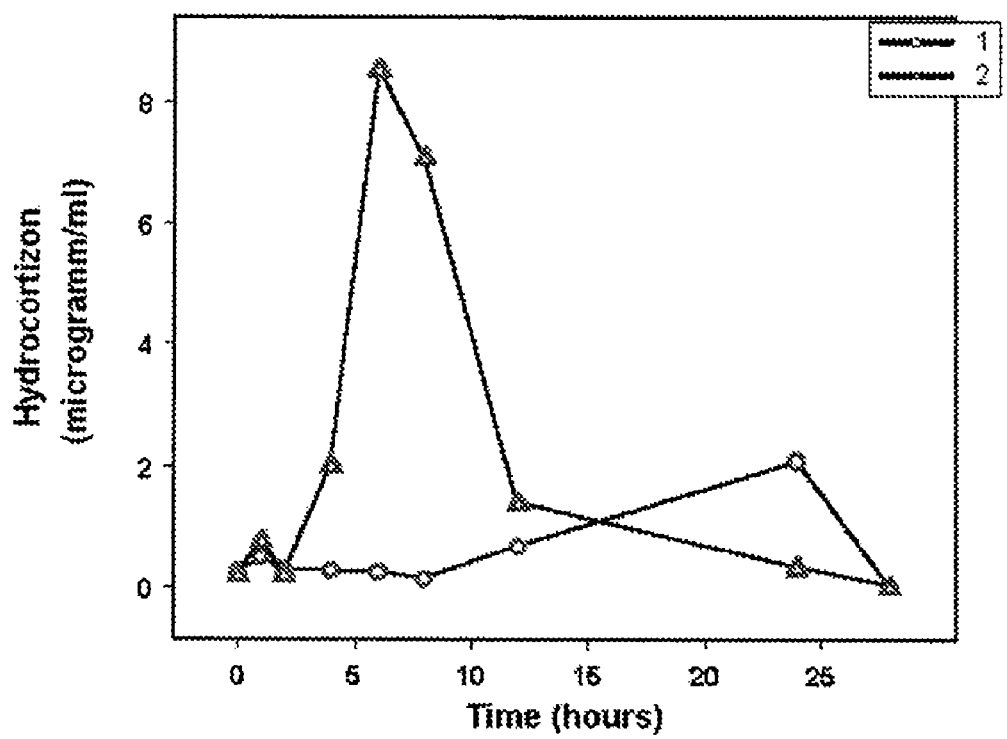

FIG. 13. Changes in plasma hydrocortisone level after ointment application.

Figure 14:
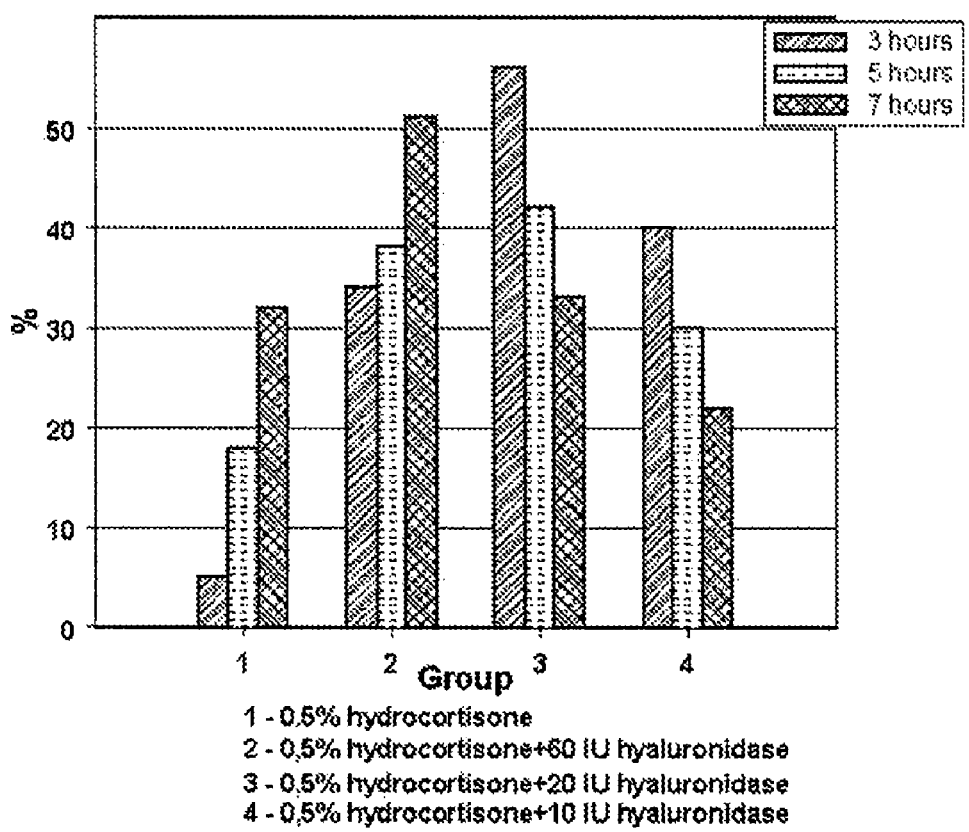

FIG. 14. Effects on the development of edema of ointments without the hyaluronidase and with different amounts of the hyaluronidase at different time points after application.

FIG. 15. Combined sequence information generated using degenerate PCR primers and *Streptomyces actinocidus* DNA. Protein translation is shown underlying the DNA sequence. Primer sequences are shown in small case; Forward primer—bases 1-38; Reverse 2—bases 421-449; Reverse 3—has 256-276; and Reverse 4—bases 277-306.

DETAILED DESCRIPTION OF THE INVENTION

The present invention provides a hyaluronidase or hyaluronate lyase, which can be produced by the strain *Streptomy-* ces *actinocidus* 77, deposited in the Central Museum of Industrial Microorganisms on Nov. 6, 1980, under the deposit number CMPM S-560. Another *Streptomyces actinocidus* strain, denoted 150, has also been identified and deposited as CMPM S-561.

As shown in the Examples, the enzyme of the invention possesses many advantages compared to other hyaluronidases known in the art. These advantages include (1) high specific activity; (2) high selectivity towards hyaluronate; (3) optimal activity close to physiological pH; (4) high solubility in saline; (5) high stability at room temperature; and (6) low toxicity. In addition, the enzyme of the invention is produced in a non-virulent, non-pathogenic bacterial strain, and can be prepared in a highly purified form at moderate costs. The action of the hyaluronidase can significantly modify tissue permeability, soften scars, improve joint mobility, and decrease or prevent contractures. As shown in the Examples, this bacterial enzyme is also less toxic than a preparation of testicular hyaluronidase commonly used in clinic.

The hyaluronidase of the invention can be used in a wide range of applications. The advantageous properties of the invention, including high specific activity, improved pH-stability, and/or high thermostability, allows for its use in providing improved drug deliver), of various active substances, for decreased drug dosage while maintaining efficacy, or for devising unconventional ways of drug delivery. Exemplary but non-limiting uses of the hyaluronidase described herein include: (1) use in various skin patches as a component of a medicinal composition to increase the efficiency of drug penetration and to provide continuous steady delivery of the drug (e.g., delivery of steroids through the skin instead of oral or parenteral administration); (2) for transdermal (through the skin) or transmucosal (through mucosa) drug delivery of, e.g., insulin; (3) to facilitate penetration, increase efficiency, or decrease the necessary amount, of active substance in antifungal medications (ointments, powders etc.); (4) to facilitate penetration of antibiotics into a damaged area via local delivery, or to provide a continuous steady blood concentration of antibiotics delivered transdermally or transmucosally; (5) in preparations for local application of active substances to stimulate or suppress hair growth; (6) for the treatment of chronic skin inflammatory processes, when delivery of the medication through the blood is compromised, e.g. due to the capsule formation; (7) to increase efficiency of local anesthetics; (8) to improve the efficiency of anti psoriasis drugs; (9) to improve the efficiency of anti-itching preparations; (10) to increase the efficiency of drugs used to treat precancerous lesions or cancer of the cervix through local administration; (11) in vaginal suppositories for treatment of, e.g., deep yeast infection; (12) in the treatment of fertility problems (e.g., egg impregnation, egg implantation, salpingitis etc.); (13) for the treatment of pathologies accompanied by capsule formation to facilitate drug delivery through the capsule; or (14) in oncology to increase the efficiency of antitumor therapy, for example, in melanoma.

Definitions

The term "active agent" or "active substance" includes pharmacological, cosmetic, or bioactive agents and refers to any chemical material or biological material which produces a desired effect. An active agent according to the invention also includes hyaluronidase, which can produce desired effects such as, for example, modified skin penetrability or reduced scar formation.

The term "drug" means any and all active agents including hyaluronidases. Non-limiting examples of drugs include anti-inflammatory agents, antifungal agents, chemotherapeutic agents, antibiotics, anti-microbial agents, antiviral agents, hormones such as insulin, cutaneous growth enhancers, including those for the hair and nails, hair care agents, antipsoriatics, retinoids, anti-acne medicaments, antineoplastic agents, topical anesthesetics, phototherapeutic agents, sunscreen, cutaneous protection agents, alpha-hydroxy acids (including lactic acid and glycolic acid), insect repellants and the like.

The term "effective amount" of an active agent refers to a nontoxic but sufficient amount of an active agent to provide the desired effect and performance at a reasonable benefit/risk ratio attending any medical treatment. The effective amount of a compound can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The efficacy and toxicity of a compound can be determined by standard pharmaceutical procedures in cell cultures or experimental animals, e.g., ED50 (the dose leading to the desired effect in 50% of the population) and LD50 (the dose lethal to 50% of the population). A pharmaceutically useful dosage lies preferably within a range that includes the ED50 with little or no toxicity. The dosage varies depending upon the disease or condition to be treated or prevented, dosage form employed, sensitivity of the patient, and the route of administration. The exact dosage is chosen by the individual physician in view of the patient to be treated.

The term "carrier" as used herein refers to a vehicle suitable for administration of active agents and includes any such liquid or non-liquid solvent, diluent or like material known in the cosmetic and medicinal arts, for forming any liquid or semisolid gel, cream, ointment, emulsion, aerosol., foam, lotion, or the like, and that does no adversely affect living animal tissue or interact with other components of the composition in a deleterious manner. Topical carriers are used to provide the compositions of the invention in their preferred liquid or non-solid form. Non-limiting examples of suitable topical carriers for use herein include water, liquid alcohols, liquid glycols, liquid polyalkated protein hydroyslates, liquid lanolin and lanolin derivatives, and like materials, and mixtures thereof.

The term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning; A Practical Approach*, Volumes I and II (D. N. Glover ed. 1985); *Oligonucleotide*

Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994). The meaning herein of some important terms are explained below.

The term "substrate" means any substance or compound that is converted or meant to be converted into another compound by the action of an enzyme. The term also includes combinations of compounds, such as solutions, mixtures and other materials which contain at least one substrate. Preferred substrates for hyaluronidase are hyaluronic acid and hyaluronate.

A "native" or "wild-type" protein, enzyme, polynucleotide, gene, or cell, means a protein, enzyme, polynucleotide, gene, or cell that occurs in nature.

A "full-length" enzyme means an enzyme which comprises all amino acid residues encoded by the coding region of the corresponding gene.

A "variant" of a full-length, wild-type hyaluronidase can have an amino acid sequence that is different by one or more amino acid substitutions, deletions or insertions. Variants also include fragments, preferably fragments that comprise at least 5, more preferably at least 50, and most preferably at least 100 sequential amino acids of the wild type enzyme. A substitution (a.k.a. "mutation") can be "function-conservative." Guidance in determining which and how many amino acid residues may be substituted, inserted or deleted without abolishing biological or immunological activity may be found using computer programs well known in the art, for example, DNAStar software.

A "function-conservative variant" is a proem or enzyme in which a given amino acid residue has been changed without altering overall conformation and function of the protein or enzyme, including, but not limited to, replacement of an amino acid with one having similar properties, including polar or non-polar character, size, shape and charge. Some selected properties of naturally occurring, amino acids are provided below.

| Amino Acid | SLC | Side Chain Property |
|---|---|---|
| Isoleucine | I | Hydrophobic |
| Leucine | L | Hydrophobic |
| Valine | V | Hydrophobic |
| Phenylalanine | F | Aromatic side chain |
| Methionine | M | Sulphur group |
| Cysteine | C | Sulphur group |
| Alanine | A | Hydrophobic |
| Glycine | G | Hydrophobic |
| Proline | P | Secondary amine |
| Threonine | T | Aliphatic hydroxyl |
| Serine | S | Aliphatic hydroxyl |
| Tyrosine | T | Aromatic side chain |
| Tryptophan | W | Aromatic side chain |
| Glutamine | Q | Amide group |
| Asparagine | N | Amide group |
| Histidine | H | Basic side chain |
| Glutamic acid | E | Acidic side chain |
| Aspartic acid | D | Acidic side chain |
| Lysine | K | Basic side chain |
| Arginine | R | Basic side chain |

"Sequence identity" herein means the extent to which two nucleotide or amino acid sequences are invariant Percent amino acid sequence identity with respect to the preferred polypeptide of the invention is defined herein as the percentage of amino acid residues in the candidate sequence that are identical with the residues in the hyaluronidase sequence after aligning both sequences and introducing, gaps, if necessary, to achieve the maximum percent sequence identity, and not considering any conservative substitutions as part of the sequence identity. According to the invention, a variant hyaluronidase may have a percent amino acid sequence identity of at least 40%. 50%, 60%, 70%, 80%, 90%, 95%, 97%, or 99% to SEQ ID NO:1 or SEQ NO:2 as determined according to an alignment scheme.

"Sequence alignment" means the process of lining up two or more sequences to achieve maximal levels of identity (and, in the case of amino acid sequences, conservation) for the purpose of assessing the degree of similarity. Numerous methods for aligning sequences and assessing, similarity/identity are known in the art such as, for example, the Cluster Method, wherein similarity is based on the MEGALIGN algorithm, as well as BLASTN, BLASTP, and PASTA. When using all of these programs, the preferred settings are default settings, or, alternatively, those that results in the highest sequence similarity.

The "enzyme activity" or "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. Preferred activity units for expressing, activity include the catalytic constant ($k_{cat}=v_{max}/E$; $v_{max}$ is maximal turnover rate: E is concentration of enzyme): the Michaelis-Menten constant ($K_m$); and $k_{cat}/K_m$. Such units can be determined using well-established methods in the art of enzymes.

The "specific activity" for an enzyme such as hyaluronidase or hyaluronidase preparation can be measured in International Units (IU) per gram or mol of enzyme or enzyme preparation. One unit of hyaluronidase is defined as the amount which during 1 min in a 0.3% w/v solution of substrate (potassium hyaluronate or hyaluronic add) at 37° C. and pH 6.5 will produce oligosaccharides in the amount equivalent to 1 mmol of N-acetyl-D-glucosamine (NAGA). The terms "better", "increased", "improved", or "superior" activity, or the like, means an activity compared to a prior art hyaluronidase such as Ronidase (and measured under the same conditions) that is at least about 10% higher, preferably at least about 25% higher, more preferably at least about 50% higher, more preferably at least about 75% higher, more preferably at least about 100% higher.

The term "immunological activity" defines the capability of a wild-type, recombinant or synthetic hyaluronidase, or any variant thereof, to induce an immune response specific to the hyaluronidase in appropriate animals or cells, and to hind with antibodies that bind to the enzyme.

The "stability" or "resistance" of an enzyme means its ability to function, over time, in a particular environment or under particular conditions. One way to evaluate stability or resistance is to assess its ability to resist a loss of activity over time, under given conditions. Enzyme stability can also be evaluated in other ways, for example, by determining the relative degree to which the enzyme is in a folded or unfolded state. Thus, one enzyme has improved stability or resistance over another enzyme when it is more resistant than the other enzyme to a loss of activity under the same conditions, is more resistant to unfolding, or is more durable by any suitable measure. For example, a more "thermostable" enzyme is one that is more resistant to loss of structure (unfolding) or function (enzyme activity) when exposed to increasing temperatures, and a more "pH-stabe" enzyme is one that is more resistant to loss of structure or activity as the pH-value of the solution is increased or decreased from the optimum pH-value.

A "promoter sequence" is a DNA regulatory region capable of binding RNA polymerase in a cell and initiating transcription of a downstream (3' direction) coding sequence. For purposes of defining this invention, the promoter sequence is bounded at its 3' terminus by the transcription initiation site and extends upstream (5' direction) to include the minimum number of bases or elements necessary to initiate transcription at levels detectable above background.

Polynucleotides are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such is for example, an aqueous solution of 2×SSC at 55° C.), require correspondingly less overall complementarity between the hybridizing sequences, 1×SSC is 0.15 M NaCl, 0.015 M Na citrate.

The term "expression system" means a host cell and compatible vector under suitable conditions, e.g. for the expression of a protein coded for by foreign DNA carried, by the vector and introduced to the host cell. Common expression systems include bacteria (e.g., *E. coli, B. subtilis*, and *Streptomyces*) or yeast (e.g., *S. cerevisiae*) host cells and plasmid vectors, and insect host cells and Baculovirus vectors. *E. coli* and *Streptomyces* are preferred host cells of the invention.

The terms "vector", "vector construct" and "expression vector" mean the vehicle by which a DNA or RNA sequence (e.g., a foreign gene) can be introduced into a host cell, so as to transform the host and promote expression (e.g., transcription and translation) of the introduced, sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA, that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clontech, Mountain View, Calif.), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

"Isolation" or "purification" of a polypeptide or enzyme refers to the derivation of the polypeptide by removing it from its original environment (for example, from its natural environment if it is naturally occurring, or form the host cell if it is produced by recombinant DNA methods). Methods for polypeptide purification are well-known in the art, including, without limitation, preparative disc-gel electrophoresis, isoelectric focusing, HPLC, reversed-phase HPLC, gel filtration, ion exchange and partition chromatography, affinity chromatography, and countercurrent distribution. A purified polynucleotide or polypeptide may contain less than about 50%, preferably less than about 75%, and most preferably less than about 90%, of the components with which it was originally associated.

Hyaluronidase

The hyaluronidase of the invention, is characterized by both specific amino acid sequences and specific physicochemical properties. For example, a preferred hyaluronidase has at least one, preferably at least two, more preferably at least three, and even more preferably all of the following properties; optimal activity in the pH range of about 6.5 to about 7.0; optimal activity at between about 50° C. and about 60° C.; isoelectric pH of about 4.4; molecular weight of about 44±1 kD. In addition, the hyaluronidase preparation preferably has at least one, preferably all least two, more preferably at least three, and even more preferably at least 4 of the following characteristics: very low or no activity towards chondroitin sulfate A, B, and C, and heparin $K_m$ for potassium hyaluronate of about 1.1 mg/ml; $V_{max}$ for potassium hyaluronate of about 0.022 micromole of N-acetyl-D-glucosamine/min; solubility in saline solution of about 1 g per about 10 ml to about 30 ml; and a specific activity of at least about 20 IU/g, more preferably at least about 200 IU/g, and most preferably al least about 2000 IU/g preparation.

Preferred hyaluronidases can also have a C-terminal sequence comprising SEQ ID NO:1 and/or comprise the sequence of SEQ NO:2. The first, amino acid residue of SEQ ID NO:2 can be either aspartic acid or glycine. In yet another embodiment, the hyaluronidase comprises the full sequence of the *S. actinocidus* hyaluronidase, or a variant thereof having at least 60%, at least 70%, at least 80%, at least 90%, at least 95%, at least 97%, or at least 99% sequence identity. Preferred variants are those that are function-conservative variants, and in which an amino acid residue in the wild-type protein is substituted with an amino acid having similar physicochemical properties.

Enzyme Production

The hyaluronidase of the invention is an enzyme possessing one or more of the physico-chemical., structural, functional, or immunological characteristics of the hyaluronidase, and can be isolated from any species expressing the protein, including bacterial (*Streptomyces, Streptococcus*, etc., or bacterial host cells such as *E. coil*), or mammalian, including bovine, ovine, porcine, murine, equine., and human, and from any source, whether natural, synthetic, semi-synthetic or recombinant. Alternatively, the hyaluronidase can be synthesized by conventional peptide or protein synthetic techniques.

From *Streptomyces actinocidus*, the enzyme of the invention can be produced by culturing the cells under conditions suitable for expression and/or secretion of the hyaluronidase, harvesting enzyme, and purifying the enzyme preparation using, for example, one or more of the purification methods described in FIG. 1. For example, *Streptomyces actinocidus* can be cultured by the so called "deep-laid method," in which the mycelium separated, and the enzyme purified chromatographically on an acidic hydrolysis carboxyl cationic KM2p column (e.g., Biocarb-K), and de-colored with activated carbon. This method can be carried out as follows: Initial growth of *Streptomyces actinocidus* is carried out on hard media, Chapek media with glucose or Gause media, for 9 days at a temperature of about 28-30° C. Colonies are transferred into round glass bottles with sterile liquid media containing approximately 1% starch, 0.5% peptone, 0.5% meat-peptone broth, 0.1% potassium phosphate; 0.8% ammonium sulfate, at pH 7.0-7.2. The media is aerated and agitated for about 48 hours. The cells are further grown in fermenters in sterile media containing approximately 2.5% fementolysate or hydrolysate or autolysate of microorganismic biomass (e.g., yeast), 0.8% ammonium sulfate; 0.1% potassium phosphate, pH 7.0-7.2. The media is agitated and aerated at about 28-30° C. for about 58-60 hours, and then separated from product with press-filtering processing or flow-through centrifugation. Further purification can be carried out according to either one of the routes set forth in FIG. 1.

Alternatively, the gene for the hyaluronidase can be identified and sequenced according to methods well-known in the art, an expression vector constructed, and the enzyme produced recombinantly in a chosen host cell. For example, oligonucleotide probes corresponding or complementary to it nucleotide sequence encoding for at least 3, preferably at least 5, and more preferably, at least 10 sequential amino acids of SEQ ID NOS: 1, 2, or 4 can be used to identify genomic DNA, or mRNA, for the hyaluronidase. Expression vectors can then be constructed by inserting a nucleotide sequence encoding for the enzyme or a variant thereof into any suitable vector known in the art for expression in, for example, *E. coli* Or *Streptomyces*.

With the knowledge of the nucleotide sequence information disclosed in the present invention, one skilled in the art can identify and obtain nucleotide sequences which encode the hyaluronidases of the invention from different sources through a variety of means well known to the skirled artisan and as disclosed by, for example, Sambrook et. al., supra.

A nucleic acid molecule encoding, a variant of the hyaluronidase may be obtained using any means of mutagenesis performed on the wildtype sequence. Such methods include PCR assays including error prone and degenerate PCR, use of mutagenic strains such as the XL1-Red mutator strain of *E. coli* (Stratagene Inc.), use of random mutagenesis methods involving mutagenic chemicals such as ethyl-methyl sulfonate (EMS) or involving irradiation by UV light or other radiations of higher or lower energy, combinatorial cassette mutagenesis Delagrave, et al., Bio/Technology 1993; 10:1548-52), site-directed mutagenesis, mutagenesis by PCR involving the incorporation of one or more primers encoding mutations, mutagenesis by DNA shuffling (e.g., Stemmer, Nature 1994; 370:389, and other closely related methods), and mutagenesis by any PCR method.

A nucleic acid molecule comprising any of the hyaluronidase nucleotide sequences described above can alternatively be synthesized by use of the polymerase chain reaction (PCR) procedure, with the PCR oligonucleotide primers produced from the nucleotide sequences provided herein. See U.S. Pat. Nos. 4,683,195 and 4,683,202 to Mullis. PCR provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotides probes to serve as primers for the template-dependent, polymerase mediated replication of a desired nucleic acid molecule. A wide variety of alternative cloning and in vitro amplification methodologies are well known to those skilled in the art. Examples of these techniques are found in, for example. Berger et al., Guide to Molecular Cloning Techniques, Methods M Enzymology 152 Academic Press, Inc., San Diego, Calif. (Berger).

Another aspect of the present invention is directed to vectors, or recombinant expression vectors, comprising any of the nucleic acid molecules described above. Vectors are used herein either to amplify DNA or RNA encoding the hyaluronidase and/or to express DNA which encodes the hyaluronidase. Exemplary vectors include, but are not limited to plasmids, phages, cosmids, episomes, viral particles or viruses, and integratable DNA fragments (i.e., fragments integratable into the host genome by homologous recombination). Preferred viral particles include, but are not limited to, adenoviruses, baculoviruses, parvoviruses, herpesviruses, poxviruses adeno-associated viruses, Semliki Forest viruses, vaccinia viruses, and retroviruses. In expression vectors, a DNA sequence encoding the hyaluronidase is operably linked or connected to suitable control sequences capable of effecting the expression of the hyaluronidase in a suitable host. DNA regions are operably linked or connected when they are functionally related to each other. For example, a promoter is operably linked or connected to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences in the expression vector will vary depending upon the host selected and the transformation method chosen. Generally, control sequences include a transcriptional promoter, an optional operator sequence to control transcription, a sequence encoding, suitable mRNA ribosomal binding, and sequences which control the termination of transcription and translation. Exemplary expression vectors include, but are not limited to, pcDNA3 (invitrogen) and pSVL (Pharmacia Biotech). Other expression vectors include, but are not limited to, pSPORT vectors, pGEM vectors (Promega), pPROEXVectors (LTI, Bethesda, Md.), Bluesctipt vectors (Stratagene), pQE vectors (Qiagen), pSE420 (Invitrogen), and pYES2 (Invitrogen).

Vectors can contain a promoter that is recognized by the host organism. The promoter sequences of the present invention may be prokaryotic, eukaryotic or viral. Examples of suitable prokaryotic sequences include the $P_R$ and $P_L$ promoters of bacteriophage lambda (The bacteriophage Lambda, Hershey, A. D.; Ed., Cold Spring Harbor Press, Cold Spring Harbor, N.Y. (1973), which is incorporated herein by reference in its entirety; Lambda I I, Hendrix, R. W., Ed., Cold Spring Harbor Press, Cold Spring Harbor, N.Y. (1980), which is incorporated herein by reference in its entirety): the trp, recA, heat shock, and lacz promoters of *E. coli* and the SV40 early promoter (Benoist, et al. Nature, 1981; 290:304-310, which is incorporated herein by reference in its entirety). Additional promoters include, but are not limited to, mouse mammary tumor virus, long terminal repeat of human immunodeficiency virus, maloney virus, cytomegalovirus immediate early promoter, Epstein Barr virus, rous sarcoma virus, human actin, human myosin, human hemoglobin, human muscle creatine, and human metallothionein. Additional regulatory sequences can also be included in preferred vectors. Preferred examples of suitable regulatory sequences are represented by the Shine-Dalgarno of the replicase gene of the phage MS-2 and of the gene di of bacteriophage lambda. The Shine-Dalgarno sequence may be directly followed by DNA encoding the hyaluronidase and result in the expression of the mature hyaluronidase protein. Suitable expression vectors can also include an appropriate marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and hyaluronidase DNA. An example of a suitable marker is dihydrofolate reductase (DHFR) or thymidine kinase. (see, U.S. Pat. No. 4,399,216).

Nucleotide sequences encoding hyaluronidase may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example. Okayama et al., Mol. Cell, Biol. 1983; 3:280, Cosman et al., Mol. Immunol. 1986; 23:935; Cosman et al., Nature 1984; 312:768, EP-A-0367566, and WO 91/18982, each of which is incorporated herein by reference in its entirety.

Another embodiment of the present invention is directed to transformed host cells having an expression vector comprising any of the nucleic acid molecules described above. Expression of the nucleic acid sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Psendomonas, Streptomyces*, and *Staphylococcus*. If a eukaryotic expression vector is employed, then the appropriate host cell would be any eukaryotic cell capable of expressing the cloned sequence. Exemplary eukaryotic cells include, but are not limited to non-human mammalian tissue culture cells and human tissue culture cells, for example, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, Tissue Culture, Academic Press, Kruse and Patterson, eds. (1973), which is incorporated herein by reference in its entirety). In addition, a yeast host may be employed as a host cell. Preferred yeast cells include, but are not limited to, the genera *Saccharomyces, Pichia*, and *Kluyveromyces*. Preferred yeast hosts are *S. cerevisiae* and *P. pastoris*. Preferred yeast vectors can contain an origin of replication sequence from a 2T yeast plasmid, an autonomously replication sequence (ARS), a promoter region., sequences for polyadenylation, sequences for transcription termination, and a selectable marker gene. Shuttle vectors for replication in both yeast and *E. coli* are also included herein. Alternatively, insect cells may be used as host cells. In a preferred embodiment, the polypeptides of the invention are expressed using a baculovirus expression system see, Luckow et al., Bio/Technology, 1988, 6, 47, Baculovirus Expression Vectors: A Laboratory Manual, O'Rielly et al. (Eds.), W.H. Freeman and Company, New York, 1992, and U.S. Pat. No. 4,879,236, each of which is incorporated herein by reference in its entirety). In addition, the MAXBAC™ complete baculovirus expression system (Invitrogen) can, for example, be used for production in insect cells.

After recombinant production of the hyaluronidase or a variant thereof, similar purification methods to those described in FIG. 1 can be applied to retrieve a substantially pure enzyme preparation. The hyaluronidase preparations of the invention can then be tested for various properties using methods described herein. For example, the physicochemical properties (optimal pH and temperature, pH- and thermostability, salt and reagent tolerance, solubility) as well as hyaluronidase specificity and activity assays are provided in e.g., Examples 1-3 and 6. Pharmacokinetic parameters and in vivo effects can be studied as described in Examples 4 and 5. Toxicity and efficacy studies are reported in Example 7, and immunological parameters are described in Examples 8 and 9.

Antibodies

The invention also provides antibodies specific to the hyalonidases of the invention, including antibodies specific for one or more or SEQ ID NOS:1-2, 4. Such antibodies include but are not limited to polyclonal, monoclonal, chimeric, single chain. Fab fragments, and Fab expression library.

The term "specific for," when used to describe antibodies of the invention, indicates that the variable regions of the antibodies of the invention recognize and bind the hyaluronidase polypeptides of the invention exclusively are able to distinguish such polypeptides from other known hyaluronidases or proteins by virtue of measurable differences in binding affinity, despite the possible existence of localized sequence identity, homology, or similarity between the hyaluronidases of the invention and other protein). It will be understood that specific antibodies may also interact with other proteins (for example, *S. aureus* protein A or other antibodies in ELISA techniques) through interactions with sequences outside the variable region of the antibodies, and, in particular, in the constant region of the molecule. Screening, assays to determine binding specificity of an antibody of the invention are well known and routinely practiced in the art. For a comprehensive discussion of such assays, see Harlow et al. (Eds.), Antibodies A Laboratory Manual; Cold Spring Harbor Laboratory; Cold Spring Harbor, Y. (1988), Chapter 6. Antibodies that recognize and bind fragments of the hyaluronidase polypeptides of the invention are also contemplated, provided that the antibodies are specific for the hyaluronidase polypeptides provided by the invention. Antibodies of the invention can be produced using any method well known and routinely practiced in the art.

Various procedures known in the art may be used for the production of polyclonal antibodies to hyaluronidase polypeptides. For the production of antibody, various host animals can be immunized by injection with the antigenic polypeptide, including but not limited to rabbits, mice, rats, sheep, goats, etc.

For preparation of monoclonal antibodies directed toward the hyaluronidase polypeptides, any technique that provides for the production of antibody molecules by continuous cell lines in culture may be used. These include but are not limited to the hybridoma technique originally developed by Kohler and Milstein (Nature 1975; 256:495-497), as well as the trioma technique, the human B-cell hybridoma technique (Kozbor et al., Immunology Today 1983; 4:72; Cote et al., Proc. Natl. Acad. Sci. U.S.A. 1983; 80:2026-2030), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of the invention, monoclonal antibodies can be produced in germ-free animals (International Patent Publication No. WO 89/12690).

According to the invention, techniques described for the production of single chain antibodies (U.S. Pat. Nos. 5,476,786 and 5,132,405 to Huston; U.S. Pat. No. 4,946,778) can be adapted to produce the hyaluronidase polypeptide-specific single chain antibodies. Indeed, these genes can be delivered for expression in vivo. An additional embodiment of the invention utilizes the techniques described for the construction of Fab expression libraries (Huse et al. Science 1989; 246:1275-1281) to allow rapid and easy identification of monoclonal Fab fragments with the desired specificity for a hyaluronidase polypeptide, or its derivatives or analogs described herein. Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the an, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding. In an immunoassay and are within the scope of the present invention.

Drugs

In one embodiment, the hyaluronidase is utilized to enhance drug absorption or delivery, including, but not limited to, transdermal delivery. Exemplary drugs include corticosteroids such as hydrocortisone, prednisolone, beclomethasone-propionate, flumethasone, triamcinolone, triamcinolone-acetonide, fluocinolon, fluocinolinacetonide, fluocinolon-acetonide acetate, clobetasol-propionate, etc.; analgesics and/or anti-inflammatory agents such as acetaminophen, mefenamic acid, flufenamic acid, diclofenac, diclofenac-sodium-alclofenac, oxyphenbutazone, phenylbutazone, ibuprofen, flurbiprofen, salicylic acid, 1-menthol, camphor, sulindac-tolmetin-sodium, naproxen, fenbufen, etc.; antihypertensives such as pindolol, indenolol, nifedipin, lofexidin, nipradinol, bucumolol, etc.; antibiotics such as penicillin, tetracycline, oxytetracycline, fradiomycin sulfate, erythromycin, chloramphenicol, etc., anesthetics such as lidocaine, benzocaine, ethylaminobenzoate, etc.; antimicrobiological agents such as benzalkonium chloride, nitrofurazone, nystatin, acetosulfamine, clotrimazole, etc.; antifungal agents such as pentamycin, amphotericin B, pyrrolnitrin, clotrimazole, etc.; vitamins such as vitamin A, ergocalciferol, chlolecalciferol, octotiamine, riboflavin butyrate, etc.; anticancer agents such as 5-fluorouracil, methotrexate, etc., antihistamines such as diphenyl hydromine hydrochloride, chlorpheniramine, diphenylimidazole, etc.; peptide hormones such as insulin, glucagon, and glucagon-like peptide 1 or 2, and other agents.

One exemplary drug is hydrocortisone (cortisol; oxicorticosterone), a corticosteroid routinely used in clinic as a anti-inflammatory and desensitizing agent. Its action is based on the suppression of protein synthesis in plasmatic cells and histamine production in mast cells, which decreases antibody production, capillary permeability, and subsequently depresses granulation development and scar formation.

Cosmetic Agents

In one embodiment, the hyaluronidase is utilized to enhance the delivery, including, but not limited to, transdermal delivery, of a cosmetic agent. Exemplary cosmetic agents include *calendula*, henna, sulfur, skin-calming agents, and hydrating agents.

Formulations

The present invention relates to pharmaceutical or cosmetic compositions which may comprise the hyaluronidase alone or in combination with at a stabilizer, excipient, carrier, diluent, or auxiliary agent, which may be administered, in any biocompatible pharmaceutical carrier, including, but not limited to, saline, buffered saline, dextrose, and water. Any of these formulations can be administered to a patient alone, or in combination with other drugs or cosmetic agents. In certain pharmaceutical compositions, the enzyme is mixed with excipient(s) or pharmaceutically acceptable carriers in a sterile formulation. In one embodiment of the present invention, the pharmaceutically acceptable carrier is pharmaceutically inert.

Typically, before formulation, the hyaluronidase preparation is an amorphous powder or foamy pellet which is of creamy-white or light-beige color and has a specific odor. The preparation can be stored in a dry light-protected place at 0-10° C. for about 1.5 years, preferably together with a stabilizer. Any suitable stabilizer can be used, such as alcohols and carbohydrates, widely used as stabilizer-fillers for enzyme drugs. For example, lactose, mannite and polyvinylpyrrolidone (MW 12600) have been tested as stabilizers for the hyaluronidase. Polyvinylpyrrolidone made determination of protein amount and specific activity difficult. After 1 year in a preparation with lactose, about 25-30% of the enzyme was inactive. Of these stabilizers, mannite 0.09-0.11 g/300 IU) is preferred. A freshly made solution of the hyaluronidase can be stored in refrigerator for up to 24 hours. In medical practice, it can be formulated as a clear solution or as a component of an ointment or cream together with one or more topical carriers. Various types of applicators such as bandages, compresses, pads, or tampons, can be prepared by adding hyaluronidase solution or dry powder to the applicator. These embodiments are described in more detail below.

A preparation suitable for skin application via an applicator can consist of microbial hyaluronidase and mannite (0.09-0.11 g per 300 IU of enzyme), packed as a powder in a penicillin or sterile, vial. A solution is prepared by dissolving content of one vial in 5-10 ml (30-60 IU/ml) of sterile isotonic solution of sodium chloride or sterile water, and the solution added to gauze, bandages, tampons, etc. if desired, although not necessarily, mannite can be included in the preparation.

Administration of hyaluronidase compositions can accomplished orally or parenterally, and may be administered by suitable delivery vehicles. Methods of parenteral delivery include topical, intraarterial, intramuscular, subcutaneous, intramedullary, intrathecal, intraventricular, intravenous, intraperitoneal, or intranasal administration. In addition to the active ingredients, the pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Mack Publishing Co, Easton Pa.).

Pharmaceutical compositions for oral administration can be formulated, using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient. Pharmaceutical preparations for oral use can be obtained through combination of active compounds with solid excipient, optionally grinding a resulting mixture, and processing the mixture of granules, after adding suitable auxiliaries, if desired. Suitable excipients are carbohydrates or proteins such as sugars, including lactose, sucrose, mannitol, or sorbitol, starch from corn, wheat, rice, potato, or other plants: cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate. Dyestuffs or pigments may be added to the formulations for product identification or to characterize the quantity of active compound, i.e., dosage.

Preferred oral formulations are those suitable for delivering the hyaluronidase to the oral cavity or esophagus. Such formulations are known in the art and include, e.g., microspheres, liquids, gels, suspensions, and slurries. See, e.g., Bernkop-Schnurch and Walker, Cut Rev Ther Drug Carrier Syst 2001; 18:59-501.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical application, a solution, suspension, gel, paste, balm, cream or other formulation of the hyaluronidase, with or without an additional active agent, can be used. Acceptable diluents, auxiliary agents, and excipients for topical use are well known in the pharmaceutical and cosmetic field, and are described, for example, in Remington's Pharmaceutical Sciences, Mack Publishing Co., (A. R. Gennaro edit. 1985). The materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine; proteins such as serum albumin gelatin, or immunoglobulins hydrophilic polymers such as polyvinylpyrrolidinone; natural or synthetic oils, including vegetable oil; wax; glycerine, amino acids such as glycine, glutamic acid, aspartic acid, or arginine; monosaccharides, disaccharides, and other carbohydrates including cellulose or its derivatives, glucose, lactose, mannose or dextrins, chelating agents such as EDTA, sugar alcohols such as mannitol or sorbitol, salts such as sodium chloride, and nonionic surfactants such as Tween, Pluronics or polyethyleneglycol. Other suitable excipients or carriers are described throughout the present disclosure. A preferred excipient is mannite (mannitol). For example, one preferred preparation is a lyophilized powder of hyaluronidase suspended or dissolved in 1 mM-50 mM histidine, 0.1%-2% sucrose, 2%-7% mannitol at a pH range of 4.5 to 5.5 that may be combined with a buffer of neutral pH prior to use, if desired.

The formulations may also comprise an additional active agent apart from the hyaluronidase, i.e., a drug or cosmetic agent. For example, hydrocortisone ointments may be prepared that contain about 10, 20 or 60 IU of the microbial hyaluronidase. Exemplary hydrocortisone formulations are as follows (by weight): (1) 0.5% hydrocortisone; 1% hyaluronidase; 50% polyethylenoxide; 40% glycerin; and 8.5% phosphate buffer (pH 6.5); (2) 0.5% hydrocortisone; 1% hyaluronidase; 50% polyethylenoxide; 47% glycerin; and 8% vaseline:lanolin. Polyethyleoxide can be used in various amounts (e.g., 1500, or 400:4000 (1:1), and sodium oxybutyrate (2.5-5%) or trimecaine (1%) could also be added.

Hyaluronidase in combination with drugs such as hydrocortisone, antibiotics, vitamins, and/or hyaluronidase can be administered by, e.g., intravenous, subcutaneous, or intramuscular injection; orally in the form of gels, slurries, or suspensions, or topically as Ointments, creams, face masks, and cosmetic lotions; or transdermally using a transdermal delivery system. Exemplary formulations for cosmetic applications are exemplified below, while specific formulations for enhanced delivery of various drugs are provided in the section entitled "Enhanced Drug Delivery".

| DRY COSMETIC MASK WITH *CALENDULA* AND ST. JOHNS WART | |
|---|---|
| Component | Amount (g/100 g, % w/w) |
| Hyaluronidase | 0.10 (200 IU) |
| Magnesium oxide | 39.46-39.49 |
| White or blue clay | 14.98 |
| Talcum | 10.25 |
| Starch | 13.9 |

DRY COSMETIC MASK WITH CALENDULA AND ST. JOHNS WART

| Component | Amount (g/100 g, % w/w) |
|---|---|
| Aluminum potassium sulfate | 1.27 |
| Powder of *calendula* flowers | 10.0 |
| St. Johns Wart powder | 10.0 |
| Aromatizer (e.g. rose, lemon, peach) | 0.02-0.05 |

DRY COSMETIC MASK WITH COLORLESS HENNA

| Component | Amount (g/100 g, % w/w) |
|---|---|
| Hyaluronidase | 0.10 (200 IU) |
| Magnesuim oxide | 39.46-39.49 |
| Clay (white or blue) | 14.98 |
| Talcum | 10.25 |
| Starch | 13.9 |
| Aluminum Potassium sulfate | 1.27 |
| Henna (colorless) | 20.0 |
| Aromatizer (e.g., rose, lemon, peach) | 0.02-0.05 |

DRY COSMETIC MASK WITH SULFUR

| Component | Amount (g/100 g, % w/w) |
|---|---|
| Hyaluronidase | 0.10 (200 IU) |
| Magnesium oxide | 46.6-46.7 |
| Clay (white or blue) | 17.75 |
| Talcum | 12.15 |
| Starch | 16.5 |
| Aluminum potassium sulfate | 1.5 |
| Camphor | 2.4 |
| Sulfur | 2.8 |
| Aromatizer (e.g., rose, lemon, peach) | 0.1-0.2 |

COSMETIC CREAM

| Component | Amount (g/100 g, % w/w) |
|---|---|
| Hyaluronidase | 0.1-0.3 (200-600 IU) |
| Cosmetic stearic acid | 1.0-3.0 |
| Wax emulsion | 1.0-3.0 |
| Vegetable oil | 3.0-10.0 |
| Glycerin distilled | 3.0-8.0 |
| Glycerin monostearate | 1.5-5.0 |
| Triethanolamine | 0.1-0.3 |
| Chestnut extract | 1.0-4.0 |
| Nettles extract | 1.0-2.0 |
| Ethylparaben | 0.1-0.3 |
| Propylparaben | 0.02-1.0 |
| Aromatizer (e.g. Lemon) | 0.02-0.05 |
| Water | Up to 100.0 |

AROUND-EYE CREAM/GEL

| Component | Amount (g/100 g, % w/w) |
|---|---|
| Hyaluronidase | 0.05-0.2 |
| Eumulgin B-2 | 0.5-0.3 |
| Stearic acid | 0.5-5.0 |
| Glycerin monostearate | 1.0-5.0 |
| High molecular alcohol | 0.3-3.0 |
| Vegetable oil deodorized | 3.0-12.0 |
| Cetyol glyceril cocoate | 0.5-3.0 |
| Carbonol | 0.2-1.0 |
| Glycerin distilled | 3.0-6.0 |
| Ethylparaben | 0.2-0.5 |
| Bevantolol | 0.02-0.1 |
| Yeast extract | 0.3-1.0 |
| Triethanolamine | 1.0-3.0 |
| Food dye (e.g. .Ponceua E 124) | 0.001-0.005 |
| Aromatizer | 0.2-0.5 |
| Water | Up to 100.0 |

MOISTURIZING CREAM

| Component | Amount (g/100 g, % w/w) |
|---|---|
| Cosmetic stearic acid | 2.0 |
| Wax emulgated | 2.0 |
| Glycerin monostearate | 4.0 |
| Vegetable oil deodorized | 7.0 |
| Glycerin distilled | 5.0 |
| Triethanolamine | 0.2 |
| Wheat germ oil | 1.0 |
| Wheat germ extract | 3.0 |
| Hyaluronidase | 0.2 |
| Ethylparaben | 0.3 |
| Propylparaben | 0.1 |
| Aromatizer "Fruit mix" | 0.2 |
| Water | Up to 100.0 |

Wheat germ oil can substituted with Jojoba oil (1%)

Administration

Topical administration of hyaluronidase can be accomplished by ointments, creams, bandages, gauze, pads, transdermal patches, by electrophoresis, and as intra-vaginal tampons. The amount of the thug applied depends upon the type of skin lesion or damage. When applied topically, about 1 to 1000 IU, preferably about 50 to 500 IU, more preferably about 100 to 400 IU, and, most preferably, a total of 300±60 IU, can be applied. Alternatively, a surface concentration of about 1-200 IU, about 10-100, or about 20-60 IU of hyaluronidase/cm$^2$ can be used for topical administration. If necessary and considered advantageous for the patient, the dose can be increased up to 4-8 times. A weak allergenic activity of the preparation at elevated doses may be observed, hut, in general, the hyaluronidase has a low allergenic activity as compared to testicular hyaluronidase preparations such as Ronidase, as well as Solzyme and amylase. Guidance as to particular hyaluronidase dosages and methods of delivery is provided in the literature (for example, in State Pharmacopoeia of Russia, XI edition, Moscow, Publishing house Medicine, vols 1-2, 1987-1989).

For electrophoretic applications, 300 IU hyaluronidase can be dissolved in 60 ml of distilled water with 2-3 drops of 0.1 N hydrochloric acid. The preparation is then delivered by anodic current over the selected area for 20-30 min. The course of the treatment can be, e.g., 15-20 sessions. Electrophoretic application can also be alternated with compresses or a bandage.

When administering hyaluronidase via compresses, gauze, or other dermal applicators, a hyaluronidase solution can be applied onto a suitable applicator, e.g., 5-6 layer gauze. The gauze should cover the damaged area, and itself be covered with waxed paper and fixed with a bandage. The amount of applied preparation depends upon the area of damage and usually is 20-60 IU/cm$^2$, in average about 300 IU per compress. Bandages should be applied daily for about 16-18 hours for about 15-60 days. During a long course of treatment, it is recommended to stop the treatment every two weeks to make a break for 3-4 days. Compresses can be alternated with electrophoresis, but the prepared solution should be used within 24 hours. To be administered via a bandage, the content of the vial is dissolved in 5-10 ml of sterile saline or distilled water. The sterile 4-5 layers gauze is dampened with the solution and gauze is applied onto the damaged area, covered with wax paper and fixed with the soft bandage. The bandage can be applied daily for 15-18 hours during 15-60 days with a break for 3-4 days every 2 weeks.

For intravaginal application, the content of one vial (300±60 IU) can be dissolved in about 5-10 ml of sterile saline. A sterile tampon can then he dampened with this solution and inserted into the vagina daily for 5-6 hours for about 10-14 days.

For abdominal-lumbar-sacral electrophoresis the content of a 300 IU vial can be dissolved in 30-60 ml of distilled water and two to three drops of 0.1 N solution of hydrochloric acid added. The drug can then be administered by anodal current to the damaged surface for to 20-30 minutes. The course of treatment can be 15-20 sessions. Electrophoresis can also be conducted by using sinusoidal modulated current (at a frequency of 100 Hz and modulation of 100%). The course of treatment with electrophoresis can be about 15-20 sessions, or according to physician's recommendations. Methods and devices for transdermal electrotransport are well known in the art, see, e.g., U.S. Pat. Nos. 6,219,576; 6,181,963; 5,668,170; 5,464,170; and 5,203,768.

Various transdermal delivery systems based on patches are known in the art, and can be used in accordance of the invention for delivery of hyaluronidase alone or in conjunction with another active agent. Exemplary transdermal delivery systems are described, e.g., in U.S. Pat. Nos. 5,120,546, 5,203,768, 6,230,051, and 6,231,886. For example, transdermal dosage forms used in accordance with the invention preferably include a hacking layer made of pharmaceutically acceptable material which is impermeable to any active substance contained therein. The backing layer preferably serves as a protective cover for the active agent and may also provide a support function. Examples of materials suitable for making the backing layer are films of high and low density polyethylene, polypropylene, polyvinylchloride, polyurethane, polyesters such as poly(ethylene phthalate), metal foils, metal foil laminates of such suitable polymer films, textile fabrics, if the components of the reservoir cannot penetrate the fabric due to their physical properties and the like. Preferably, the materials used for the backing layer are laminates of such polymer films with a metal foil such as aluminum foil. The backing layer can be any appropriate thickness which will provide the desired protective and support functions. A suitable thickness will be from about 10 to about 200 in microns. Desirable materials and thickness will be apparent to the skilled artisan.

In certain preferred embodiments, the transdermal dosage forms used in accordance with the invention contain a polymer matrix layer. Generally, the polymers used to form the biologically acceptable polymer matrix are those capable of forming thin walls or coatings through which pharmaceuticals can pass at a controlled rate. A non-limiting list of exemplary materials for inclusion in the polymer matrix includes polyethylene, polypropylene, ethylene/propylene copolymers, ethylene/ethylacrylate copolymers, ethylenevinyl acetate copolymers, silicones, rubber, rubber-like synthetic homo-, co- or block polymers, polyacrylic esters and the copolymers thereof, polyurethanes, polyisobutylene, chlorinated polyethylene, polyvinyl-chloride, vinyl chloride-vinyl acetate copolymer, polymethacrylate polymer (hydrogel), poly vinylidene chloride, poly(ethylene terephthalate), ethylene-vinyl alcohol copolymer, ethylene-vinyloxyethanol copolymer, silicones including silicone copolymers such as polysiloxane-polymethacrylate copolymers, cellulose polymers (e.g., ethyl cellulose, and cellulose esters), polycarbonates, polytetrafluoroethylene and mixtures thereof.

Preferred materials for inclusion in the polymer matrix layer are silicone elastomers of the general polydimethylsiloxane structures, (e.g., silicone polymers). Preferred silicone polymers cross-link and are pharmaceutically acceptable. Other preferred materials for inclusion in the polymer matrix layer include: silicone polymers that are cross-linkable copolymers having dimethyl and/or dimethylvinyl siloxane units which can be crosslinked using a suitable peroxide catalyst. Also preferred are those polymers consisting of block copolymers based on styrene and 1,3-dienes (particularly linear styrene-isoprene-block copolymers of styrene-butadiene-block copolymers), polyisobutylenes, polymers based on acrylate and/or methacrylate.

An exemplary transdermal delivery system or "patch" for delivery of drugs such as, e.g., steroids such as hydrocortisone, birth control hormones, estradiol, comprises a polyethylene film, an acrylate adhesive matrix, a selected drug, the hyaluronidase of the invention, an acrylate copolymer adhesive, and suitable fatty acid esters.

Therapeutic and Cosmetic Applications

As described herein, treatment with the hyaluronidase preparation of the invention can be beneficial in therapy, surgery, dermatology, plastic surgery and gynecology for the treatment of sears and adhesions of different origin, joints stiffness and contractures. The drug can be used for the treatment of osteoarthrosis, chronic tendovaginitis. Dupuytren's contractures, skin symptoms of scleroderma, soft tissues hematoma, chronic inflammatory processes and functional disturbances of female reproductive system (vaginal mucosa hyposecretion, insufficiency of vaginal walls elasticity etc.); also, hyaluronidase can be prescribed in pre- and post-surgery periods of different types (skin plastic, reconstructing-plastic surgery, reconstructive-plastic surgery on female reproductive organs etc.) to prevent scar formation. The hyaluronidase can also be used according to physician's prescription in therapy, surgery, dermatology, and gynecology for the treatment and prevention of scars, joint stiffness and contractures, scleroderma, and chronic inflammatory diseases of female reproductive organs etc. In addition, the hyaluronidase can be used for enhancing the distribution and uptake of a cosmetic agent.

As described in the Examples and summarized below, the hyaluronidase has undergone a number of clinical trials to establish its potential for skin treatment and other medical applications. Thus, in preferred embodiments, the enzyme of the invention is used facilitate the distribution of active agents or cosmetic agents in skin or connective tissue; to increase movements in joints; to ease pain in arthritis patients; or to prevent formation or reduce the appearance of scars.

Therapeutic and Cosmetic Applications of Hyaluronidase Alone

Topical application of the enzyme of the invention reduces wrinkles and scars of varied cause. For example, the hyaluronidase prevents the formation of large hypertrophic scars, diminishes and softens existing scars from trauma and burns. As component in plastic surgery to reduce the appearance of facial scars, the enzyme also leads to a significantly improved outcome of therapy. Furthermore, the enzyme of the invention can be used as a skin-softening agent for cosmetics, and as a cosmetic adjuvant for prevention of scars; including those usually caused by acne, trauma, and burns as well as keloid scars, and as an anti-wrinkling agent. Keloid scars or "keloids" are an overgrowth of scar tissue at the site of a skin injury. Keloids occur from such skin injuries as surgical incisions, traumatic wounds, vaccination sites, burns, chickenpox, acne, or even minor scratches. For reduction or treatment of scars, wrinkles, or coarse skin, the hyaluronidase can be administered by compresses and/or electrotransport, or by suitable transdermal patches, creams, ointments, etc.

For treating atrophic or hypertrophic keloid scar, the preparation can be delivered by electrophoresis. The course of treatment can be fifteen sessions of twenty minutes each. Electrophoresis is preferably applied every day. Evaluation of the efficiency of treatment can include changes of clinical data (infiltration, density, color, site of scars) and subjective data (painfulness under palpation, itch, pain, burning sensations). In such investigations, after the fifth sessions, all patients who suffered from keloid scars and had itching, burning and pain sensations reported disappearance of subjective sensations. Objective assessment concluded that scars had become less colored, less dense, practically non-painful under palpation. After 10 sessions of electrophoresis, scars had become pale, soft, flattened and painless under palpation. Area of keloid scars decreased up to 40% compared to area before treatment after course. No side-effects were observed. The clinical picture improved similarly in patients with hypertrophic scars. The effect was most pronounced in patients with hypertrophic face scars after acne. In patients with atrophic scars only slightly raised over face skin after $5^{th}$ procedure scars flattened, became soft and were at level with normal skin.

Hyaluronidase preparations have also been used in afterburn scars in the course of preparation for surgery, and as a part of conservative therapy. After-burn scars were located mostly on upper and lower extremities and developed in 1-12 month after healing of burns of II-IIIA and IIIA-B, (According to standard classifications of skin burns: I—skin redness; II—blisters; III—deep burns, no blisters; A—damage do not spread beyond derma, B—damage of underlying tissue; see, e.g., Merck manual, 2002 Merck & Co., Inc Whitehouse Station, N.J., USA.). After treatment, the scars had softened, pain and itch decreased, tissue mobility increased which helped free tissue move, for plastic surgery. During conservative therapy of hypertrophic after-burn scars, edema disappeared, pain decreased, and scars became pale. More pronounced therapeutic action was observed when compresses were alternated with electrophoresis. Posttraumatic scars were located on face, neck, upper and lower extremities and were 1-2 years old. After application of hyaluronidase preparation, the tension of tissue and pain decreased.

In addition, topical application of the hyaluronidase relieves discomfort from rheumatoid arthritis, scleroderma, and tendosynoviitis. It can also reduce Dupuytren's contractures (early stages), contractures, joint stiffness after inflammation or trauma accompanied by hematoma of soft tissues; and the distribution of a cytotoxic drug delivered to a tumor by, e.g., topical application on melanoma lesions, or by intratumoral injection into other types of tumors. Some of the positive effects experienced by patients after receiving treatment with topically applied hyaluronidase of the invention are summarized in Tables 1A and 1B below. A total of 264 patients suffering from various diseases or conditions were studied, and 256 (95%) of the patients reported positive effects from the treatment.

TABLE 1A

Positive Effects From Local External Application of the Hyaluronidase

| Disease/Condition | | No. Patients | Positive Effect (%) |
|---|---|---|---|
| Scars | Surgical | 48 | 100 |
| | Traumatic | 13 | 100 |
| | After Burns | 54 | 100 |
| | Non-specified | 50 | 100 |
| Rheumatoid arthritis and osteoarthritis with movement limitations | | 25 | 93 |
| Vertebral osteochondrosis | | 12 | 90 |
| Dupuitren contracture | | 23 | 91 |
| Tendovaginitis | | 14 | 90 |
| Scleroderma | | 25 | 92 |
| Overall | | 264 | 97.9 |

TABLE 1B

Positive Effects Resulting From Use of Hyaluronidase in Gynecological Practice
The hyaluronidase was applied topically on tampons

| Disease/Condition | No. Patients | Positive Effect (%) |
|---|---|---|
| Chronic inflammation, non-surgical treatment | 48 | 100 |
| Scar formation prophylactics in gynecological surgery | 51 | 98 |
| Scar treatment | 8 | 100 |

The toxicity and incidence of side effects of the enzyme preparation of the invention is low. Specific tests has demonstrated low toxicity and lack of allergic, cancerogenic, or teratogenic activity, and almost no side effects. A local allergic reaction can be observed (skin redness and itching), but all symptoms have been shown to disappear within 24 hours after discontinuation of treatment, without additional therapy. Although ultimately depending on the disease, condition, or application, the hyaluronidase often most favorably applied in early periods of a disease or condition as a part of a therapy (physical therapy, massage, anti-inflammatory and analgesic drugs etc.)

The hyaluronidase preparation can be delivered by electrophoresis as a part of the therapy of rheumatoid arthritis and chronic osteochondritis. In one study, using the angle of joint movements as parameter for evaluating therapeutic effect, movements increased by 17.2±1.5 (p<0.05) after therapy in joints to which the preparation was applied. In control joints, the symmetrical affected joint where the preparation was not applied, the angle of movement increased on average only by 7.1+0.5" (p<0.05).

Analgesic properties of the preparation were determined in a group of patients suffering from osteochondritis of vertebral column and secondary root syndrome. Group consisted of 12 patients, 5 men and 7 women. 63±11 years old. Duration of the disease was 2 years to 10 years. Preparation was delivered by electrophoresis or compress applied paravertebrally or along the major nerves path at the areas that were most painful wider palpation of vertebral column. Analgesic effect was evaluated by using original quantitative method for the determination of pain threshold. After most painful area was determined by palpation pain threshold was measured in this area by applying graded pressure with the standard probe. The force of pressure and area of the probe surface were recorded when clear pain sensation appeared. Pain threshold was expressed in kg/cm$^2$. Pain threshold was averaged for the area. Control was pain threshold before treatment. Pain threshold increased from 0.9±0.5 to 3.5±0.7 kg/cm$^2$ ($p<0.05$, $n=12$). Positive effect was observed in 10 out 12 patients.

In 14 patients with tendovaginitis of inflammatory or post-traumatic origin, the range of movement increased and inflammatory edema disappeared after applications of the compresses with hyaluronidase preparation. Results of application of preparation in cases of Dupuytren's contractures before and after surgery demonstrated that in initial stages of the disease treatment with preparation for only one course, i.e. 14 applications, softened scars of the palm aponeurosis along the ulnar edge of the palm. In Stages I-II of the disease, positive effects were observed after 2-3 courses of hyaluronidase application. Positive effects were observed in the treatment of scleroderma: decrease of edema and hardening of the skin. In patient with facial scars complete disappearance of the scars was observed after three courses within a year. Side-effects, such as hyperemia and rash, quickly disappeared after short break in the treatment course and were observed only in 2.9% cases (in 7 out of 241).

Also, in the treatment of fertility problems (e.g., egg impregnation, egg implantation, salpingitis etc.), suppositories containing hyaluronidase formulated with glycerides of saturated fatty acids or hydrogenated vegetable oils can be used. The hyaluronidase can also be applied in depigmenting compostions comprising purified water, glycerine, phenyl trimethicone, glyceryl stearate, cetyl alcohol, linoleic acid, hydrogenated letcitin, soybean oil, tocopherol (vitamin E), dimethicon, retinol, carbomer, and fragrance.

Enhanced Drug Delivery

The hyaluronidase can also be used to improve the uptake and/or the therapeutic efficacy of a drug or cosmetic agent. The co-administration of hyaluronidase leads to increased uptake or absorption of the drug, which can allow for a reduced amount of the drug or cosmetic agent needed to achieve the desired drug concentration or effect. In addition, the hyaluronidase can be used in a controlled-release formulation to provide a prolonged delivery of the drug and/or a continuous steady blood or tissue concentration.

For example, hydrocortisone-based drugs are widely used for the treatment of collagenosis, rheumatoid arthritis and arthritis of other origin, vertebral column diseases, musclo-skeletal system diseases, allergic diseases of skin, eyes, and bronchial asthma, and diseases of ear, throat, nose etc. In an animal experiment, the addition of hyaluronidase to a hydrocortisone ointment resulted in three times faster and 98% more effective penetration of hydrocortisone, as measured in blood serum, showing enhanced drug penetration and uptake.

To treat diabetes, insulin can be administered transdermally (through the skin) or transmucosally (through mucosa) together with hyaluronidase. For example, insulin can be formulated with the hyaluronidase in a transdermal patch comprising a polyethylene film, an acrylate adhesive matrix, an acrylate copolymer adhesive, and suitable fatty acid esters.

The hyaluronidase can also be used to enhance the delivery of antifungal medications. Preferably, the hyaluronidase and anti-fungal agent are formulated as an ointment or powder. For example, in an anti-fungal lotion, ciclopirox can be formulated with the hyaluronidase, purified water, cocamide, octyldodecanol, mineral oil, stearyl alcohol, cetyl alcohol, polysorbate, myristyl alcohol, sorbitan monostearate, and benzyl alcohol. Also, hyaluronidase can be formulated together with an agent such as terconazole in a vaginal suppository for treatment of deep yeast infection or in formulations comprising excipients such as glycerides of saturated fatty acids and hydrogenated vegetable oils.

In inflammatory conditions, the hyaluronidase can be used to facilitate transdermal or transmucosal penetration of antibiotics into a damaged area via local or systemic delivery. The hyaluronidase can be delivered in a cream comprising drugs such as polymyxin and bacitracin, together with benzyl alcohol cetomacrogol, cetyl alcohol, mineral oil, phenoxyethanol, purified water, stearyl alcohol, and xanthan gum. Alternatively, an antibiotic such as vibramycin can be delivered by a patch containing the hyaluronidase, a polyethylene film, an acrylate adhesive matrix, an acrylate copolymer adhesive, and fatty acid esters.

Some pathologies such as chronic skin inflammatory conditions are accompanied by capsule formation which renders drug penetration into the lesion difficult. In such conditions, hyaluronidase could be used to facilitate drug delivery through the capsule, using, e.g., an ointment comprising lincomycin hyaluronidase, benzyl alcohol, cetomaerogol, cetyl alcohol, mineral oil, phenoxyethanol, purified water, stearyl alcohol, and xanthan gum.

The local delivery of an anesthetic drug such as procaine or lidocaine can also be improved by formulation with hyaluronidase. For example, about 100 IU hyaluronidase can be added to a 4% solution of procaine.

The hyaluronidase can also be locally applied to enhance the delivery of drugs stimulating or suppressing hair growth. Exemplary formulations for stimulation of hair growth preferably employ substances such as elformithine in combination with the hyaluronidase, formulated in a cream with cet-eareth, cetearyl alcohol, dimethicone, glyceryl stearate, methylparaben, mineral oil, phenoxyethanol, propylparaben, stearyl alcohol, and water. A cream for stimulating hair growth may comprise minoxidil, the hyaluronidase, cet-eareth, cetearyl alcohol, dimethicone, glyceryl stearate, methylparaben, mineral oil, phenoxyethanol, propylparaben, stearyl alcohol, and water.

The hyaluronidase can also be applied in depigmenting compositions with hydroquinone in a cream containing purified water, glycerine, phenyl trimethicone, glyceryl stearate, cetyl alcohol, linoleic acid, hydrogenated lecitin, soybean oil, tocopherol (vitamin E), dimethicone, retinol (vitamin A), carbomer, and fragrance.

Another preferred use for the hyaluronidase is to improve the efficacy of anti-psoriatic drugs such as alclometasone. Preferably, a formulation comprising the hyaluronidase and aclomethasone is administered to the psoriatic lesion as an ointment comprising, e.g., propylene glycol, white petrolatum, cetearyl alcohol, glyceryl stearate, cetech, monobasic sodium phosphate, chlorocresol, and purified water. For patients suffering from itching, an ointment comprising hyaluronidase, hydrocortisone, propylene glycol, white petrolatum, cetearyl alcohol, glyceryl stearate, cetech, monobasic sodium phosphate, chlorocresol, and purified water can be administered to reduce the itching sensation.

Cancerous lesions or precancerous lesions can be treated with the formulations of the invention to increase the efficiency of drug penetration and distribution in the tumor or lesion. For example, cervical cancer patients can be intravaginally administered the hyaluronidase in a cytotoxic drug formulated in a tampon according to established methods in the art. In melanoma or non-melanoma skin cancer, as well as other tumors accessible by topical administration (e.g., certain oral and esophageal tumors), the efficacy of topical chemotherapy using, e.g., 5-fluorouracil, can be improved by adding hyaluronidase to the topical composition. Generally, in the case of solid tumors, the hyaluronidase and anti-tumor drug can also be administered by direct intratumoral injection.

Examples of practicing the invention are provided, and are understood to be exemplary only, and do not limit the scope of the invention or the appended claims.

EXAMPLE 1

Physical Properties and Activity

This Example describes the evaluation of the molecular weight ($M_r$) and isoelectric pH (pI) of the hyaluronidase, and the effect of selected salts on its activity.

Materials and Methods

The molecular weight of intact hyaluronidase was estimated by gel filtration chromatography, on a Biogel P-100 column (1 cm×50 cm), using 50 mM PBS, pH 6.5, as mobile phase at a flow rate of 10 ml/hr. The column was calibrated by applying a mixture of proteins of known molecular weight (including ribonuclease, alpha-chymotrypsin, egg albumin, and serum albumin) and noting the elution time for each protein. A calibration curve was then constructed by plotting the elution time of each calibration protein against, its molecular weight. A sample of *Streptomyces actinocidus* hyaluronidase (5 mg/ml) was then applied, and the elution time of the enzyme used to estimate the molecular weight from the calibration curve.

A sample of 10 mg microbial hyaluronidase was subjected to isoelectric focusing in a pH gradient ranging from pH 4 to pH 6. UV absorbance at 280 nm was measured over the gel, and samples taken from the areas showing absorbance to test for hyaluronidase activity (see below).

The effect of selected salts and reagents on enzyme activity was measured by testing hyaluronidase activity in the presence of $10^{-4}$, $10^{-3}$, and $10^{-2}$ M salt/compound (see below).

Results

The results of the gel-filtration experiment showed that the molecular mass ($M_r$) of the enzyme is about 41±1 kD (FIG. 2), and isoelectric focusing showed that the isoelectric pH of the enzyme is pH 4.4 (FIG. 3).

The results of the experiment investigating the effect of various compounds on the activity of the hyaluronidase is shown in Table 2. None of the salts studied activated the enzyme, i.e., increased activity.

The ions $Fe^{3+}$ and $Cu^{2+}$ inhibited activity of microbial hyaluronidase by 25% in a concentration of $10^{-3}$ M. At $10^{-2}$ M, these ions inhibited hyaluronidase activity by 65% and 56%, $Fe^{3+}$ and $Cu^{2+}$, respectively.

β-Mercaptoethanol at concentration of $10^{-2}$ M completely inhibited hyaluronidase, which suggests the presence of di-sulfate bonds in the enzyme. Since no other hyaluronidases have been reported to contain di-sulfide bonds, this is yet another indication of the unique properties of the hyaluronidase of the invention.

p-Chlormercurybenzoate (p-CMB) at a concentration of $10^{-2}$ M partially inhibited microbial hyaluronidase, probably due to degradation of the protein-carbohydrate complex and enzyme inactivation. To reveal possible sulfhydryl groups, the interaction of microbial hyaluronidase with $10^{-3}$ M p-CMB was studied. No significant increase in optical density at 250 nm was observed, which indicates a lack of free SH-groups in the molecule. Thus, p-CMB did not inactivate the hyaluronidase, which distinguishes this enzyme from, e.g., hyaluronidase from *Streptomyces hyalurolyticus*. Although it cannot be excluded that free SH-groups, inaccessible for p-CMB, are located within the protein globule, titration of microbial hyaluronidase with p-CMB in the presence of the denaturing agent sodium dodecylsulfate (SDS) did not reveal any "hidden" SH-groups.

Comparing the data obtained with literature, data on the properties of *actinomyces* hyaluronidases revealed some differences. $Mn^{2+}$ salt and p-CMB ($10^{-3}$-$10^{-4}$ M) did not affect the activity of microbial hyaluronidase. However, $Mn^{2+}$, $Hg^{2+}$ and p-CMB in these concentrations inhibit hyaluronidase derived from *Stm. Hyalurolyticus* (Ohya, Biochem Biophys Acta 1970; 198(1):607-609).

TABLE 2

Effects of Different Reagents and Metal Salts on the Activity of Microbial Hyaluronidase

| Reagent or salt | Hyaluronidase activity (%) Concentration (M) | | |
| --- | --- | --- | --- |
| | $10^{-4}$ | $10^{-3}$ | $10^{-2}$ |
| Control (no reagents) | 100 | 100 | 100 |
| KCl | 100 | 100 | 100 |
| NaCl | 100 | 100 | 100 |
| FeCl$_3$ | 100 | 85 | 35 |
| FeSO$_4$ | 100 | 100 | 100 |
| CuSO$_4$ | 100 | 85 | 44 |
| MnCl$_2$ | 100 | 100 | 100 |
| ZnSO$_4$ | 100 | 100 | 100 |
| AgNO$_3$ | 100 | 100 | 100 |
| LiSO$_4$ | 100 | 100 | 100 |
| CoCl$_2$ | 100 | 100 | 100 |
| CaCl$_2$ | 100 | 100 | 100 |
| para-Chloromercury-benzoate | 100 | 100 | 80 |
| Na$_3$N | 100 | 100 | 100 |
| EDTA | 100 | 100 | 95 |
| beta-Mercaptoethanol | 100 | 65 | 0 |
| I$_2$ | 2010 | 12 | 0 |

EXAMPLE 2

Basic Properties of Hyaluronidase Produced by *Streptomyces*

This Example describes evaluation of the purity of an preparation of the hyaluronidase, as well as the pH optimum, pH stability, temperature optimum, thermostability, substrate specificity, and end products of the hyaluronidase reaction.

Purity of Microbial Hyaluronidase

The homogeneity of the enzyme preparation was studied by electrophoresis. Hyaluronidase purified by the method set forth FIG. 1 contains about 11-13% of carbohydrates and about 10% w/w of uronic acids. Electrophoresis using a polyacrylamide gel revealed either one diffuse band surrounded by a diffuse halo, or several bands. This can be due to complexes forming between proteins and carbohydrates in the preparation. In addition, the presence of the uronic acid carbohydrates in the hyaluronidase preparation made it difficult to stain proteins with amido-black stain, since stained bands were diffuse even after amount of protein was increased to 800-1500 micrograms. Coumassie Blue, which is used for staining of glycoproteins, was a more efficient stain. Staining of hyaluronidase with this stain produced clear bands after placement of 80-150 micrograms of protein (FIG. 4A).

Next, the enzyme preparation was analyzed on a polyacrylamide gel in presence of sodium dodecylsulfate and beta-mercaptoethanol. Under these conditions, protein denatures and releases all complexes including complexes with carbohydrates. Staining of the gel with amido-black revealed a clear, single, protein band. (FIG. 4B).

The hyaluronidase preparation was also subjected to gel filtration chromatography on a Sephadex (G-100) column. The enzyme was eluted in one symmetrical peak.

Thus, the method used to prepare hyaluronidase yields a homogenous substance.

pH-Optimum of Hyaluronidase

The hyaluronidase activity was tested at different pH in the range 3.0-12.0. The optimumal pH for cleavage of hyaluronic acid by hyaluronidase was found to be about 6.5-7 (FIG. 5). This pH optimum differs from values reported for other hyaluronidases obtained from *Streptomyces*. e.g., the optimum pH for hyaluronidase obtained from *Stm. Hyalurolyticus* and *Stm. Koganeiensis* is 5.0 and 4.0, respectively.

FIG. 6 shows the dependency of enzyme activity (Ig (Vmax/V-I), i.e., the decimal logarithm (Lg) of the ratio between maximum velocity and experimental velocity) on pH. The apparent dissociation constants of ionigenic groups of the hyaluronidase active center equaled 5.2 and 7.8, pH1 and pK2, respectively. The value of pK1 is closest to the pK value of the glutamate carboxyl group (3.8-5.1). The ionogenic group of an active center with pK2 of 7.8 may be an alpha amino group of an amino acid such as alanine, valine, leucine or some other ammo acid (pK 7.6-8.4).

Enzyme stability can also be compromised by pH. The results showed, however, that the hyaluronidase had practically the same high stability in the pH range 5.0-11.0, since 92-100% of activity was preserved after 48 hour incubation period (FIG. 7).

Thermostability of Hyaluronidase

FIG. 8 shows enzyme activity as a function of reaction temperature. The data demonstrated that microbial hyaluronidase cleaves hyaluronic acid at maximum rate at a temperature of about 50-60° C., which is characteristic or hyaluronidases obtained from the *Streptomyces actinomyces* strain.

Studying the kinetics of thermoinactivation or thermostability at pH 6.5 incubated for various periods of time at various temperatures revealed that hyaluronidase remained stable in temperature limits from 20 to 60° C. (FIG. 9). Even after 48 hours at 60° C., 60% of activity was preserved. At 70° C. degrees, the enzyme was deactivated faster, as only 38% of the activity remained after about 12 hours.

Substrate Specificity of Hyaluronidase

A homogenous preparation of the hyaluronidase was used to study the substrate specificity of the enzyme. Enzyme activity on hyaluronic acid, chondroitin sulfate A, B, C and heparin was evaluated. It was found that the hyaluronidase was only active against hyaluronic acid (FIG. 10). This is typical for many other microbial hyaluronidases. Thus, microbial hyaluronidase has a narrow substrate specificity and cleaves only hyaluronic acid, which makes it different from testicular and some other bacterial hyaluronidases.

Potassium hyaluronate was used as a substrate to determine the kinetic constants of microbial hyaluronidase. To calculate an apparent Michaelis-Menten constant ($K_m$) and maximum velocity of substrate cleavage ($V_{max}$), the dependency of initial reaction velocity on substrate concentration at 37° C. and pH 6.5 was studied. FIG. 11 demonstrates that $K_m$ and $V_{max}$ for potassium hyaluronate were 1.1 mg/ml and 0.022 μmole of N-acetyl-D-glucosamine/min, respectively

End Products of Hyaluronidase Reaction

Hydrolysis of 100 mg of hyaluronic acid was achieved by incubation with 560 IU of hyaluronidase, pH 6.0, for 20 hrs at 37° C. After hydrolysis, the hydrolysis products were analyzed by gel filtration chromatography (Sephadex G-25 (2×88), buffer 0.2M NaCI). Elution profiles were established using absorption at. 232 nm and the Morgan-Elison reaction (Morgan W and Elison L, Biochem J 1943; 26:988; and Reissin J L, J Biol Chem 1955; 217:959-966)

As shown in FIG. 12, two oligosaccharide components were found to be end products of the reaction (peaks 4 and 5). By comparing the molecular mass of both peaks to standards (chitotetraose, raffinose, and N-acetyl-D-glucosamine), which were in agreement with the calculated values (11.50 and 760, 1137 and 758 g/mol, respectively), it was found that the end-products were hexa- and tetrasaccharides.

EXAMPLE 3

Hyaluronidase Testing

This Examples describes the testing and formulation of hyaluronidase produced by a *Streptomyces* strain, stabilized with mannite, and useful as a drug for external use. All reagents mentioned in herein are described in appropriate chapters of State Pharmacopoeia of Russia. XI edition, Moscow, Publishing House Medicine, volumes 1-2, 1987-1989.

Properties

The initial preparation of hyaluronidase had the following properties:

Description. White-cream to light brownish amorphous powder or porous substance packed as a tablet. Tablet crumbles when shaken. The substance has specific smell and is hygroscopic.

Solubility. The substance is soluble in water and isotonic solution of sodium chloride Pharmacopoeia XI, Volume 1, p. 175.

Authenticity. The substance has hyaluronidase activity (see Quantitative analysis: Hyaluronidase activity).

Transparency. A solution of 0.1 g of substance in 10 ml of water has to be comparable with standard solution III (Pharmacopoeia XI, iss, 1, p. 198). Two solutions are prepared: 0.5 g of hydrazine is dissolved in 50 ml of distilled water and 3 g of hexamethylenetetramine is dissolved in 30 ml of distilled water. Mixture of different volumes of these solutions creates series of transparency standards. The testing solution is compared against standards.

Color. A solution of 0.05 g of substance in 5 ml of water has to be comparable with standard solution #2b (Pharmacopoeia XI, iss. 1, p. 194). Standard color solutions are prepared by preparing series of mixture of the solutions of cobalt chloride, potassium dichromate, copper sulfate, iron chloride and sulfuric acid. The testing solution is compared against the scale of yellowish standard solutions pH. From 6.0 to 8.0 (0.1%, solution in water, potentiometric method, Pharmacopoeia XL iss, 1, p 113).

Desiccation mass loss. 0.1 g of substance (exact amount) is dried under 100-105° C. until constant mass. The mass loss should not be more than 8% (Pharmacopoeia XI, iss.1, p. 176).

Bacteriological purity. It is allowed that in 1 g of substance them will be no more than $10^3$ bacteria and no more than $10^2$ of mould or yeast fungi (Pharmacopoeia XL iss, 2, p. 209). The following bacteria: *Enterobacteriaceae*, *Pseudomonas aeruginosa* and *Staphylococcus aureua* are not allowed in non-sterile drugs. For bacterial growth contents of one vial is dissolved in 1 ml of sterile buffer solution (Pharmacopoeia XI, iss. 2, p. 209). Further analysis is performed as described in Pharmacopoeia XI, iss. 2, pp. 196-200, Chapter "Quantitative analysis for microorganisms"

Quantitative Analysis: Hyaluronidases Activity

One unit of hyaluronidase activity is defined as such amount of hyaluronate lyase which acting for 1 min on the 0.3% w/v solution of substrate (potassium hyaluronate or hyaluronic acid) at 37° C. and pH 6.5 will produce oligosaccharides in the amount equivalent to 1 μmol of N-acetyl-D-glucosamine (NAGA).

0.3 ml of 3% w/v substrate is placed in two test tubes. The tubes are placed in a thermostat for 5 min at 37° C. 0.3 ml of phosphate buffer (pH 6.5) is placed in the third tithe (control). 0.2 ml of 1% hyaluronidase solution is placed in test tubes 1, 2 and 3. The mixture is incubated for 15 min (exactly) in a thermostat at 37° C. After incubation, 0.2 ml of the solution of potassium tetraborate is added. The tubes are placed in boiling water for 3 min (exactly). Afterwards, the tubes are cooled to room temperature by placing them in cold water. After cooling, 3 ml of Erlich reagent (for detection of N-acetyl-D-glucosamine) is added to each tube. The tubes are placed in a thermostat for 20 min at 37° C. (the solution in the experimental tubes will become raspberry-pink and the solution in the control tube yellow).

The optical density is determined in experimental solutions by measuring absorbance in a spectrophotometer at a wavelength of 582 nm in a tray 1 cm thick. The control solution is used for comparison.

Hyaluronidase activity (A) is then calculated as a number of international milliunits of 1 mg of substance (IU/mg) and calculated according to the following formula:

$$A = \frac{D_1 \times F \times 2.5 \times 100}{T \times n}$$

where; $D_1$—average optical density of the experimental solutions obtained in two measurements; F—calibration coefficient, determined from the calibration curve; T—time of the reaction (min); n—amount of the substance (mg); 2.5—dilution coefficient; and 1000—conversion coefficient.

Hyaluronidase activity of 1 mg of the substance must not be less than 2 IU. Hyaluronidase activity in vials (X) is calculated according to the formula:

$$X = \frac{D_2 \times F \times 2.5 \times 1000 \times 10}{T}$$

where: $D_2$—average value of optical density of experimental solutions (solutions 3 and 4) obtained in two parallel measurements; F—calibration coefficient, determined from the calibration curve; T—time of the reaction (min); 10—volume of phosphate buffer; 1000—conversion coefficient.

The amount of the substance in each vial should not be not less than 240 IU and not more than 360 IU.

Calibration Graph 0.5 ml of the solution containing 0.09, 0.121, 0.181, 0.226, 0.258 and 0.301 μmol of NAGA in 1 ml, respectively is placed in the it tubes prepared as in Table 3.

TABLE 3

Preparation of NAGA standard solutions

| Initial NAGA (ml) | Phosphate buffer (ml) | NAGA (μmol/ml) |
|---|---|---|
| 1.0 | 5.0 | 0.301 |
| 1.0 | 6.0 | 0.258 |
| 1.0 | 7.0 | 0.226 |
| 0.5 | 4.5 | 0.181 |
| 0.5 | 7.0 | 0.121 |
| 0.5 | 9.5 | 0.090 |

0.2 ml of the solution of potassium tetraborate is placed in each tube. The tubes are placed in boiling water bath for 3 min (exactly) and cooled in cold water bath. In each cooled tube, 3.0 ml of Erlich reagent is added and the tubes are placed in thermostat for 20 min at 37° C. Raspberry-pink color appears. Optical density of the solutions is determined with spectrophotometer with wavelength of 582 nm in a tray 1 cm thick. Solution of Erlich reagent is used for comparison.

The graph is drawn by marking of ordinate, axis in optical density units and abscissa axis in amount of μmol of NAGA in 1 ml of the respective standard solution. The graph is built for each new batch of reagents. The coefficient (f) is determined from the calibration graph: amount of NAGA in μmol in 0.5 ml of reaction mixture, which corresponds to one unit, of optical density. For example, if 0.18 μmol of NAGA in 0.5 ml produces increase in optical density by 0.4 units, then F=0.18/0.4=0.45.

Solutions

Preparation of the 1% solution of the substance. 0.01 g (exact amount) is dissolved in 1.0 ml of phosphate buffer with pH 6.5, Freshly prepared solution should be used.

Preparation of the 0.3% substrate solution. 0.03 g of potassium hyaluronate or hyaluronic acid obtained from rooster crest is placed in the metric 25 ml retort and 10.0 ml of phosphate buffer with pH 6.5 is added and stirred by using magnet stirrer until completely dissolved. The solution can be used for 2 days if stored in a refrigerator.

Preparation of phosphate buffer pH 6.5.
a) 13.6 g potassium monophosphate is placed in 1 L metric retort and dissolved in 200.0 ml of water. Water is added until volume reach exactly 1 L (solution A).
b) 22.8 g of potassium biphosphate is placed in 1 L metric retort and dissolve in 200.0 ml of water. Water is added until volume each exactly 1 L (solution B).

c) 500.0 ml of solution A is placed in 1 L retort and about 300 ml of solution B is added to obtain pH 6.7 (as determined by potentiometry) (solution C).

d) 700 ml of solution C is placed in 1 L retort and 3.1 g of sodium chloride is added (chemically pure) and stirred until fully dissolved. The solution could be used within one month if stored in a refrigerator.

Preparation of potassium tetraborate solution. 24.7 g of boric acid is placed in 500 ml conical retort and 420 ml of water is added. While stirring with magnetic stirrer 11.2 g of potassium hydroxide is added (SS 24363-80) in 50.0 ml of water while stirring continues until boric acid is completely dissolved. The solution should be used within 1 month.

Preparation of the Erlich reagent. 2.0 g of p-(dimethylamino)benzaldehyde (pure) is placed in 1 l thermoresistant retort and 600.0 ml of 0.1M solution of acetic acid is added. Mixture is heated with electric plate until boiling and filter into 1 L conic retort placed in ice bath. Precipitate is filtered using vacuum filtration through the funnel using a filter and dried on air for 24 hours. 5 g of recrystallized p-(dimethylamino)benzaldehyde is placed in 50 ml metric retort with and dissolved in 25 ml of iced acetic acid, 6.25 ml of concentrated hydrochloric acid is added and volume is increased to 50 ml with iced acetic acid. The solution can be used within one month if stored in refrigerator. The working solution is prepared immediately before analysis by diluting the stock solution with glacial acetic acid in ratio 1 to 9.

Preparation of NAGA solution. Exactly 0.01 g of NAGA is placed in a metric retort with capacity 25 ml and dissolved with 10 ml of phosphate buffer and diluted with phosphate buffer solution to the volume of 25 ml. 1 ml of the solution contains 1.808 μmol of NAGA. The solution should be prepared immediately before use.

Specific Activity

In two test tubes, 1 ml of 0.1% solution of substance is placed and 0.9 ml of solution A is added. The tubes are placed in a thermostat for 10 mm 50° C. and cooled to room temperature. Then, 3 ml of solution C is added to each test tube, shaken and placed in thermostat for 10 min at. 50° C. In the control experiment carried out in parallel, water is used instead of substance solution. The optical density of the solutions analyzed is determined at a wavelength of 670 nm in tray 1 cm thick. The control solution is used as a comparison solution.

The amount of protein in milligrams of protein per milligram of substance (B) is calculated according to the formula:

$$B = \frac{D2 \times 6.38 \times K}{a}$$

where: $D_2$—average value of the optical density of analyzed solutions, obtained in two parallel measurements; a—concentration of the substance in mg/ml; 6.38—empirical parameter to recalculate amount of tyrosine in relation to amount of protein in substance; and K—coefficient as determined by using calibrating graph.

Calibration Graph 1 ml of standard solutions containing 0.01, 0.2, 0.03, 0.04, 0.05 mg of tyrosine, respectively, is placed in the test tubes prepared as in Table 4.

TABLE 4

Preparation of standard solutions of tyrosine

| Initial Tyrosine (ml) | 0.2 M HCl (ml) | Final Tyrosine (mg/ml) |
|---|---|---|
| 1.0 | 9.0 | 0.01 |
| 1.0 | 4.0 | 0.02 |
| 1.5 | 3.5 | 0.03 |
| 1.0 | 1.5 | 0.04 |
| 1.0 | 1.0 | 0.05 |

0.9 ml of reagent A is placed in each tube. The tubes are placed in a thermostat for 10 min at. 50° C. and cooled to room temperature. To the cooled tubes, 0.1 ml of reagent B is added and the tubes are left for 10 mm at room temperature. Then, 3 ml reagent C is added and the tubes shaken and placed in thermostat for 10 min at 50° C. In the parallel control experiment. 0.2 M solution hydrochloric acid is used instead of tyrosine solution. The optical density of the solutions is determined by spectrophotometry at a wavelength of 670 nm. The control solution is used as comparison solution.

The control graph is created by marking ordinate axis in optical density units and abscissa axis in amount of tyrosine in milligrams in 1 ml of the respective standard solution. A new graph is created for each new batch of reagents. From the graph, the coefficient K is determined, i.e., amount of tyrosine in mg in 1 ml of solution corresponding to one unit of optical density. For example, if 0.02 mg of tyrosine in 1 ml produces increase in optical density by 0.35 units, then K=0.02/0.35=0.58. The specific activity (SA), expressed in number of International Units per 1 mg of protein (IU/mg protein), is then calculated according to formula:

$$SA = A/B$$

where: A—hyaluronidase activity of the substance (IU/mg); B—amount of protein (mg of protein/mg of substance). The specific activity should not be less than 30 IU/g of protein.

Solutions

Preparation of 0.1% solution of substance. Exactly 0.05 g of substance is placed in 50 ml metric retort and dissolved with 20 ml of water and volume is increased to 50 ml. The solution is prepared daily.

Preparation of reagent A. 2.0 g of sodium tartrate and 100 g of sodium carbonate is placed in the metric 1 l retort, dissolved in 500 ml of 1 M solution of sodium hydroxide and increase volume with water to 1 l. The solution can be stored under room temperature and used within 3 month.

Preparation of reagent B. 2.0 g of sodium tartrate and 1.0 g of copper sulfate 5-$H_2O$ is placed in the metric 100 ml retort, dissolved in 10 ml of 1 M solution of sodium hydroxide and increase volume with water to 100 ml. The solution can be stored in refrigerator for 3 month.

Preparation of the reagent C. 50.0 g of sodium tungstenate tartrate and 12.5 g of sodium molibdenate 2-$H_2O$ is placed in the metric 1 l retort and dissolved in 350 ml of water by stirring, 25 ml of orthophosphoric acid (SS 6552-80) and 50 ml of hydrochloric acid concentrated are added and mixture is boiled with recurrent refrigerator for 10 hours. The solution is cooled to room temperature and 75 g of lithium sulfate, 25 ml of water and 5 drops of bromidium are added. Bromidium residues are distilled by heating the mixture without refrigerator under the hood for 20 min. The solution must be yellow. If the solution is green, the addition of bromidium must be repeated. The solution is then cooled to room temperature and placed in 500 ml metric retort. The volume is increased to 500 ml with water and the solution is filtered (stock solution). The solution can be stored in a dark vial in a refrigerator for three months. A working solution is prepared on the day of use by diluting stock solution with water in 1 to 15 ratio.

Preparation of the stock solution of tyrosine. Exactly 0.01 g of tyrosine is placed in 1.00 ml metric retort, dissolved in 20 ml of 0.21\4 solution of hydrochloric acid and the volume increased to 100 ml with 0.2 M solution of hydrochloric acid. 1 ml of solution contains 0.1 mg of tyrosine. The solution is prepared daily.

Preparation of 0.2 M solution of hydrochloric acid. 17 ml of concentrated hydrochloric acid (SS 3118-77, chemically pure) is placed in 1 l metric retort and the volume increased to 1 l with water.

Packaging. 10 vials manufactured of neutral glass, hermetically sealed with rubber stoppers and oppressed with aluminum caps according are placed together with data sheets in boxes manufactured from box cardboard (e.g., type chrome-ersatz). They should be stored in a dry place at room temperature. Storage period—1 year.

To the solution is added 1 M solution of sodium hydroxide and volume increased with water to 100 ml. The solution can be stored in refrigerator for 3 month.

Preparation of Phosphate Buffer pH 6.5, at 13.6 g potassium monophosphate is placed in 1 l metric retort dissolve in 200 ml of water and add water until volume will be 1 l exactly (solution A).

b) 22.8 g of potassium diphosphate is placed in it metric retort and dissolve in 200 ml of water and add water until volume will be 1 l exactly (solution B).

c) 500 ml of the solution A is placed in retort with the volume of 1 l and about 300 ml of solution B is added to obtain pH 6.7 (as determined by potentiometrty) solution C.

d) 700 ml of the solution C is placed in retort of 1 l and 3.1 g of sodium chloride is added. (chemically pure) and stir until fully dissolved. The solution should be used within a month if stored in refrigerator.

Preparation potassium tetraborate solution. 24.7 g of acidum boricum is placed in conical retort with the capacity 500 ml and 420 ml of water is added. While stirring with magnetic stirrer 11.2 g of potassium hydrorixide is added in 50 ml of water is added and continue stirring until bone acid is dissolved completely. The solution should be used within 1 month.

Preparation of Erlich reagent. 20 g of p-(dimethylamino) benzaldehyde (pure) is placed in thermoresistant retort of 1 l capacity, and 600 ml of 0.1M solution of acetic acid added. The mixture is heated on electric plate until boiling and filtered into conic retort with a capacity of 1 l, and placed in ice bath. The precipitate is filtrated using vacuum filtration through the funnel according and dried on air for 24 hours. 5 g of re-crystallized p-(dimethylamino)benzaldehyde is placed in a metric retort with capacity 50 ml and dissolved in 25 ml of glacial acetic acid, 6.25 ml of concentrated hydrochloric acid is added and the volume is increased to 50 ml with glacial acetic acid. The solution can be used during one month if stored in refrigerator. The working solution is prepared immediately before analysis by diluting the stock solution with iced acetic acid in a ratio of 1 to 9.

Preparation of NAGA solution. Exactly 0.0100 g of NAGA is placed in a metric retort, with a capacity of 25 ml, dissolved with 10 ml of phosphate buffer, and diluted with phosphate buffer solution to the volume of 25 ml. 1 ml of the solution contains 1.808 μmol NAGA. The solution is prepared immediately before use.

EXAMPLE 4

Pharmacokinetics of Microbial Hyaluronidase

This Example reports investigations on the pharmacokinetics of the enzyme of the invention. The hyaluronidase can be used as an original enzyme-based drug that contains as active substance microbial hyaluronidase produced by the *Streptomyces* strain and as a stabilization agent and filler, mannite. The pharmacokinetics of the *Streptomyces actinocidus* hyaluronidase (specific activity 3200-3400 IU/g) was compared with Ronidase (hyaluronidase from bovine testicles; activity 350 IU/g).

Animals and Experiments

The activity of microbial hyaluronidase and Ronidase was studied in the blood serum of 8 Chinchilla rabbits (body weight 3.5 kg) after single skin application of the drugs. Microbial hyaluronidase and Ronidase were administered in doses of 100 IU/kg and 1000 IU/kg. This doses exceed single therapeutic dose (5 IU/kg) recommended for clinical use 20 and 200 times, respectively. Drugs were applied on the undamaged skin area 4×10 cm and covered with sterile multilayer gauze. Blood for measurement of drug activity was sampled (ear vein) in 0.25, 0.5, 1, 2, 4, 6, 8, 10, 20, 24 hours. Pharmacokinetics of the hyaluronidase and Ronidase were also studied in 4 rabbits after daily applications of 100 mg/kg for 5 and 6 days. Blood was sampled after 0.5, 1, 2, 20, 22, and 24 hours after the 5th and $6^{th}$ applications. Studies of the enzyme activity in the blood plasma were also conducted in 4 mud. (20 g body weight) after intraperitoneal injection of 6400 IU/kg. Blood samples were obtained at 0.5, 1, and 2 hours after drug administration. Blood samples were centrifuged under 3000 rpm for 20 minutes. To control for the baseline activity of hyaluronidase in blood plasma, samples were taken from rabbits (14 samples), rats (12 samples) and mice (4 samples) before drug administration.

Method of Determining Enzyme Activity in Biological Fluids

A modified "well" method was used for determination of hyaluronidase activity in blood plasma. The method is based on the radial diffusion of the enzyme into agar, which contains potassium hyaluronate as a substrate. The activity of the enzyme is proportional to the logarithm of the diameter of clear zone surrounding the agar well, in which plasma samples with hyaluronidase is placed. Readings are made after precipitation of non-hydrolyzed potassium hyaluronate with cetylpiridchloride.

Description of the method. The base media contains 3% agar dissolved in 0.05 M potassium phosphate buffer (pH 6.5) with addition of 0.1% of sodium chloride and 0.02% of sodium azide. A solution of potassium hyaluronate (2 mg/ml) in 0.05 M potassium phosphate buffer is added to the melt at 60° C. base media to obtain a solution with 1 mg/ml potassium hyaluronate dissolved in 1.5% agar in 0.05 M potassium phosphate buffer. Melted media is placed in Petri dishes in the amount of 9.5 ml. After hardening 18-20 wells (2 mm in diameter) are cut in every dish.

Half a milliliter of experimental sample and hyaluronidase standard solution of (seven different concentrations) was placed in separate wells. Each experimental sample was placed in three wells and each concentration standard was placed in two wells.

Standard solutions of microbial hyaluronidase or Ronidase were prepared with animal blood plasma. A stock solution of 100 ug/ml (4 IU/ml) of active enzyme was diluted to concentrations a 20, 10, 5, 2.5, 1.25, 0.63, and 0.31 IU/ml.

Petri dishes with samples and standards were in at 37° C. degrees for 20 hours. After incubation, 10 ml of 10% cetylpiridinechloride solution in distilled water was added. Precipitation occurred within 10-20 minutes and clear zones of the enzyme diffusion appeared. They were measured with the precision up to the 0.1 trim using an imaging system, and the average diameter was calculated for each standard and sample.

Curves of the dependency of the logarithm of diameter of clear zone from the concentration of standard solutions of hyaluronidase were constructed. The concentrations of microbial hyaluronidase and Ronidase in experimental samples were determined using standard curves. The sensitivity of the method for the microbial hyaluronidase was 0.3 IU/ml, and for Ronidase 1.0 IU/ml. The method precision was ±3%.

Results

The pilot experiment in the test system used (pH 6.5, 20 hours incubation at 37° C.) did not reveal endogenous hyaluronidase activity in blood samples obtained from control animals (rabbits, rats, and mice). Microbial hyaluronidase and Ronidase, when added in known concentrations to blood plasma of control animals (rabbits, rats, mice) remained active at least for 24 hours when samples were stored in refrigerator at temperature of 4-5° C. During the period 0.5-2 hours after intraperitoneal administration in mice of microbial hyaluronidase in dose 2 g/kg (LD50), the activity of the enzyme in blood plasma was 17-5.4 IU/ml.

After a single application on to the undamaged skin in rabbits of microbial hyaluronidase or Ronidase, in doses that exceeded therapeutic doses by 20 and 200 times, no activity in the blood plasma was determined up to 24 hours application. However, in 24 hours after administration of the drugs, there was skin hyperemia at site of application, which was more pronounced after application of Ronidase. After multiple skin applications of microbial hyaluronidase and Ronidase in daily doses of 100 IU/kg, no activity of the drugs was observed after five or six days in blood plasma. More prolonged application of the drugs was interrupted due to significant skin inflammatory reaction at the application site. The reaction was more severe after application of Ronidase.

Conclusions

The activity of hyaluronidase can be determined in blood plasma after intraperitoneal administration of microbial hyaluronidase or Ronidase in mice. After single or multiple applications of microbial hyaluronidase or Ronidase onto undamaged skin in rabbits, no drug activity could be determined in blood plasma within 24 hours after the last application.

EXAMPLE 5

Experimental Studies on Pharmacokinetic and Pharmacological Activity of Ointment Containing of Hyaluronidase and Hydrocortisone For the muscle-joint problems, ointments based on corticosteroids are widely used, and use of the water soluble form of hydrocortisone significantly increases its bioavailability. An anhydrous form of testicular hyaluronidase (Ronidase) has been used in attempts to improve the penetration of the drug. However, water based ointments which contain testicular hyaluronidase with agents such as detergents or alcohol etc. are unstable, while ointments bases that contain vaseline, lanolin, polyvynilethanol, or cellulose derivatives (methyl cellulose, oxypropilcellulose etc.) do not provide the necessary water solubility.

Described in this example is the development of a hydrophilic ointment with hydrocortisone, which contains the microbial hyaluronidase. The healing effect of the ointment is based on the interaction of hydrocortisone and microbial hyaluronidase. Hydrocortisone acts as the anti-inflammatory and anti-allergic agent. The presence of microbial hyaluronidase in the ointment allows a significantly decreased concentration (if hormone needed compared to officinal ointments to obtain a comparable effect. Use of the hydrophilic base, in which *actinomyces* hyaluronidase is stable, provides high permeability for the hydrocortisone. In addition, a study of the effect of storage duration on the preservation of hydrocortisone dispersion in the ointment revealed that prolonged storage does not affect the properties of the dispersion.

Materials and Method

Ointments containing 0.5% of hydrocortisone and 10, 20 or 60 TU of microbial hyaluronidase were used in experiments. For comparison, officinal ointment containing 0.5% of hydrocortisone was used.

Study of pharmacokinetics. This study was performed in 14 male Chinchilla rabbits weighing 3.1-43 kg. Two g of ointment was evenly applied onto depilated area of skin (10×8 cm) on side and back of the body. Multiple blood samples were taken from the ear vein at 0.5, 1, 2, 4, 6, 8, 12, 24 and 48 hours after application of ointment. Blood was centrifuged for 20 min at 5000 rpm and plasma level of hydrocortisone was determined by HPLC (column Particeal ODS-2 (4.6×250) with flow of 1.5 ml/min and UV detection 254 nm). Standards of hydrocortisone (1, 5, and 10 ug/ml) were prepared using blood plasma with the correction for baseline level of hormone for each rabbit. Sensitivity of the method was 0.1 µg/kg with an error ±10% Statistical analysis was performed using ANOVA and Student's t-test.

Study of anti-inflammatory activity of the ointment in the model of acute inflammation. Acute edema with the prevalence of exudative component evoked by carrageenan was used as a model of acute inflammation. Experiments were carried out in male mice $F_1$/C57$BL_x$ CBA/weighing 20-25 g. Each group of mice consisted of 12-14 mice. Edema was induced in the left hind limb by subplantar injection of 0.05 ml 1% carrageen solution in water. Edema was measured by using plethysmometer to determine the limb volume by the amount of water displaced ($\Delta V$ in ml). Application (thorough rubbing) of ointments, control ointment, and placebo in the amount of 50 mg per limb surface was performed at 2, 4, and 6 hours after carragenan injection. Measurement of the limb volume with plethysmometer was done after 3, 5, and 7 hours after carrageen administration. Mice with carragenan injection but without treatment were used as a control. Student T-test was used to evaluate statistical differences, and means and standard errors of the mean (sem) calculated.

Study of the anti-inflammatory activity of the ointment in the model of chronic inflammation. Adjuvant inflammation in rats was used as a model of chronic inflammation. Experiments were carried out in 64 male Wistar rats weighing 150-200 g. Each group consisted of 10-15 animals. Adjuvant inflammation of the paw, which is known to produce arthritis, was triggered by the single injection of 0.2 ml of the complete Freund's adjuvant. Animals with medium severity inflammation were used in the experiments. Inflammation was monitored by the plethysmometry of the paw volume. Animals were weighted on day 12, 19 and 26 from the beginning of experiments. Starting from day 12 animals received daily application on the surface of both hind paws of the ointment studied or control ointment in the amount of 250 mg. Student's t-test was used for statistical analysis.

Evaluation therapeutic efficiency of the ointments in volunteers. A group of volunteers with rheumatoid arthritis of interphalanx joints participated in the double blind study. Ointments of different compositions coded from 1 to 4 were prescribed randomly. Ointments (1-2 g) were applied on the affected joints and lightly massaged in twice daily (in the morning and in the evening). The duration of treatment was 14 days. To evaluate the anti-inflammatory effect, the circumference of the proximal inter-phalanx joints and angle of movement of inter-phalanx and metacarpal joints were measured. For evaluation of analgetic effects grip tightness and joint index were determined. The following lab tests were also used: ESR, C-reactive protein, latex-test, and determination of alpha-2 globulin, gamma-globulin, blood bilirubin, glucose, urea, creatinine. ALT, AST and urine analysis. All tests were done before and after two weeks of the treatment. Student's t-test was used for statistical analysis.

Results

Pharmacokinetics. Table 5 presents data on the concentration of hydrocortisone. FIG. 13 presents kinetics of the hormone in two groups of rabbits: group 1 (control) received officinal ointment (0.5% Hydrocortisone ointment) and group (experiment) received experimental ointment (0.5% Hydrocortisone and 20 IU of microbial hyaluronidase).

In control group 1 maximum concentration of Hydrocortisone was achieved by 24 hours and experimental group 2 Hydrocortisone concentration reached maximum in 6 hours, while the initial level of the hormone was comparable (0.25+ 0.13 µg/ml and 0.22±0.08 µg/ml, respectively) In the control 80% of the dose was absorbed between hours 12 in 24 after application. In the experimental group 80% of the dose was absorbed between hours 4 and 6. By 28 hours plasma level of Hydrocortisone started to decrease and returned to the baseline level in 48 hours.

Results of the calculation of the parameters of pharmacokinetics of hydrocortisone in the blood plasma of rabbits (Table 6) demonstrate that pharmacokinetics both groups significantly differ in half-time life, and average retention time. In the control group concentration of Hydrocortisone in the first 12 hours after application did not increase significantly compare to baseline level: it increased subsequently by about 8 times at 24 hours, which was followed by the gradual decrease within next 4 hours. In the experimental group during the first 2 hours after application the increase of Hydrocortisone level in blood plasma was insignificant. Following was rapid increase by ~38 times and subsequent gradual return to the initial level by 24 hours. In each group there were large difference in pharmacokinetics between individual animals, which partially can be explained by difficulties in precise dosage of the ointment, and evenness of the absorption of the drug by the skin. Fast increase concentration of the hormone in experimental group most probably is due to facilitating action of microbial hyaluronidase.

Pharmacological Activity of the Ointment

Acute inflammation. Ointment demonstrated clear anti-inflammatory properties in the model of acute inflammation (Table 7). All three variants of the ointment with the different concentration of microbial hyaluronidase significantly decreased inflammatory edema compare to control. Therapeutic effect was observed within hour after application of the ointment or three hours after the administration of carrageen. All three variances of the ointment with microbial hyaluronidase relatively similarly decreased the volume of the paw. However, the dynamic of therapeutic effect of the ointment with 60 IU of microbial hyaluronidase demonstrated slower effect. Within several hours ointments with 10 and 20 IU of microbial hyaluronidase decreased paw volume by 40% in 56% (compare to control), respectively. At that time ointment with 60 IU of microbial hyaluronidase decreased volume by 34%. However, in 7 hours after carrageen injection volume decreased by 51% (FIG. 14). Activity of Officinal ointment (0.5% hydrocortisone Ointment) was significantly slower and less pronounced.

No side-effects were observed in these experiments.

Chronic inflammation. By day 12 after the adjuvant administration volume of right hind paws (where adjuvant injection was made) in animals of all groups increased by ~60-80% compared to the initial volume and volume. Volume of the left paw increased by ~10-25%. Starting from day 12 ointments were applied daily on the hind paw skin for 14 days.

Results are presented in Table 8. In experimental groups that received ointments with microbial hyaluronidase and in group that received officinal ointment further increase in paw volume was 3-10% and 4-17%, respectively. However, in group without treatment volume increase was 10-22%.

Pathomorphology

Arthritis without treatment. The shape of bones comprising joints was changed. Joint cavity were filled with proliferating hyperplastic synovial cells and infiltrated with multiple cellular elements of aseptic inflammation. Hyperplastic, often multilayer, synovial membrane with hypertrophied villii and fibrous deposits was visible in preserved parts of joint bursa. Growing of the synovial membrane occurred mostly by the hypertrophy of its fibrous part. Significant areas of hyperplastic areolar tissue were observed with rare inclusions of fat tissue. All three types of synovial lining exhibit cellular hypertrophy. Substantial growth of the fibrous of membrane was accompanied pronounced fibrosis of subsynovial tissues, where among, coarse collagen fibers were multiple fibroblasts and leukocytes. Large panni (up to 1.5 mm in diameter) were observed in subsynovial tissue and in hypodermis. Inside some of them there were masses of necroticized collagen, other were empty and represented cysts, surrounded by numerous fibroblasts, granulating and fibrous connective tissue reach in coarse collagen fibers. Dilated blood vessels surrounded by dense mononuclear infiltration were seen in the area of connective tissue fibrosis. Joint cartilage was preserved only in some areas of joint surface with loci of metaplasia. Near the bone edges the cartilage eroded and at these sites growth of highly collagenated connective, tissue was observed. This tissue fused with synovial lining. The border between modified cartilage and synovial lining was preserved. Increased amount of proliferated and hypertrophic tissue in the synovial bursa suggests development of arthrosis. Muscular tissue around the joint was atrophic. Fibrous modification involved hypodermis. Epidermis thinned to 1-2 layers with weak keratinization. Significant tissue vascularization was observed.

Arthritis treated with the control ointment. Bones of the joint were deformed. The joint cartilage was hypertrophied. Its primary structure was lost. There were layers of low differentiated cells with signs of low calcification. The border bone and cartilage was diffuse. Overall mass off cartilage tissue decreased. Sparse tissues of the cartilage and the bone jointed with areolar lining tissue. The latter occupied relatively small areas and had increased number of cellular elements. Tissue of the joint were vascularized and infiltrated with numerous mononuclear cells. In many areas of subsynovial fibrous growth diminished. However, areas of dense fibroplasia were still observed. The size of empty cysts that replaced panni detritus decreased. Rare panni still contained necroticized tissue. Overall joint cavity were clearer than in control group.

Arthritis treated with the hydrocortisone and hyaluronidase. Bones were deformed. Hyperplasia of joint cartilage was less expressed, then in animals, which received officinal hydrocortisone ointment. However, cartilage doesn't have normal structure and is represented by a multi-layer sheet. In some areas it became loose (as well as a bone) and grew into fibrous lining of the synovial sheet. Compared to control group, hyperplasia and fibroplasia of subsynovial and hypodermal tissues in most of the joint was much less. The large areas of proliferation of areolar tissue were observed. Mononuclear infiltration of joint tissue decreased. Walls of panni were thin and lacked dense concentric sheath. Granulation tissue subsynovial areas of hypodermis was clearly visible and there was some fat tissue. Hypertrophy of villii was observed only a occasionally. All proliferating tissues were well vascularized. The muscular tissue was somewhat atrophic. Skin had normal structure.

It can be concluded that experimental ointment with microbial hyaluronidase and officinal ointment decreased proliferation of mononuclear cells and fibroplasia of hyperplastic tissues in rats with arthritis. In both groups of rats synovial cavity increased in volume due to decrease in proliferation of synovial lining tissue in comparison with non-treated rats.

The intent with microbial hyaluronidase triggered, less intensive cartilage proliferation, more efficiently decreased panni volume, fibroplasia, and inflamed tissues vascularization than officinal ointment.

Therapeutic Efficiency of Hydrocortisone/Hyalurouidase Ointment in Volunteers

A group of 40 female patients, 40-70 years old, participated in the study. All patients suffered since 3-16 years from slowly progressing rheumatoid arthritis. Six patients had light inflammatory process, 39 patients had moderate inflammatory process, and 3 had severe inflammation. In all patients, the proximal inter-phalanx joints were involved. X-ray studies demonstrated that the damages corresponded to stages according to the Steinbroker classification (X-ray classification of joint damage due to arthritis).

The following ointments were used in the experiments:
1. Hydrocortisone (0.5%)+microbial hyaluronidase (20 IU/g)+base;
2. Hydrocortisone (1%)+microbial hyaluronidase (20 IU/g)+base:
3. Placebo (ointment base alone);
4. Hydrocortisone ointment (1% officinal)

Changes in the clinical data during treatment are presented in Table 9. Ointments 1 and 2 showed beneficial therapeutic effect. In these patients movements in damaged joints increased by 10°, grip tightness increased to 30 mmHg, joint index decreased by more than 2, and circumference of inter-phalanx joints decreased by 6 mm. Ointments 1 and 2 were equally efficient. All patients that were treated with these ointments noted marked improvements. Ointments 3 and 4 did not exert therapeutic activity.

During, treatment there were no cases of side effects. Lab tests did not change significantly (Table 10). Tests of kidney and liver functions and urine analysis were within norms (Table 11).

Conclusions

The pharmacokinetic study demonstrated that the bioavailability of the ointment, including microbial hyaluronidase was higher than the bioavailability of the officinal hydrocortisone ointment. The ointment with microbial hyaluronidase provided faster penetration through the skin and higher blood levels of hydrocortisone. Moreover, the results of the studies of specific activity of the ointment with hydrocortisone and microbial hyaluronidase in the model of acute inflammatory edema indicate a more powerful and fluster anti-inflammatory action when compared to the standard 0.5% hydrocortisone ointment. Also, administration of the ointment with hydrocortisone and microbial hyaluronidase in rats with chronic inflammation demonstrated that the ointment slows down the development of adjuvant arthritis. The study demonstrated that the ointment had clear anti-inflammatory and analgesic effects, improved functional indexes of the affected joints, and was recommended for the treatment of the patients with the arthritis as the symptomatic drug in combination with standard therapy.

TABLE 5

Concentration of hydrocortisone in blood plasma of rabbits at different time points after application of ointment with or without microbial hyaluronidase

| Time after application (hours) | Hydrocortisone concentration (µg/ml) | |
|---|---|---|
| | Ointment without hyaluronidase | Ointment with hydrocortisone |
| 0 | 0.25 ± 0.13 | 0.22 ± 0.08 |
| 0.5 | — | 0.48 ± 0.18 |
| 1 | 0.47 ± 0.16 | 0.77 ± 0.18 |
| 2 | — | 0.22 ± 0.14 |
| 4 | 0.26 ± 0.09 | 2.02 ± 1.17 |
| 6 | 0.23 ± 12 | 8.54 ± 8.29 |
| 8 | 0.12 ± 0.02 | 7.1 ± 3.49 |
| 12 | 0.66 ± 0.59 | 1.39 ± 0.39 |
| 24 | 2.07 ± 1.37 | 0.33 ± 0.12 |
| 28 | 0.002 ± 0.002 | 0.014 ± 0.002 |

TABLE 6

Pharmacokinetics of Hydrocortisone

| Parameters | Ointment with hyaluronidase | Ointment without hydrocortisone |
|---|---|---|
| Half life (hours) | 0.40 ± 0.01 | 2.37 ± 0.14* |
| Retention time (hours) | 17.0 ± 2.7 | 7.89 ± 0.56* |
| CI (ml/min) | 7.78 ± 7.42 | 3.78 ± 1.45 |
| V (l/hour) | 7.95 ± 5.58 | 1.79 ± 0.76 |
| AIS (ug hour/ml) | 21.4 ± 14.6 | 44.0 ± 14.3 |

*p < 0.01

TABLE 7

Changes in carrageen induced edema of hind paw after application of ointment with different concentrations of hyaluronidase

|  |  | Mean ± sem and Δ V % of hind paw volume changes compared to initial volume | | | |
|---|---|---|---|---|---|
| Group | Volume Δ | Initial | after 3 hrs | after 5 hrs | after 7 hrs |
| Control | V | 0.21 ± 0.01 | 0.41 ± 0.02 | 0.40 ± 0.02 | 0.32 ± 0.02 |
|  | % | 0 | 95 | 90 | 52 |
| 0.5% Hydrocortisone | V | 0.20 ± 0.01 | 0.31 ± 0.01 | 0.32 ± 0.02 | 0.26 ± 0.01 |
| 10 IU of hyaluronidase | % | 0 | 55 | 60 | 30 |
| Control | V | 0.17 ± 0.01 | 0.38 ± 0.02 | 0.34 ± 0.02 | 0.33 ± 0.02 |
|  | % | 0 | 124 | 100 | 88 |
| 0.5% Hydrocortisone | V | 0.19 ± 0.01 | 0.32 ± 0.02 | 0.30 ± 0.02 | 0.29 ± 0.01 |
| 20 IU of hyaluronidase | % | 0 | 68 | 58 | 55 |
| Control | V | 0.22 ± 0.01 | 0.38 ± 0.02 | 0.37 ± 0.02 | 0.38 ± 0.02 |
|  | % | 0 | 73 | 68 | 73 |
| 0.5% Hydrocortisone | V | 0.23 ± 0.01 | 0.32 ± 0.02 | 0.30 ± 0.01 | 0.28 ± 0.01 |
| 60 IU of hyaluronidase | % | 0 | 39 | 30 | 22 |
| 0.5% Hydrocrtisone | V | 0.22 ± 0.01 | 0.37 ± 0.01 | 0.33 ± 0.01 | 0.31 ± 0.04 |
|  | % | 0 | 68 | 50 | 41 |

TABLE 8

Effects of hydrocortisone and *actinomyces* hyaluronidase ointment compared to effects of hydrocortisone officinal ointment on adjuvant arthritis

| # | Day of experiment | Volume of right paw (ml) m + sem | Volume of left paw (ml) m + sem | Volume of hind paws (ml) m + sem |
|---|---|---|---|---|
| *Ointment with hydrocortisone and actinomyces hyaluronidase* | | | | |
| 1 | 0 | 1.63 + 0.16 | 1.64 + 0.14 | 1.64 + 0.16 |
| 2 | 12 | 2.58 + 0.18 | 1.95 + 0.21 | 2.26 + 0.25 |
|  |  | 100% | 100% | 100% |
| 3 | 19 | 2.6 + 0.23 | 1.93 + 0.22 | 2.27 + 0.19 |
|  |  | 101% | 99% | 100% |
| 4 | 26 | 2.84 + 0.19 | 2.0 + 0.18 | 2.42 + 0.23 |
|  |  | 110% | 103% | 107% |
| *Officinal ointment with hydrocortisone* | | | | |
| 1 | 0 | 1.6 + 0.17 | 1.55 + 0.21 | 1.57 + 0.20 |
| 2 | 12 | 2.54 + 0.28 | 1.68 + 0.23 | 2.11 + 0.25 |
|  |  | 100% | 100% | 100% |
| 3 | 19 | 2.52 + 0.21 | 1.85 + 0.19 | 2.19 + 0.24 |
|  |  | 99% | 108% | 104% |
| 4 | 26 | 2.65 + 0.37 | 1.97 + 0.23 | 2.31 + 0.41 |
|  |  | 104% | 117% | 109% |
| *Control* | | | | |
| 1 | 0 | 1.44 + 0.21 | 1.47 + 0.24 | 1.45 + 0.21 |
| 2 | 12 | 2.58 + 0.22 | 1.85 + 0.19 | 2.22 + 0.23 |
|  |  | 100% | 100% | 100% |
| 3 | 19 | 2.84 + 0.23 | 1.91 + 0.21 | 2.38 + 0.18 |
|  |  | 110% | 103% | 107% |
| 4 | 26 | 3.16 + 0.19 | 2.18 + 0.26 | 2.67 + 0.31 |
|  |  | 122%* | 118% | 120% |

*p < 0.05

TABLE 9

Dynamics of symptoms in rheumatoid arthritis patients treated with different ointments (see text)

| Symptom | Ointment #1 (n = 15) | | Ointment #2 (n = 15) | | Ointment #3 (n = 8) | | Ointment #4 (n = 10) | |
|---|---|---|---|---|---|---|---|---|
|  | before | after | before | after | before | after | before | after |
| Mobility of metcarpal joints (degrees) | 60.9 + 4.8 | 70.9 + 5.0* | 52.9 + 4.3 | 70.7 + 3.1* | 59.3 + 4.7 | 59.5 + 5.1 | 53.2 + 6.4 | 53.7 + 5.0 |
| Mobility of interphalanx joints (degree) | 80.3 + 4.7 | 87.7 + 4.0 | 87.5 + 3.6 | 90.5 + 3.4 | 83.2 + 6.2 | 82.0 + 4.9 | 67.7 + 6.6 | 68.1 + 6.5 |
| Circumference of interphalanx joints (mm) | 269 + 7.2 | 263 + 6.1 | 278 + 6.4 | 272 + 5.0 | 273 + 6.4 | 272 + 6.4 | 278 + 5.3 | 278 + 7.7 |
| Joint index score | 4.4 + 0.9 | 2.0 + 0.5* | 5.7 + 1.0 | 3.8 + 0.9* | 3.0 + 0.4 | 5.3 + 1.2 | 6.2 + 1.3 | 6.0 + 1.1 |
| Grip force (mmHg) | 46.4 + 11.1 | 74.7 + 13.7 | 23.7 + 10.1 | 55.3 + 9.5* | 48.0 + 3.8 | 46.3 + 4.7 | 31.1 + 6.7 | 28.5 + 6.4 |

*p < 0.05

TABLE 10

Dynamics of laboratory data in rheumatoid arthritis patients treated with different ointments (see text)

|  | Ointment #1 (n = 15) | | Ointment #2 (n = 15) | | Ointment #3 (n = 8) | | Ointment #4 (n = 10) | |
| --- | --- | --- | --- | --- | --- | --- | --- | --- |
|  | before | after | before | after | before | after | before | after |
| Hb (mmol/l) | 125 + 5.8 | 123 + 6.1 | 122 + 3.8 | 124 + 3.6 | 124 + 3.2 | 125 + 3.2 | 125 + 6.3 | 123 + 4.5 |
| ESR (mm/hr) | 28.5 + 3.9 | 20.8 + 2.7 | 28.5 + 5.5 | 20.1 + 3.6 | 24.0 + 2.4 | 20.8 + 2.3 | 23.6 + 3.2 | 20.4 + 4.6 |
| Seromucoid (U) | 0.30 + 0.03 | 0.288 + 0.03 | 0.266 + 0.02 | 0.223 + 0.12 | 0.292 + 0.06 | 0.268 + 0.05 | 0.243 + 0.05 | 0.235 + 0.04 |
| CR protein | 1.2 + 0.25 | 1.0 + 0.23 | 0.7 + 0.2 | 0.5 + 0.1 | 1.0 + 0.2 | 0.8 + 0.1 | 0.8 + 0.1 | 0.6 + 0.1 |
| Rheum. Factor | 51 + 4.6 | 40 + 4.7 | 38 + 3.9 | 27 + 3.2 | 38 + 3.8 | 42 + 4.9 | 42 + 4.5 | 38 + 3.9 |
| Protein (mmol/l) | 80 + 1.6 | 78.6 + 1.1 | 86 + 1.9 | 88 + 1.3 | 87 + 3.5 | 84 + 2.8 | 84 + 1.6 | 87 + 1.5 |
| gamma$_2$-globulin (%) | 13.0 + 0.4 | 12.0 + 0.3 | 12.9 + 0.4 | 12.3 + 0.3 | 11.9 + 0.2 | 10.9 + 0.3 | 12.1 + 0.5 | 11.9 + 0.6 |
| gamma-globulin | 23.0 + 0.4 | 22.3 + 0.4 | 22.2 + 0.6 | 21.9 + 0.5 | 19.2 + 0.3 | 19.5 + 0.2 | 22.1 + 0.3 | 21.6 + 0.4 |

* p < 0.05

TABLE 11

Dynamics of lab data in rheumatoid arthritis patients treated with different ointments (see text)

|  | Ointment #1 (n = 15) | | Ointment #2 (n = 15) | | Ointment #3 (n = 8) | | Ointment #4 (n = 10) | |
| --- | --- | --- | --- | --- | --- | --- | --- | --- |
| Lab Test | before | after | before | after | before | after | before | after |
| Glucose (mmol/l) | 4.8 + 0.3 | 4.7 + 0.4 | 4.6 + 0.4 | 4.8 + 0.5 | 4.7 + 0.2 | 4.5 + 0.2 | 4.9 + 0.3 | 4.6 + 0.3 |
| Urea (mmol/l) | 5.5 + 0.7 | 4.9 + 0.4 | 4.7 + 0.4 | 4.5 + 0.3 | 8.6 + 0.5 | 8.2 + 0.4 | 5.3 + 0.6 | 5.2 + 0.4 |
| Creatinine (mmol/l) | 119 + 12 | 109 + 8.8 | 106 + 11 | 98 + 9.6 | 121 + 5.0 | 116 + 6.2 | 108 + 6.8 | 98.7 + 4.1 |
| Bilirubin (mmol/l) | 8.7 + 1.5 | 8.5 + 1.4 | 8.2 + 1.2 | 6.8 + 1.3 | 13.0 + 0.7 | 11.2 + 0.6 | 8.3 + 1.2 | 8.2 + 1.3 |
| ALT (Un) | 0.33 + 0.05 | 0.41 + 0.1 | 0.43 + 0.02 | 0.41 + 0.03 | 0.46 + 0.01 | 0.47 + 0.04 | 0.42 + 0.02 | 0.40 + 0.01 |
| AST (Un) | 0.51 + 0.02 | 0.50 + 0.03 | 0.46 + 0.04 | 0.47 + 0.02 | 0.61 + 0.02 | 0.49 + 0.03 | 0.48 + 0.02 | 0.46 + 0.01 |

* p < 0.05

EXAMPLE 6

In Vitro and In Vivo Studies of Microbial Hyaluronidase

This Example describes various in vitro and in vivo studies of a microbial hyaluronidase from *Streptomyces actinocidus*, such as the specific activity of the medicinal preparations in vitro, and physical and chemical properties of the drug. Lidase and Ronidase are two major hyaluronidase-containing drugs used clinical practice. Both substances are obtained from bovine testis. Lidase is a highly purified preparation of hyaluronidase used for parenteral administration, while Ronidase is a less purified preparation to be used externally. An alternative medicinal preparation of hyaluronidase has now been developed. The hyaluronidase used in preparation is produced by a *Streptomyces actinocidus* strain.

Specific Activity In Vitro and Physical and Chemical Properties

This section reports pharmacological and chemical properties of the hyaluronidase of microbial origin and Ronidase (hyaluronidase of animal origin). The study was performed to evaluate medical properties of microbial hyaluronidase in comparison with Ronidase. In the experiments, standards lots of Ronidase and microbial hyaluronidase were used. Chemically pure potassium hyaluronate, potassium tetraborate, n-(dimethylamino)-benzaldehide, N-acetyl-D-glucosamine and non-organic chemicals were used in chemical reactions.

Materials and Methods

Determination of hyaluronidase activity of preparations. Method based on the spectrophotometric measurement of the quantity of the products of substrate (potassium hyaluronate) hydrolysis by the hyaluronidase. For the measurement the following chemicals were used: 0.1M potassium phosphate buffer (pH 6.5), which contains 0.2 M sodium chloride; 0.8 M solution of sodium borate; Erlich's reagent, (prepared as follows: 10 g of n-(dimethylamino)-benzaldehyde was dissolved in the small amount of glacial acetic acid. 12.5 ml of concentrated hydrochloric acid was added, followed by additional glacial acetic acid until volume was 100 ml; and dilution of experimental reagent by concentrated acetic acid at 1:9 ratio before the experiment reagent was diluted): 0.2% potassium hyaluronate in 0.1 M potassium phosphate buffer (pH 6.5); and a standard solution of N-acetyl-D-glucosamine, 0.4% in 0.1 potassium phosphate buffer (pH 6.5) (1 ml of solution contains 1.82 uM N-acetyl-D-glucosamine).

To determine hyaluronidase activity, a sample of the drug was dissolved in 0.1M potassium phosphate buffer. Samples, witch contained 0.3 ml of the substrate solution and 0.2 ml of the drug solution (0.2 ml of buffer was used as control) were incubated at 37° C. for 15 minutes. Subsequently, 0.2 ml of the solution of potassium tetraborate was added to each sample. Samples were kept in a boiling bath for 3 min and cooled. Erlich's reagent (3 ml) was added to each sample. Samples were incubated at 37° C. for 20 min. The intensity of the raspberry color of the samples was directly proportional to the amount of the products of hydrolysis, which contain N-acetyl-D-glucosamine at the reducing terminal, Optical density of the samples was measured by spectrophotometry at 582 nm compared to control. Series of the dilutions of standard solution was processed similarly (starting twin the addition of sodium tetraborate). Calibrating curve was constructed for the dependency of sample optical density and the amount of the products of hyaluronic acid hydrolysis. The concentration of N-acetyl-D-glucosamine in experimental samples was determined by using this curve.

The activity of hyaluronidase was calculated according to the formula:

$$A = \frac{m \times d \times 2.5 \times 1000}{T \times n} IU/g$$

where: m—concentration of formed. N-acetyl-D-glucosamine in uM: D—dilution of the enzyme solution; T—reaction time in minutes; n—amount of the drug; 2.5—ratio of the volumes of reaction mixture and enzyme solution; 1000—coefficient of conversion into IU.

Determination of the drug solubility. Samples of the preparations were dissolved in a known volume of distilled water and stirred by magnetic stirrer at room temperature for 15 minutes. Sediment was separated by filtration. Filler with known initial weight was dried at 37° C. until weight stabilized. Weight of the substance, which remained in solution was calculated. Results were expressed in mg/ml of water.

Interaction of Ronidase and microbial hyaluronidase with hyaluronic acid at different conditions. In these experiments, potassium salt of hyaluronic acid was used instead of hyaluronic acid, which is a natural bio-substrate for hyaluronidases.

Results

The results of the activity determination are presented in Table 12,

TABLE 12

Activity of Microbial hyaluronidase and Ronidase sampled from different lots

| Enzyme | Lot | Enzyme activity, IU/g | |
|---|---|---|---|
| | | Indicated | Determined |
| Ronid Microbialase Enzyme | II | 2200 | 2154 ± 8 |
| | III | 2000 | 1957 ± 6 |
| | IV | 2600 | 2665 ± 14 |
| | V | 2400 | 2377 ± 11 |
| | 121286 | 300 | 254 ± 3 |
| | 020786 | 300 | 225 ± 5 |

The results demonstrated a close match between specified preparation data and experimental data. The specific activity of the microbial enzyme was about 8-10 times higher than that of Ronidase. Determination of the activity of both enzymes was performed at pH 6.5 (Ronidase displays maximum activity at pH 4.5). This was done to standardize conditions of drugs testing, and to use a pH closer to the normal physiological pH values at which the drugs will be used.

Determination of pH Optimum

This study was conducted in 0.1 M potassium phosphate buffer used to prepare solutions of substrate and enzymes. This butler system allows a pH interval from 4.5 to 8.5. The results are presented in Table 13.

TABLE 13

Influence of pH on Activity

| | Activity (IU/g) | |
|---|---|---|
| Media pH | Ronidase | Microbial Hyaluronidase |
| 4.5 | 355 ± 4 | 1575 ± 10 |
| 5.5 | 300 ± 4 | 2309 ± 9 |
| 6.5 | 245 ± 2 | 2665 ± 3 |
| 7.5 | 140 ± 8 | 2133 ± 7 |
| 8.5 | 95 ± 9 | 1184 ± 5 |

The pH optimum for the activity of Ronidase was equal or less then 4.5 (at lower pH it was impossible to determine hyaluronidase activity by this method). The pH optimum for the activity of microbial hyaluronidase was about 6.5 which is close to the physiological pH.

Determination of Temperature Optimum

Reaction mixtures were incubated at different temperatures (20-60° C.) under standard conditions. The results are presented in Table 14.

TABLE 14

Dependency of Specific Activity of Ronidase and Microbial Hyaluronidase on Media Temperature

| | Activity (IU/g of preparation) | |
|---|---|---|
| Temp (° C.) | Ronidase | Microbial Hyaluronidase |
| 30 | 140 ± 4 | 1566 ± 6 |
| 37 | 210 ± 2 | 2550 ± 7 |
| 45 | 225 ± 5 | 2908 ± 8 |
| 60 | 155 ± 3 | 3579 ± 11 |
| 75 | 35 ± 2 | 1210 ± 10 |

The activity of both enzymes was temperature dependent. The Ronidase activity was less dependent on temperature then the activity of *actinocidus* hyaluronidase. Ronidase showed maximum activity at 45° C., which is relatively close to normal conditions (37° C.).

The character of temperature dependency of *actinocidus* hyaluronidase closely resembled temperature properties of other enzymes of microbial origin with a temperature optimum at 60° C. At 37° C. about 70% of *actinocidus* hyaluronidase activity was preserved.

The decrease of activity of both enzymes at. 75° C. probably occurred due to gradual denaturation of the protein part of the enzyme molecule.

Stability

In a first series of experiments, the stability of the preparations solutions (i.e. the ability to maintain their activity) during prolonged exposure to room temperature was determined. Samples were dissolved in 0.1 M potassium phosphate buffer and initial activity was determined. Determination of activity was repeated after 24 and 48 hours. Results are presented in table 1.2.4 (a).

TABLE 15

Time-dependent Changes of Activity in Solution Stored at Room Temperature

| Time | Substance activity, IU/g | |
|---|---|---|
| | Ronidase | Microbial Hyaluronidase |
| Initial | 225 ± 5 | 2260 ± 6 |
| After 24 hours | 206 ± 3 | 1892 ± 12 |
| After 48 hours | 103 ± 8 | 1227 ± 10 |

The stability of the drugs in solution stored at room temperature was comparable. After 48 hours, the activity decreased by about 50%.

In a second series of experiments, the thermostability of the preparations was determined. Solutions were incubated at different temperature for 30 minutes. After incubation the specific activity of dissolved enzymes was measured. The results are presented in Table 16.

TABLE 16

Specific Activity after 30 Min. Incubation at Different Temperatures

| Incubation temperature | Solution activity, IU/g | |
|---|---|---|
| | Ronidase | Microbial hyaluronidase |
| Before incubation | 254 ± 3.5 | 21152 ± 8 |
| 50° C. | 197 ± 4 | 19453 ± 6 |
| 75° C. | 80 ± 5 | 584 ± 10.5 |
| 100° C. | 0 | 0 |

Increase of incubation temperature led to enzyme inactivation. After incubation at 75° C., the remaining activity was about 27-30%. All activity was lost after incubation at 100° C.

pH of Enzyme Solutions

Substances were dissolved in distilled water with an initial pH: of 6.2. Undissolved components were separated by filtration. Results are presented in Table 17.

TABLE 17 pH of Enzyme Solutions

| Enzyme Concentration (mg/ml) | Ronidase (pH) | Microbial Hyaluronidase (pH) |
|---|---|---|
| 1 | 6.2 | 7.9 |
| 5 | 6.3 | 8.0 |
| 10 | 6.3 | 8.1 |
| 25 | 6.35 | 8.2 |

Three different lots of each drug were studied. The pH of the solutions prepared from different lots was comparable (observed differences were within the method error). The pH only weakly depended upon the concentration of the drug. Solutions of Ronidase had weak acid reaction that is close to the pH of distilled water. Microbial hyaluronidase from *Streptomyces actinocidus* had an alkali reaction. The alkali reaction of the solution should therefore be taken into account when local skin reaction is evaluated after external application.

Solubility of Preparations

Three different lots of microbial hyaluronidase and Ronidase, respectively, were tested. Microbial hyaluronidase at a concentrations from 1 to 200 mg/ml when dissolved in distilled water or in 0.1 M potassium phosphate (pH 6.5) yielded yellow to dark brown solutions. High concentration solution was slightly opalescent and had fine non-precipitating colloidal suspension. Ronidase solutions contained non-soluble matter in distilled water or 0.1 M potassium phosphate buffer additives in the amount of 40-52% (by weight). These additives interfered with the measurements of enzyme activity (they produced erroneous readings during spectrophotometry). In experiments in animals, such components cannot be injected, so in all experiments the solid component had to be filtered. Indicated concentration of Ronidase used in the animal experiments (mg/ml) therefore refers to the initial amount of dry preparation. In experiments, only the liquid part remaining after filtration was used.

Effects of Enzymes on Isolated Organs and Tissues of Animal Origin

The objective of this part of the work was to compare interaction of Ronidase and *Streptomyces actinocidus* hyaluronidase with their natural substrate—hyaluronic acid as an element of animal tissue. For experiments, organs with natural high levels of hyaluronic acid were chosen: newborn umbilical cord, corpus vitreum of the eye, and skin (intended target of these drugs).

Materials and Methods

Umbilical cord of human newborn, rabbit eyeballs or corpus vitreum and rabbit skin were used in the experiments. All tissues were immediately after dissection.

Study of hydrolysis of biological tissue hyaluronic acid. Samples of tissues were dissected, weighted and placed in solutions of different concentration of enzymes in 0.1 M potassium phosphate buffer (pH 6.5) and 0.2 M sodium chloride and incubated at 37° C. The amount of corpus vitreum was expressed in ml.

After incubation, the samples of the reactive mixture were taken for analysis. The intensity of hydrolysis was estimated by the accumulation of N-acetyl-D-glucosamine NADG (the initial step of addition of enzyme to potassium hyaluronate was excluded). Results were expressed in uM of NADG per 1 ml of reactive mixture (ratio ((substrate mass)/(incubation media volume)) was constant).

Measurement of solutions cloudiness. Turbidimetry was used for quantification of the cloudiness of the solutions containing suspended particles. Results were expressed conventional optical units.

Determination of the mechanical properties of the biological tissues. Tensile strength of human umbilical cord and rabbit skin was measured. After washing with phosphate buffer umbilical cord was dissected in pieces 1 cm length and exposed to enzymes. After exposure samples were blotted dry and placed on hooks. One hook was fixed, second hook was connected to the dynamometer. Samples were pulled until rupture and force applied was recorded in kg.

In rabbits, two days before euthanasia, part of the skin was epilated with 10% solution of sodium sulfite. After euthanasia, epilated skin strips 1×2 cm were dissected. Along the sample midline prolonged cut was made. Two hooks were inserted through the cut and tensile strength was determined as described above.

Results

Umbilical cord studies. These experiments studied hydrolysis of umbilical cord hyaluronic acid by Ronidase and microbial hyaluronidase. Umbilical cord was washed with phosphate buffer (pH 6.5), dissected in samples about 0.5 grams each, and placed into the test tube with enzyme solution. Ten to 200 IU of preparations were added per each 1 mg of substrate in 1 ml of phosphate buffer per 100 mg of sample. Samples were incubated at 37° C. for 15 hours in shaker. At the end of incubation the amount of NADG in media was determined. The results are presented in Table 18.

TABLE 18

Amount of N-acetyl-D-glucosamine in the incubation media after application of hyaluronidase-containing drugs to umbilical cord samples.

| Enzyme amount (IU/mg substrate) | Concentration of NADG in incubation media (µM/milliliter) | |
|---|---|---|
| | Ronidase | Microbial hyaluronidase |
| 0.05 | 0.015 ± 0.006 | 0.020 ± 0.009 |
| 0.2 | 0.093 ± 0.014 | 0.086 ± 0.018 |
| 2 | 0.266 ± 0.013 | 0.210 ± 0.022 |
| 5 | 0.520 ± 0.028 | 0.479 ± 0.012 |

Hyaluronic acid of umbilical cord was similarly available for the activity of both preparations. To control for non-specific hydrolysis, similar experiments were performed after inactivation of enzymes by boiling for 30 min. NADG was not found after incubation with enzymes inactivated by boiling. It was observed that after incubation media became cloudy proportionally to the amount of enzyme added. To analyze changes in reactive mixture cloudiness samples were subjected turbidimetry.

Turbidimetry. This was measured of incubation media after administration of Ronidase and microbial hyaluronidase to umbilical cord tissue. After incubation the clear reactive media became clouded due to appearance of fine slightly opalescent suspension. The degree of media cloudiness was measured by photometry in two series of samples, which contained active enzyme drugs or enzymes inactivated by boiling in water-bath for 30 minutes (as control), respectively. Samples, which contained only substrate and phosphate buffer in the amount similar to experimental samples, were used as optical control. Results are presented in Table 19.

TABLE 19

Changes in the cloudiness of the incubating media after addition to the substrate (umbilical cord tissue) of the enzyme solutions

| Enzyme Concentration | Media cloudiness (optical units) | |
|---|---|---|
| | Ronidase | Microbial hyaluronidase |
| 0.05 | 0.350 ± 0.20 | 0.335 ± 0.50 |
| 0.2 | 0.530 ± 0.50 | 0.420 ± 0.35 |
| 2 | 0.745 ± 0.45 | 0.695 ± 0.20 |
| 5 | 0.1070 ± 0.30 | 0.865 ± 0.55 |

The cloudiness of the incubation media increased proportionally to the degree of substrate hydrolysis. Changes in cloudiness increase were comparable after application of Ronidase and microbial hyaluronidase. Degradation of hyaluronic acid of the umbilical cord under activity of the enzymes is probably accompanied by substrate tissue disintegration, which leads to appearance of small panicles in incubation media.

Mechanical Stability of Umbilical Cord after Enzyme Treatment

Damage to the tissue structure of the umbilical cord due to hydrolysis of hyaluronic acid may lead to changes in mechanical properties of the tissue. To evaluate effects of *Streptomyces actinocidus* hyaluronidase and Ronidase on the structural stability of the tissue the tensile strength of umbilical cord after exposure to enzymes was tested.

Umbilical cord was washed in phosphate buffer and 1 cm samples were dissected and weighted. Samples were placed into the test tubes with the solutions of Ronidase or microbial enzyme (1 ml of solution/100 milligrams of substrate). Phosphate buffer alone was used as control solution. Test tubes placed in shaker were incubated at 37° C. for 15 hours. After incubation samples were blotted dry and their tensile strength was measured. Results are presented in Table 20.

TABLE 20

Results of the determination of the mechanical stability of umbilical cord tissue after hyaluronidase application

| Enzyme concentration (IU/ml) | Maximum force at rupture (kg) | | |
|---|---|---|---|
| | Ronidase | Microbial Hyaluronidase | Phosphate buffer |
| 10 | 1.08 ± 0.808 | 1.06 ± 0.04 | 1.18 ± 0.09 |
| 20 | 0.86 ± 0.045* | 0.90 ± 0.05* | 1.26 ± 0.11 |

*p < 0.05

Application of the preparations at relatively high concentration decreased mechanical stability of the umbilical cord tissue by 25-30%. These concentrations exceeded by 400 times threshold concentration, at which NADG can be determined.

Effects of Enzymes on Isolated Eyeballs and Corpus Vitreum

Effects of enzymes on isolated eyeballs. Rabbit eyeballs were used in experiments. Weighted eyeballs were placed into the solution of Ronidase or microbial hyaluronidase, or phosphate buffer (which was used to dissolve drugs) in the amount of 1 ml of the solution/100 milligrams of substrate and incubated in shaker for 15 hours at 37° C. No traces of NADG (product of hyaluronic acid hydrolysis) were discovered in the media after incubation even when concentration of enzymes was 10 IU/ml. It was concluded that enzyme solutions do not penetrate into eyeball.

Effects on isolated comas vitreum of rabbit eyeball. Corpus vitreum almost completely consists of hyaluronic acid. Corpus vitreum was extracted from eye as a gel. Obtained gel was centrifuged and dissolved 10 times with phosphate buffer. Obtained solution was used as a substrate for enzyme reaction, which was performed similarly to determination of hyaluronidase activity as described earlier. Results are presented in Table 21.

TABLE 21

Content of N-acetyl-D-glucosamine in Incubation Media After Application of Enzymes to Corpus Vitreum of Eyeballs

| Enzyme concentration (IU/ml of diluted substrate) | Concentration of NADG in the incubation media, µM/ml | |
|---|---|---|
| | Ronidase | Microbial hyaluronidase |
| 0.05 | 0.040 ± 0.00 | 0.065 ± 0.008 |
| 0.2 | 0.125 ± 0.015 | 0.205 ± 0.006 |
| 2 | 0.86 ± 0.009 | 1.116 ± 0.012 |

Both drugs effectively hydrolyzed hyaluronic acid, which is a component of naturally occurring corpus vitreum of the eyeball.

Effects on Rabbit Skin

Epilated rabbit skin was dissected into samples 1×2 cm. Each sample was weighted, placed into the test tube and solution of Ronidase or microbial hyaluronidase (0.1-10 IU/ml) or phosphate buffer were added in the amount of 1 ml/100 milligrams of substrate. Samples were incubated for 15 hours at 37° C. degrees in shaker. Analysis of incubation media did not reveal products of the hydrolysis of hyaluronic ad (NADG).

Tensile strength of skin samples after incubation with either of enzymes (20 IU/100 mg of substrate) did not differ of samples incubated with phosphate buffer.

Specific Activity In Vivo

Experiments were carried out in non-strain rabbits of both sexes (body weight about 3 kg).

Materials and Methods

Measurement of skin blood vessels permeability. Skin was epilated with 10% of sodium sulfite. Intradermal injection of solutions of Ronidase or microbial hyaluronidase (0.2 ml) in epilated area was followed by i.v. injection of trypan blue (1% 2 ml/kg). Saline was injected intradermally in control rabbits. Blue staining of the skin at the intradermal injection site was monitored. Latency of staining appearance, intensity and size of the stained area were recorded.

After-burn scars (Model of experimental pathology). Evaluation of the tensile strength of scar tissue. Skin on the side of the body was epilated with 10% sodium sulfite. Under hexenal anesthesia (5%, 0.5 ml/kg) the limited burn damage was produced. Area of damage (IV degree burn) was about 32 cm$^2$. Star-like scars developed in 1.5-2 month in pace of burns. To evaluate tensile strength of sear tissue rabbits were euthanazied and scar tissue was dissected. Scar tissue was cut in strips 2×3 cm with the oriented along the long, axis. On both long sides triangular pieces were cut of in such way that middle part of the skin strip was 1 cm wide. Both ends, which were 2 cm wide, were fixed in clamps. Strips were stretched until rupture when force applied was recorded in kg.

Results

Effects of Ronidase and microbial hyaluronidase on skin vessels permeability. Changes in permeability of skin capillaries in areas of intradermal injections of enzymes were evaluated by appearance of blue staining of the skin following i.v. injection of Trypan blue, Latency of stain appearance, its intensity and size of the stained area are presented in table 12.

Administration of both enzymes increased skin vessels permeability in the site of injection. The permeability increase was comparable for both drugs and proportional to the concentration of administered solution. Slight tendency for increased permeability after administration of Ronidase compare to *actinocidus* hyaluronidase could be explained by presence of significant amount of additives in Ronidase.

Effects on Experimental Burn Scars

Skin scar tissue is rich in hyaluronic acid. The presence of hyaluronic acid in scars makes them firm and dense compare to normal skin. That brings about use of hyaluronidase containing preparations for the treatment of different scars, contractures or in preparation for skin surgery etc.

The model of burn scars in rabbits was used to evaluate specific activity of preparations. Rabbits with comparable scars (linearity, comparable sire and duration of healing) were selected for experiments. Preparations were injected into scars (intradermal injections, 0.2 ml/2 cm of scar length) three times within 7 days (every third day). Control animals received injections of saline. Before drugs administration skin around scars was epilated with sodium sulfite (10%). On the next day after last injection rabbits were euthanized and scars were dissected. Part of each sample was used to determine the tensile strength and the rest was studied hystologically. Results of the study of tensile strength of scar tissue are presented in Table 23.

TABLE 23

Tensile Strength of Scar Tissue After Repeated Injections of Hyaluronidase

| Preparation | Drug concentration | | Maximum force at rupture (kg) |
|---|---|---|---|
| | IU/ml | IU/cm of scar | |
| Microbial hyaluronidase | 200 | 40 | 1.7 ± 0.13 |
| | 50 | 10 | 1.9 ± 0.2 |
| Ronidase | 50 | 10 | 2.0 ± 0.16 |
| Saline | — | — | 2.1 ± 0.15 |

Light redness and weak edema were developed on the next day after injection. These changes were individual, did not depend upon the dose and disappeared in 1-2 days. After administration of saline in control animals these responses were not observed. There was tendency for decrease of scars strength after injection of the drugs (compare to control). This tendency was more pronounced when microbial hyaluronidase was used in concentration of 200 IU/ml. It was not feasible to administer Ronidase in similar concentration because of low solubility and a more significant inflammatory reaction at the injection site.

TABLE 22

Changes in Permeability of Skin Blood Vessels

| Drug | Drug concentration (IU/ml) | Latency of staining appearance | | Staining intensity | Area of stained zone (cm$^2$) |
|---|---|---|---|---|---|
| | | Weak staining | Intensive staining | | |
| Microbial hyaluronidase | 100 | 15 ± 1.8 | 55 ± 4.2 | ++++ | 9 ± 1.1 |
| | 50 | 28 ± 2.3 | 68 ± 8.5 | +++ | 6 ± 0.8 |
| | 20 | 45 ± 3.0 | 76 ± 3.6 | + | 4.5 ± 1.2 |
| Ronidase | 100 | 12 ± 2.2 | 46 ± 2.8 | ++++ | 9 ± 1.1 |
| | 50 | 20 ± 1.0 | 52 ± 5.7 | +++ | 6 ± 0.75 |
| | 20 | 370 ± 3.1 | 69 ± 2.7 | ++ | 3 ± 1.4 |
| Saline | — | — | — | 0 | 0 |

++++ dark blue staining; +++ blue staining; ++ light blue; + very light blue; 0 no staining.

The results demonstrated that both drugs had comparable activity in these models.

Effects on the Development of the Connective Tissue Capsule

Sterile glass plates (2.5×2.5 cm) were implanted under skin in male rats (body weight of 120-140 g) under anesthesia. In seven days after surgery rats were divided in three groups and drugs were administered into developing capsule surrounding glass plate. Drugs (in saline) were injected (0.5 ml) every other day. Each rat received 10 injections.

The first group (9 rats) received injections of saline; second group (10 rats) received injections of suspension of Ronidase; third group (10 rats) received injections of *actinocidus* hyaluronidase. Animals were euthanized after 10 injections, capsules surrounding, glass plates were dissected and studied histologically. Capsules in first group (saline, control) consisted of dense strands of collagen fibers brightly stained in red by saturn red and picric acid. Among strands there were mature fibroblasts with characteristic large oval light-colored nuclei, capillaries, hysticocytes in moderate amount. The thickness of the capsule was 200±40 um. Staining with Alcian blue for acidic glucosamine-glucans revealed light blue connective tissue fibers.

In animals of the second group (administration of Ronidase) capsules were thicker (360±90 um) and consisted of loosely positioned non-homogeneous strands of collagen fibers with large number of macrophages among them. Tinctorial properties of fibers differed from control: staining with saturn red and picric acid along, with the brightly stained areas revealed multiple unstained loci, fibers were disorganized and often fragmented and without clear borders. Staining with Alcian blue was also uneven and amplified in some areas. These changes can evidence for degeneration of collagen fibers.

In the third group, thickness of capsule was 280±40 um. The structure and tinctorial properties did not differ from those observed in control group.

Administration of Ronidase into connective tissue capsule around the glass implant in dose of 10 IU/kg led to disorganization of collagen fibers and transformation of basic substance of capsules by $27^{th}$ day of experiment. Microbial hyaluronidase in the same dose did not affect morphology of connective tissue capsules.

Differences in action of microbial hyaluronidase and Ronidase on the development of connective tissue capsules after administration of enzymes into developing capsule probably due to the fact that microbial and testicular hyaluronidases exert different effect on animal connective tissue. Testicular hyaluronidase besides hyaluronic acid also hydrolysis chondroitin sulfate C and some other substances. It i also possible that other enzymes, such as proteases, may be present in Ronidase. However, as described above, neither Ronidase nor microbial hyaluronidase affected isolated rabbit eyeballs.

Discussion

In this study two preparations of hyaluronidases of different origin—microbial and testicular—were compared. Study was done in order to evaluate the possibility to use hyaluronidase from *Streptomyces actinocidus* instead of Ronidase for external use.

It was observed that basic properties of microbial hyaluronidase have some advantages over properties of Ronidase. First: specific activity of microbial hyaluronidase is 10 times higher. That allows to use lower amounts of preparation. This can be seen in the in vivo experiments on the effects on the capillary permeability: specific activity of both drugs was comparable. However, concentration of solutions used in mg/ml for microbial hyaluronidase was 10 times less. Second, pH optimum for the activity of microbial hyaluronidase (6.5) is much closer to the physiological values then pH optimum for the activity of Ronidase (4.5). Third, Ronidase has significant amount of admixtures. Comparison of other properties (stability, dependency of the activity on temperature) of these drugs demonstrate some differences. However, these differences are of less importance.

In further experiments the activity of both preparations toward substrates reach in hyaluronic acid of animal origin was compared (umbilical cord of newborn human and corpus vitreum of rabbit eyeball). It was discovered that in comparable dosage of the drugs in units of activity microbial hyaluronidase and Ronidase hydrolyze hyaluronic acid of animal tissues with comparable speed. This conclusion is based on the results of measurement of products of the hyaluronic acid hydrolysis, incubation media cloudiness and tensile strength of biological tissues. When normal skin was used as a substrate which contains hyaluronic acid in small amounts the clear signs of the action of enzymes were not obvious. However, enzymes may be efficient in their action on pathological formations, such as after burn scars, which contain significant amount of hyaluronic acid.

This possibility was studied in experiments in vivo with the administration of the drugs into after burn skin scars in rabbits, Dosage of preparations used was determined by their activity in IU. Presence of hyaluronic acid in the connective tissue of the scar makes it dense and a stable. Application of hyaluronidase based drugs in this case is aimed two soften scar tissue, decrease its density and tension. In described experiments density of after-burn sears after administration of the drugs had tendency to decrease. This tendency increased with dose. This property was comparably expressed by both drugs. This results are an agreement with the literature data indicating that drugs with hyaluronidase activity have mild and individual therapeutic action and it is recommended to use them as a part of complex therapy in combination with other drugs and treatments to increase efficiency of the latter.

Conclusions

Hyaluronidase from *Streptomyces actinocidus* has a specific activity 10 times higher than Ronidase. When administered in similar doses (in IU), microbial hyaluronidase and Ronidase hydrolyze hyaluronic acid of human umbilical cord and rabbit corpus vitreum with comparable efficiency. Microbial hyaluronidase and Ronidase affect stability of after-burn scar and permeability of skin vessels in similar manners.

EXAMPLE 7

Experimental Study of the Toxicity of New Medicinal Preparation of Hyaluronidase This Example evaluates the toxicity of microbial hyaluronidase from *Streptomyces actinocidus* in comparison to Ronidase. Ronidase is available in vials containing 5 or 10 grams of the drug. Ronidase can be used for locally for the treatment of scars (after burn or surgery etc.), contractures, joint stiffness, in preparation for plastic surgery for scar removal, chrome tendovaginitis, slowly healing wounds. Ronidase powder is applied on the moist gauze, which is applied on the damaged area and covered with the waxed paper and fixed with bandage. Amount of ronidase for single application depends upon the size of damaged area in average 0.5-1.0 grains (150-300 IU). Drug is administered daily during the course of 15-30 days. In prolonged treatment breaks for 3-4 days are made every 2 weeks.

Acute Toxicity

Acute toxicity was studied in non-strain laboratory mice (18-20 g) and rats (100-120 g). Drugs dissolved in distilled water were injected intravenously or intraperitoneally. Each dose of the drugs was tested in six animals. Mice received drugs i.v. in volume of 0.5 ml at rate 0.1 ml/sec. Rats received drugs in volume of 1 ml/100 g of body weight. Animals were monitored for 14 days after injection.

Study of acme toxicity after i.v. administration in mice of the microbial hyaluronidase from 5 standard lots established $LD_{50}$ varied from 2740 mg/kg (lot 1/5) to 3167 mg/kg (Lot 5/2), and maximal tolerated dose was 1500-2000 mg/kg. Mice died within 3 days after i.v administration of the lethal dose of microbial hyaluronidase. Mice became adynamic, torpid, depressed. Death occurred from respiratory arrest. Mice that survived over the first three days did not die later. On the autopsy of died animals there were no visible changes of internal organs. $LD_{50}$ of *actinocidus* hyaluronidase in rats after intravenous administration was comparable to that observed in mice.

It was not possible to study effects of intravenous administration of Ronidase because of its low solubility in water. Due to that comparison of acute toxicity of microbial hyaluronidase and Ronidase was done by using intraperitoneal injection in mice. Suspension of Ronidase and solution of microbial hyaluronidase was prepared by with 0.5% solution of methylcellulose. Drugs were administered in volume of 0.5 ml per mouse.

Symptoms of acute toxicity after i.p. administration were similar to those observed after i.v. administration. However, after i.p. administration symptoms of intoxication developed slower. Usually death occurred in 2-3 days after drug administration, while after i.v, administration most animals died within first 24 hours. Autopsy of animals died after i.p injection of microbial hyaluronidase and Ronidase revealed dilation of peritoneal vessels and in some eases hyperemia of intestinal walls. Serous fluid was discovered in the abdominal cavity of some mice, which received i.p. administration of Ronidase. Data demonstrated that if measured in mg/kg both drugs had comparable toxicity. However, microbial hyaluronidase was 8 times less toxic then Ronidase when dose expressed in IU/kg. That might be explained by the fact that Ronidase contains some additives which have toxic activity.

Chronic Toxicity

Microbial hyaluronidase can be used for external applications by applying moist gauze with enzyme powder on the damaged area. That determined the choice of method of prolonged skin application to study chronic toxicity of the microbial hyaluronidase.

In chronic experiments in rabbits dose of 0.1 g per animal was used or in average 40 mg/kg (twice the dose used in clinic for Ronidase). The choice of dose was based on the fact that daily therapeutic dose of Ronidase is 1 g (about 15 mg/kg), which is applied for 15-60 days (with 2-3 days break after every 2 weeks). Skin applications of the drugs were performed daily for 62 days without breaks. More prolonged application of the microbial hyaluronidase or Ronidase was not sensible because no signs of resorption-triggered effects or signs of local imitation were observed during the whole duration of the experiment.

Experiments were conducted in 16 Chinchilla rabbits (2.16+0.13 kg) of both sexes. Six additional rabbits were used as control. Three days before the beginning of experiments area of the skin (10×7 cm) on back was epilated with 10% sodium sulfite after being shaved. During the whole experiment epilation was repeated two more times in rabbits, which were euthanized after 35 applications and four more times in rabbits that were euthanazied after 62 applications.

In the experimental groups the epilated skin area was moistened and drug powder was rubbed in for 5 min. Rubbing produced skin hyperemia and provided dose contact between drug and skin. In the first experimental group animals received applications of microbial hyaluronidase (0.1 g/animal, ~40 mg/kg) and in the second group animals received similar doses of Ronidase. In control group animals moistened skin area was rubbed for five minutes without powder. Three rabbits each group were euthanazied after 35 days of applications (in summary they received 3.5 g of the substances, on average 1550 milligrams per kg). Other rabbits were euthanazied after 62 days of the experiment (during the whole period they received application of 6.2 g of the drugs, on average 750 mg/kg).

Animals were daily examined to evaluate their overall state and status of the drug application site. Before the beginning of the experiment and every seven days afterwards rabbits were weighted. The following parameters were determined initially and measured four times during the experiment: blood hemoglobin, blood counts, urine analysis, residual blood nitrogen, bromsulphalein excretion, ALT and AST, blood coagulation, thromboelastogram, blood glucose. EKG.

At the end of the experiment animals were euthanazied and internal organs were weighted and histologically studied. Samples of liver, kidneys, spleen, heart, adrenals, and skin from applications site after fixation in 10% formalin were washed, sliced and stained with hematoxylin and eosin. Statistical analysis was performed by using Student's t-test.

Daily, for 62 days, applications of the microbial hyaluronidase and Ronidase on the epilated skin (70 cm$^2$) did not affect general status of animals. Rabbits that received administration of drugs by their appearance or behavior did not differ from control or intact animals during the whole experiment. During the whole duration of the experiment the skin, where drugs were applied, in 30-40 min after application restored normal appearance after rubbing-induced hyperemia. The only exclusion was rabbit #677 (application of Ronidase), in which from the third till seventh day of the experiment light hyperemia persisted for 6-8 hours after rubbing. During the period of experiment body weight of control rabbits increased by 640 grams and animals which received microbial hyaluronidase by 800 grams, and animals which received Ronidase by 630 grams.

Hemoglobin and blood, counts remained within normal limits during the whole experiment. Urine analysis did not reveal any differences between control and experimental animals. There were no significant differences and blood residual nitrogen. No changes were observed in blood plasma activity of AST and ALT, blood glucose, and bromsulphalein excretion. In the experimental animals there were no changes in EKG or in tromboelastograms. Relative weights of internal organs and the amount of fat in liver in control and experimental animals was comparable and within normal limits.

Macroscopic studies at autopsy of rabbits euthanazied after 35 days or 62 days of application of microbial hyaluronidase and Ronidase did not reveal any changes of skin, fur, visible mucosa. Fur was smooth, shiny, hair were well attached. Skin at application sites had normal thickness and elasticity.

Topography of the organs of chest and abdominal cavities was normal. Heart had regular configuration, dark-red myocardium was resilient. Liver had brown-red color, regular size and consistence. Kidneys were of grey-pink color. Fibrous capsule was readily detachable. On the cross-cut cortical and medullary layers were clearly visible with well-defined border between them. Spleen had dark wine-red color, normal consistence and resiliency.

Microscopically, skin of control and experimental animals had normal structure. Thin layer of epidermis consisted of 3-4 cell layers and relatively thin layer of squama. Condition of different layers of skin was not perturbed by the multiple applications of the microbial hyaluronidase and Ronidase. There were no signs of intensive squamous. Derma under epidermis had normal structure with hair follicles and skin glands. No pathological changes were observed in subdermal connective tissue. Relation between thickness of all skin layers was preserved.

In control animals and in rabbits that received applications of microbial hyaluronidase and Ronidase, there were no changes in the microscopical structure of internal organs. Myocardium was normal: muscular fibers had similar thickness and were evenly stained. Transverse striation was well expressed. Stroma-muscle relations were normal. In all animals, liver was without changes. Hepatocytes formed even bands converging to central veins. In some animals sinusoids were slightly dilated. In all animals peri vascular lymphoid infiltration was observed in the periphery of liver lobuli. The structure of the kidneys was regular and comparable in animals of all groups. The renal glomuli had even size, epithelium of convoluted tubules without dystrophy. In spleen, adrenals, lungs no changes were observed in all groups. It can be concluded that prolonged dermal application of *actinocidus* hyaluronidase or Ronidase does not produce any pathological changes of the skin or internal organs.

Effects on the Rabbit Eye

Application into conjuctival sac in rabbits of 2-3 drops of filtered 10% solution microbial hyaluronidase or 10% suspension of Ronidase 1 time a day for three weeks did not produce any signs of irritation or other side-effects.

Conclusion

The preparation of hyaluronidase of microbial origin (*Streptomyces actinocidus*) is a drug with low toxicity. $LD_{50}$ of the microbial hyaluronidase in mice after intravenous administration is 2914±92 mg/kg. Maximal tolerated dose of the microbial in mice after intravenous injection is 1500 mg/kg (3750 IU/kg) and exceeds 872 times the daily therapeutic dose of Ronidase (1 g/human-14.3 mg/kg or 4.3 IU/kg) and dose of microbial hyaluronidase recommended for Clinical trials (300 IU-4.3 IU per kg) for external application. Medicinal preparations of microbial hyaluronidase and Ronidase are equally toxic when injected intraperitoneally in same amount by weight. However, when dosage is expressed in IU/kg, microbial hyaluronidase is 7 times less toxic than Ronidase.

Daily, for 62 days, skin application by rubbing of microbial hyaluronidase in the amount of 40 mg/kg (80 IU/kg) that exceeds daily therapeutic dose of Ronidase, and 18.6 times exceeds single dose of microbial hyaluronidase recommended for clinical study did not produce any skin changes in the application site or exerted any signs of resorption induced pathology. These results evidence that the microbial hyaluronidase can be recommended for clinical studies in single dose of 300 IU per application. This dose is comparable to therapeutic doses of Ronidase. If there are no allergic reactions or changes in immune status then a single dose up to 3000 IU can be administered.

EXAMPLE 8

Immunological Properties

Hyaluronidase increases tissue permeability and can penetrates into tissues. This increases the risk of allergic reaction induced by this substance, which brings about the necessity to study effects of hyaluronidase-based drugs on immune system. This Example provides data on the comparative study of antigenic and allergenic properties of hyaluronidase of microbial origin (from *Streptomyces actinocidus*) and hyaluronidase obtained from bovine testis (Ronidase) and their effects on the immune system.

Materials and Methods

The microbial hyaluronidase used in the study had specific activity of 2000 IU/g with 13% of protein and 80% of mannite. For comparison preparation of testicular hyaluronidase (Ronidase) was used with specific activity of 350 IU/g and 35% of protein. Experiments were conducted in Chinchilla rabbits (3-3.5 kg), guinea pigs (300-350 g) and mice of Balb/c, CBA, $C_{57}BL$, $F_1(CRA \times C_{57}BL)$ strains (18-20 g).

Antigenic properties were studied by immunoelectrophoresis with hyperimmune rabbit sera. Determination of antibody titer in blood serum of immunized animals was done by immunoprecipitation.

Anaphylactogenic properties of microbial hyaluronidase were studied in guinea pigs. For single tune sensitization drugs were administered once intracardially in doses 8.5 mg/kg (weight equivalent of single therapeutic dose of Ronidase) and 17.5 mg/kg. Provocation injection was done intravenously after 21 days. Ronidase was used or comparison in the same doses as microbial hyaluronidase. Control animals received physiological solution. Each group included 7 animals. Anaphylaxis was scored on 4 point scale. AI was calculated using the following formula:

$$AI = \frac{(a \times 4) + (b \times 3) + (c \times 2) + (d \times 1) + (e \times 0)}{(a + b + c + d + e)}$$

where: a—number of animals that died (anaphylactic shock 4+): h—number of animals with severe shock (3+); c—number of animals with moderate shock (2+); d—number of animals with weak reaction (1+); b—number of animals without reaction.

Active skin anaphylaxis was studied in rabbits, which received application of microbial hyaluronidase in bandages (40 mg/kg for 35 days). In the second group rabbits received application of the same dose of Ronidase. For skin test method of allergometric titration was used. Skin tests were performed three weeks after last application of the drugs. Enzymes (100, 50, 10 ug/ml, 0.1 ml) were administered intradermally. Active skin anaphylaxis was evaluated by intravenous administration of 0.5% Evans blue before intradermal injection of enzyme. Test was considered positive when the zone of reaction had size not less then 5×5 mm and blue staining intensity was not less than 2+. The intensity of skin staining was scored by using 3 point scale. Two indexes were calculated to evaluate skin reaction: index of the reaction presence (IRP) and index of reaction intensity (IRI). IRP was calculated according to the formula:

$$IRP=(a/b-c/d)\times100$$

where: a—number of animals with positive reaction in experimental group; b—overall number of animals in experimental group; c—number of animals with positive reaction in control group; d—overall number of animals days in control group. No less than 5 animals were in each group.

IRI was calculated according to the formula:

$$IRI=((a/b-c/d)/5)\times100$$

where: a—sum of the intensity score (points) of the reaction in experimental group; h—number of animals in experimental group: c—sum of the intensity score (points) of the reaction in control group: d—number of animals in control group.

Reaction of hemagglutination. Mice (strains CBA and $C_{57}BL$ received for 10 days applications of the microbial hyaluronidase (8.5 mg/kg). SE($10^8$ cells) were injected i.p. on day 11 in experimental and control groups. In the following five days animals continued to receive applications of the drugs. Blood was sampled on day 7 and day 14. Levels of antibodies were determined by the reaction of hemagglutination.

To study the effects of the microbial hyaluronidase on the immune responses to other antigens, mice CBA and $C_{57}BL$ received for 10 days applications of enzymes (8.5 mg/kg). On the $11^{th}$ day of experiment animals received intraperitoneal injection of ovalbumin (2 mg/kg). In the following five days animals continued to receive applications of enzymes. Titer of antibodies against ovalbumin was determined by RIH. For preparation of test-antigen Chromium chloride was used as a binding agent.

Determination of antibodies producing cells (APC). Effects of microbial hyaluronidase on the production of antibodies against SE were studied in BaLb/c mice. Enzyme was administered in applications (8.5 mg/kg) for 15 days. SE were administered i.p ($10^8$ cells in 1 ml of saline) five days before the end of the course. On $5^{th}$ day after SE administration number of APC in spleen was counted. Control animals received only SE.

Effects of microbial hyaluronidase on DHS were tested in CBA mice. Enzyme (8.5 mg/kg) was administered in applications for 10 days. Sensitizing dose of SE, (i.p. $10^7$ cells in 0.05 ml of saline) was administered on $11^{th}$ day. During following five days animals continued to receive applications of enzyme. After five days animals received provocation injection of SE ($10^8$ cells in 0.05 ml of saline) into sole of hind paw. Saline was injected into other paw. Local inflammatory reaction was evaluated in 24 hours comparing weight of both paws. Control animals received only injections of SE and saline without applications of enzymes. Reaction index was calculated. Each group included 10 animals.

Inhibition of leucocytes migration was studied. CBA mice which received the microbial hyaluronidase were injected i.p. with CFA (500 ug of BCG in 0.4 ml/mouse). On day $6^{th}$ blood was sampled and reaction of inhibition of leucocyte migration was performed in 5-channels capillaries. Blood lymphocytes were the source MSF while monocytes and granulocytes were migrating cells. Control animals did not receive microbial hyaluronidase. Tuberculin (0.2 ml) was added to blood samples (0.4 ml). Saline was added in control. Final antigene concentration in culture was 10 and 100 ug/ml. Capillaries were sealed, centrifuged for five minutes at 200 g, and placed in thermostat at 37° C. Reaction was read in 24 hours. Migration was measured with micrometric ruler. The index of the migration suppression (IMS) was calculated according to the formula:

$$IMS=100\%-(\text{migration without antigene/migration with antigene})\times100\%.$$

Transplant against host reaction (TAHR). Evaluation of mitostatic and lymphotoxic activity of the microbial hyaluronidase was done by using model of endogenous colony-forming in mice $F_1(CBA\times C_{57}BL)$. For 10 days mice received applications of the enzyme (8.5 mg/kg), control animals received applications of saline. On $12^{th}$ day of the experiment animals were irradiated with x-rays (500 roentgen). Animals continued to receive the hyaluronidase for 7 more days. Animals were randomly assigned to following groups; Group 1—irradiation only, without drug; Group 2—irradiation combined with local application of hyaluronidase; Group 3—irradiation combined with injection of lymphoid cells from parent animals, no drug; Group 4—irradiation combined with injection of lymphoid cells and application of hyaluronidase. Dose of CBA mice lymphocytes, which suppressed colony formation by 50% was $10^6$ cells. After the end of applications mice were euthanazied spleen was dissected, and, after fixation, number of colonies on the surface of spleen in control and experimental groups was counted.

Statistical analysis was done using parametric and non-parametric criteria. Accepted level of significant difference was 0.95.

Results

Immunoelectrophoresis (current 50 mA, 1 hour, veronal buffer pH 8.3, ionic strength 0.05 in 1% agar gel) demonstrated that microbial hyaluronidase was no homogenous substance but contained 3 protein components. Anaphylaxis properties of the microbial hyaluronidase and Ronidase were studied in guinea pigs. The microbial hyaluronidase showed weak allergenic activity, Significance in comparison to Ronidase. n=7 in each group.

In order to compare allergenic potential of the microbial enzyme with other enzymes single minimal sensitizing dose administered intracardially ($5.0$-$5.0\times10^{-3}$ mg protein/kg) was determined, in three weeks, provocation injection (therapeutic dose, i.v.) was made. This dose did not produce toxic reactions in intact animals. All tested doses of microbial hyaluronidase produced relatively weak allergic reactions. Probably, minimal sensitizing dose of the microbial hyaluronidase is beyond limits of doses tested. Allergenic activity of the microbial enzyme did not differ significantly from Ronidase when used in the same weight amount.

Skin sensitizing activity of the microbial hyaluronidase and Ronidase was studied in rabbits, which received multiple skin applications microbial hyaluronidase and Ronidase. Skin reactions in response to intradermal administration of microbial hyaluronidase developed within 0.25-3 hours, and were immediate in character. Size of the skin reaction was relatively large (10×10 mm in diameter with intensity 2+). In animals sensitized with dose of Ronidase equivalent by weight (rather than activity) skin reactions were less expressed. In control in animals, skin reactions were insignificant. It is possible to conclude that multiple local application of microbial hyaluronidase triggers production of antibodies, are fixed in the skin.

Application of test-allergen in all tested concentrations revealed significance differences in reactions of animals of control and experimental groups in IRP and IRE Decrease of dose of test-allergen skin produced weaker skin reactions.

Effects of microbial hyaluronidase and Ronidase did not differ significantly when doses compared were expressed in weight, rather than in IU of activity. Experiments demonstrated that microbial hyaluronidase after multiple local application in doses equivalent (by weight) to similar doses of Ronidase had skin sensitizing activity. In general practice anaphylaxis properties of enzyme preparations observed after parenteral administration allows to characterize allergenic potential of these substances. Allergenic potential of an enzyme exerted after parenteral administration correlates with allergenic potential of it when administered by other was (aerosols, compresses, oral etc.). When compared to allergenic potential of other enzymes used in clinical practice, microbial hyaluronidase has lower minimal sensitizing dose.

Multiple external application of microbial hyaluronidase (8.5 mg/kg) in mice BaLb/c significantly decreased number of antibody producing cells, in spleen compared to control. According to the reaction of local hemolysis number of antibody producing cells in experimental group was 54+10 while in control group, which did not receive microbial hyaluronidase it was 154+39. Immunodepressive activity of microbial hyaluronidase may be due to presence in the preparation of low molecular components or due to its specific activity. Important role in the production of humoral and cell immunity belongs to the macrophages. Microbial hyaluronidase according to the literature significantly suppresses phagocytosis of cellular antigens. It is possible that discovered suppression of immune response toward SE is due to inhibiting effects of microbial hyaluronidase on phagocytosis.

Inhibiting action of microbial hyaluronidase (8.5 mg/kg) on the production of antibody against cellular or water soluble antigens was also observed in the experiments with strongly and weakly reacting strains of mice. As expected, immunosuppressive effects of the microbial hyaluronidase were more pronounced in animals with strong reaction against corpuscular antigens. Statistically significant suppression of immune responses ($p<0.05$) was observed in animals immunized by ovalbumin as well as by SE. However in either case there was no complete suppression of immune response triggered by these antigens. It can be concluded that the microbial hyaluronidase suppresses humoral immune response when applied locally in dose of 8.5 mg/kg.

Experiments were aimed to evaluate affect of the enzyme on some indexes of functional activity of T-lymphocytes. For this purpose delayed-type hypersensitivity (DTHS), suppression of lymphocyte migration, and transplant against host reaction were studied. Multiple external applications of the actinocidus hyaluronidase did not affect local inflammatory reaction as evaluated by DTHS. No significant differences were observed in reaction index (RI) between control and experimental groups (16.6+4.1 and 183+2.7, respectively, $p>0.05$). Local applications of microbial hyaluronidase did not affect spontaneous leucocyte migration (6.49+0.66 in control and 6.54+1.04 in experiment, $p>0.05$). Tuberculin (10 ug/kg) suppressed leucocyte migration by 27% ($p<0.005$) in control group. However, in cell cultures obtained from experimental groups that received microbial hyaluronidase, leucocyte migration was suppressed not more than by 4% ($p>0.05$, compared to control). Migration in control was 4.72+0.53 and in experiment 6.26+0.64 ($p<0.005$). It is possible to conclude that microbial hyaluronidase, when applied locally in dose 8.5 mg/kg, shows immunodepressive action and reverses suppression of leucocyte migration.

Microbial hyaluronidase after multiple local applications in mice, which received sublethal dose of x-ray, significantly suppressed by 55.9% proliferation of stem cells (mitostaic effect), which is comparable to the effect of 6-mercaptopurine. Select lymphotoxic effect of Mile rob al hyaluronidase on T-lymphocytes was insignificant (% of survived CPC was 6.9).

It can be concluded that the microbial hyaluronidase is not a powerful allergen. Multiple local applications of microbial hyaluronidase (8.5 mg/kg) produced inhibiting action on some components of immune response in experimental animals. In model of transplant against host reaction it was observed that microbial hyaluronidase from Streptomyces actinocidus had mitostatic activity in dose, which equivalent by weight to the therapeutic dose of clinically used Ronidase (8.5 mg/kg), During, clinical trials it is necessary to control immune status.

Conclusions

Microbial hyaluronidase in doses equivalent to Ronidase doses (by weight) has weak allergenic activity, which is comparable to other enzyme substances that are recommended for clinical use by Pharmacological Committee of the Ministry of Health of Russian Federation (such as Ronidase, Solizim, Amilase). To reveal sensitization to the preparation skin test can be used. Microbial hyaluronidase being applied locally multiple times in dose of 8.5 mg/kg expresses some immune depressive activity and has mitostatic action.

EXAMPLE 9

Effects of Microbial Hyaluronidase on the Immune Status

The effects of a microbial hyaluronidase from Streptomyces actinocidus and the tissue (bovine testis) hyaluronidase (Ronidase) on the immune status of mice were studied. Drugs were applied externally onto the skin in doses recommended for therapy. The following substances were used in the study: (1) Microbial hyaluronidase produced by Streptomyces bacteria. Enzyme activity was equal 3000 IU/g; amount of the protein 7%; with mannite as a diluent. Daily therapeutic does of microbial hyaluronidase is 1.43 mg/kg (300 IU). (2) Testicular hyaluronidase (Ronidase). Enzyme activity was 300 IU/g. Daily therapeutic dose of the drug is 14.3 mg/kg (300 IU).

Study was conducted in mice (CBAxC57/B1/6)$F_1$ (18-20 grains body weight). Effects of microbial hyaluronidase and Ronidase on the immune status were evaluated by using following parameters: Quantity of antibody producing cells (APC) in the spleen; Quantity of EAC rosette producing cells (RPC) in the spleen; Blood level of hemagglutinating antibodies.

Drugs in therapeutic doses were applied onto the shaved area (1×2 cm) of the skin. First group of mice received daily applications of microbial hyaluronidase (1.43 mg/kg. 300 IU). Second group received Ronidase (14.3 mg/kg. 300 IU). Third group (control) received daily applications of distilled water. Immediately after application mice of experimental and control groups were restrained in individual cages for 4 hours once a day. Substances were applied for 14 days. On the $15^{th}$ day mice were immunized by thymus-dependent corpuscular antigen-sheep erythrocytes (0.5 ml of 5% erythrocyte suspension was administered i.p.). On day 5 the immune response toward sheep erythrocytes. Animals inert euthanized by decapitation. Blood was collected and serum level of hemagglutinating antibodies was determined by standard method. Suspension of spleen cells was prepared. Viable cells were used to determine number of RPC by local hemolysis in agar and number of APC. Student's t-test was used for statistical analysis.

Results obtained did not reveal significant differences between experimental and control groups in overall amount of nuclear cells in the spleen, number of APC, number of immunocompetent cells with surface Ig-receptors toward sheep erythrocytes. In experimental groups the titer of hemagglutinating antibodies was significantly lower than in control. However, titer of hemagglutinating antibodies did no decrease below the low level of the norm for these strain of mice. It can be concluded that neither microbial hyaluronidase nor Ronidase, when applied onto the skin in therapeutic doses affect humoral immune response.

EXAMPLE 10

Study of the General Toxic Properties of the Ointment with Microbial Hyaluronidase and Hydrocortisone The non-specific toxic effects of the hydrocortisone ointment with microbial hyaluronidase were studied. Ointment with the hydrophilic base for external application contained as an active compounds hydrocortisone (17-oxycorticosterone), in form of hydrocortisone acetate (0.5%), and microbial hyaluronidase (20 IU/1 g of ointment).

Therapeutic effect is based on the interaction between hydrocortisone and hyaluronidase. Microbial hyaluronidase increases penetration of hydrocortisone into the tissue, accelerates its therapeutic effect, and decreases treatment dose. At the same time hydrocortisone decreases activity of hyaluronidase, and doesn't allow the inflammatory process to spread. Hydrocortisone provides anti-inflammatory and the anti-allergic action of the drug. Addition of the hyaluronidase allows significantly increase indications for drug usage. Moreover, proprietary hydrophilic base allows to deliver hydrocortisone in watersoluble carrier that significantly increases its bio-availability.

Materials and Methods

Acute toxicity of the ointment was studied in white non-strain male and female rats (n=60) with body weight 180-250 g and mice (18-20 g, n=60). Ointment was studied in the following doses 9000, 13000, 17000, 21000, and 25000 mg/kg of the body weight. Rats and mice were randomly assigned to one of 10 groups, which included 6 males and 6 females each. Ointment was a dissolved in distilled water and administered i.p. in the volume 1-5 ml. Injection of distilled water was used as control. After injection animals were observed for 14 days. Animals appearance, behavior, reactions stimuli, body weight and lethality were noted, and $LD_{50}$ was determined.

General toxicity of the ointment was studied in white non-strain rats. Animals were randomly assigned to one of the three groups 18 rats each. First group received skin application of ointment, second group received only ointment base, and third group served as a control. Ointment and base were applied for 30 days on the undamaged epilated skin of the back on the area 3×4 cm, once a day in the amount off 0.7-1.1 g per animal (4.7 g/kg). The individual dose for each animal was adjusted once a week to take into account body weight. After the end of treatment animals were followed for 14 days. As an integral indexes of possible toxic reaction the following parameters were monitored: changes in the animal appearance and behavior, food and water consumption, excretion, and body weight. ECG was performed in II standard lead. Periodically blood samples were obtained from the tail vein to determine plasma cholinesterase, blood glucose, hemoglobin, and blood cell counts. Local skin irritating action of the ointment was evaluated visually. For that purpose the intensity of erythema and thickness of skin fold were recorded. Every two weeks 6 animals from each group were euthanasied by decapitation for pathological studies. Internal organs were analyzed macro- and microscopically. The fur and Skin area where ointment or ointment base were applied were studied.

Study of the allergenic properties of the ointment was done in male guinea pigs (250-300 g). Animals were randomly assigned to 3 groups 15-18 animals each. One group was control. In two experimental groups animals received daily application of ointment on the epilated area of the skin on the side of the body. Daily areas of ointment application were examined to exclude non-allergic dermatitis. For sensibilization guinea pigs received single maximal dose of 300 mg/kg followed by 10 doses of 30 mg/kg. Evaluation of allergenic activity of the ointment was performed in half of the animals after 10 days and in the second half after 20 days. Solution of the ointment (100 ug in 0.1 ml) was injected intradermally to reveal possible sensibilization on day 10 and 20, respectively. In 24 hours after injection skin reaction was scored.

Results

Acute toxicity. Maximum dose of 25,000 mg/kg of the ointment triggered 100% lethality of rats and mice within first 24 hours, hi mice dose of 21,000 mg/kg triggered 100% lethality within 1-3 days. Within the first 24 hours after administration of highest dose animals quickly went into the side position and seized. Majority of animals that received 17000-21000 mg/kg died within first 3 days. Animals were hypodynamic and entered coma-like state. Animals that survived over two weeks slowly recovered. These animals initially lost weight. By the end of two week period their weight returned to the initial values. However, they gained weight slower than animals in control group. Rats that received drug in dose 9000-13000 mg/kg did not lose weight and were comparable to control group. Macro-examination during autopsy of animals, which died from acute intoxication revealed only increased blood accumulation in liver and spleen. The calculated LD50 for rats was 17340 mg/kg and for mice 16670 mg/kg.

Chronic Toxicity. Animals that received ointment or ointment base did not differ in their appearance or behavior from control animals. Fur was smooth and shiny and without pigmentation. There were no changes in the bowl or urinary excretion. Body weight of the experimental animals that received ointment application was significantly less than body weight of controlled animals starting from the second week of treatment up to the end of first week after it. In two weeks after the end of treatment body weight of experimental and control animals did not differ. On average during six weeks of the experiment ointment treated animals gained 130 grams or 86.6% of their initial body weight; base treated animals gamed 189 grams or 140% of initial body weight, and control animals gained 187 grams or 152% of initial body weight. However, food consumption in animals that received ointment did not differ from other groups. After two weeks in animals that received application of ointment or ointment base the duration of the ECG interval P-Q and Q-T interval increased. By the end of the experiment both intervals normalized. In animals that received only ointment base in the same period of amplitude of peak T slightly decreased, Heart rate in all experimental animals remained within normal limits. Thus daily for four weeks massaging of the ointment (4 g/kg) or ointment base into undamaged skin of the back of the rats did not produce any irreversible changes in heart function. Prolonged application of the ointment (4.7 g/kg) did not produce any significant changes in plasma cholinesterase, blood hemoglobin or blood counts. Blood glucose slightly but significantly decreased in experimental group. Autopsy demonstrated no differences in overall appearance of internal organs. Heart liver, kidneys, spleen, adrenals, pancreas, thymus, brain and testis had normal color, configuration and consistency. The skin and underlying, fat tissue where ointment was applied had regular appearance and consistency.

Local skin irritating effects of the ointment. No signs of skin irritating effects of prolonged application of the ointment or ointment base were observed.

Allergenic effects. Application of the ointment or ointment base continuously for ten or twenty days did not produce dermatitis when applied in therapeutic dose or in a dose ten times higher. Sensibilization to the ointment Or ointment base was not observed during skin application as revealed by the administration of releasing injection. Number of positive reactions to intradermal injection of ointment solution in control group was equal or exceeded the number of reactions in experimental groups.

Conclusions

The factual maximal tolerated lip dose of the ointment was 21000 mg/kg for rats and 17000 mg/kg for mice. Absolutely tolerated i/p dose of the ointment for rats and mice is a 9000 mg/kg. The LD50 of the ointment administered i/p for rats is 17330±3140 mg/kg and for mice—16730±3850 mg/kg. Daily application for 30 days of the ointment into non-damaged skin in the amount of 4.7 g/kg that exceeds a daily therapeutic dose for hyaluronidase for human more than 20 times and the by hydrocortisone more than 40 times does not produce any significant irreversible global or local changes. The ointment when applied to skin does not produce sensibilization or local skin irritation in doses that exceed therapeutic doses by 10-20 times.

EXAMPLE 11

Report on the Results of Clinical Studies

This Example is a compilation of results of several clinical studies. A preparation of a hyaluronidase from *Streptomyces actinocidus* for external use was tested. The preparation was based on the enzyme hyaluronidase (hyaluronate lyase. EC 4.2.2.1) produced by the strain *Streptomyces actinocidus* The medication is distributed in vials containing 300±80 IU of active substance.

Study 1

Microbial hyaluronidase was used for the treatment of limited cutaneous scleroderma. The duration of the disease varied from several months to 15 years. Process was widely spread. Microbial hyaluronidase was applied by electrophoresis directly to plaques. From the fifth day of drug application plaques showed regression. Under continuous application of microbial hyaluronidase complete disappearance of plaques was observed in 17 patients in 11-14 days after the initiation of treatment. In 4 patients effects became obvious in 21 days. In 2 patients effect was insignificant.

Study 2

Microbial hyaluronidase was used in 42 patients belonging to different groups: 10 patients had rheumatoid arthritis and 12 patients suffered from the arthritis of the spine joints, 3 patients had Dupuytren contracture, 14 patients had tendinitis of inflammatory or posttraumatic origin, 2 patients exerted skin plaques due to scleroderma and 1 patient had deforming facial surgical scars. Patients belonged to age groups from 30 to 60 years and duration of pathological condition varied from several months to 10 years. The drug was applied every day by electrophoresis and combined with non-steroid anti-inflammatory drugs.

Positive reaction to treatment was observed in 37 patients. In patients with arthritis the joint movements increased on average by 17.2±1.5 degrees. In patients with Dupuytren contracture nodes and tendons became softer. In sclerodermia patients edema and skin tightness decreased. In patients with tendinitis pain diminished, movement volume increased, inflammatory edema subsided. In patients with lower back pain due to arthritis of the spine joints pain threshold increased. In a patient with the facial scar deformities became significantly softer after only 3 courses of drug application. Overall results were positive. It was specially noted that drug was very effective upon local application and exerted minimum side effects.

Study 3

Microbial hyaluronidase was used in 13 patients with afterburn scars, in 3 patients with scars after mechanical trauma, in 2 patients with the aftersurgery scars and 1 patient with Dupuytren contracture. Duration of the scar existence was from 1 month to 1.5 years. Drug was administered in most cases by application. In 2 patients application was alternated with electrophoresis. Treatment lasted for 15-30 days.

Positive therapeutic effect of different magnitude was observed in all 18 patients. The effects included softening and thinning of scars, increase in joint movements, decrease or complete disappearance of pigmentation and itching. Treatment was most effective against linear and fresh scars and was less effective toward spread and/or kelloid scars. The alternate administration of microbial hyaluronidase by application and electrophoresis was most efficient. Drug was well tolerated. Only in one case allergic rash was observed that disappeared after drug administration was interrupted.

Study 4

Microbial hyaluronidase was tested in 56 patients from 16 to 62 years of age (29 male and 27 female). Forty-two patients had combined damage of the wrist with severe limitation of movements, 14 patients suffered from Dupuytren contracture. In both groups drug was applied by application before surgery to soften tissue and after reconstructive surgery. For each application about 300 IU was used. Single application lasted for 16-18 hours. The course of treatment lasted 15-60 days with a break for 3-4 days every 2 weeks. In patients with contracture and limitation in joint movements treatment with microbial hyaluronidase was combined with physical exercises. In all patients positive effect was obtained. Therapeutic effect was most pronounced in fresh scars of different origin and in early stages of Dupuytren contracture.

Study 5

Microbial hyaluronidase was used in the form of applications for treatments of afterburn scars in 50 patients, post traumatic scars in 30 patients, Dupuytren contracture in 5 patients and joint contracture of burn or posttraumatic origin in 15 patients. Duration of the diseases was from 1 month to 2 years. For single application that lasted 12-16 hours 300 IU of microbial hyaluronidase was used. The course of treatment lasted for 30 days. In patients with contracture and limitation in joint movements treatment with microbial hyaluronidase was combined with physical exercise Positive therapeutic effect was obtained in 100% cases and included in softening of scars, decrease in pain syndrome, increase in movements, decrease or prevention of contracture formation. In 5 patients after 15-20 application local inflammatory reaction occurred with skin hyperemia that disappeared after short break in treatment.

In the second group (15 patients) microbial hyaluronidase was applied by using electrophoresis in patients with afterburn hypertrophic and kelloid scars 1-12 month old. Therapeutic dose was 300 IU for session and course included 10-20 sessions. In all patients damaged area became less irritated, pain, edema and itching decreased, increase in movements of scar tissue softened. Side effects were not observed. High effectiveness of the drug administered by electrophoresis was observed.

Study 6

Studies were carried out in 50 patients 16-45 years of age suffering from keloid scars (19 patients), hypertrophic (21 patient) and atrophic (10 patients) scars. Course of treatment included local electrophoresis for 20 min of the drug (300 IU) for 15 days. Positive therapeutic effects in most cases was observed after fifth session. Effect included decrease or disappearance in burning sensations, itching, and pain. Scars became pale, soft, painless under palpation and thinner. After the full course area of kelloid scars decreased by 40%. In patients with hypertrophic scars effect was more pronounced: scars became thinner and did not elevate longer above level of normal skin. The treatment of the cases of hypertrophic scars that did not disappear was easily finalized by using dermabrasion or CO-laser therapy. Side effects were not observed.

Study 7

Microbial hyaluronidase was used in 10 patients (2.5-59 years of age) with scars of different origin (burn, surgery etc.) that were 10 days to 1 year old. Drug was administered in application for 12-16 hours every day. Total duration of the treatment was 40-60 days. Effects of microbial hyaluronidase were observed in 9 patients and included thinning of the scar, decrease in pain, itching, inflammation and increase in movement amplitude. In early application (10-14 days after the surgery) effect was obvious in 1-2 days, more delayed application after 10-15 sessions. In 2 patients after treatment with applications for 2 month every day some local dermatitis was observed that disappeared after ending of treatment.

In summarize, the effectiveness of microbial hyaluronidase was studied in 264 patients 2.5-63 years of age. The majority were patients with scars of different origin (after burn, posttraumatic after surgery etc.) limitation on joint movements of different origin. (osteochondritis, rheumatoid arthritis etc.) and Dupuytren's contracture. Duration of disease was from 10 days to 15 years. Drug was administered in applications or by electrophoresis. Applications were applied daily for 12-18 hours for 10-60 days. In some cases weekly short break for 2-3 days was made. Duration of the electrophoresis course was 10-21 daily sessions. Therapeutic dosage on average was 300 IU for single session. Microbial hyaluronidase was combined with non-steroid anti-inflammatory drugs and other treatments. The results of the clinical trials demonstrated effectiveness in 95% (256 out of 264 patients). Effect of microbial hyaluronidase included decreased edema, pigmentation, itching, pain syndrome, softening and thinning of scars, increase in movements and prevention or decrease of contracture. It was noted that the therapeutic efficacy was highest when drug was applied in early stagers of the disease when reparative processes are still active. However, a good effect was also obtained in patients with keloid sears, observed already after fifth sessions. After treatment area of keloid scars decreased by 40%. The drug was also well tolerated. Side effects included skin hyperemia and rash. Either of side effects disappeared completely in 2-3 days after temporal interruption of drug administration and observed only in 2.6% in 7 out of 264 patients). The studies showed the high efficiency and safety of the microbial hyaluronidase, and its wide spectrum and advantages over Ronidase.

Treatment of Chronic Inflammatory Disease of Female Reproductive Organs

Study 1

Microbial hyaluronidase was studied in 57 patients. The first group of patients (60.9%) consisted of patients with chronic inflammatory diseases of female reproductive organs: adnexitits salpingitis, oophoritis, cervicitis, endocervicitis colpitis etc.), second group (25.0%) consisted of patients with benign tumors (Incline myoms, ovarian cysts, endometric polip etc.). Third group consisted of patients with scar deformations of cervix and vagina. (atresia of cervical canal, scar deformation of cervix or vagina, muscle insufficiency of pelvic bottom). Patients were 18 to 45 years of age and disease duration varied from 6 month to 6 years.

Microbial hyaluronidase was applied daily in form of vaginal tampons or by electrophoresis. In patients with vaginal stricture or after surgery microbial hyaluronidase solution was applied intra vaginal through catheter. In 18 patients drug was used before surgery in 8 patients after surgery and in 31 patients before and after surgery. Single dose was 300+60 IU. Duration of treatment was 6-15 days. Estimation of effectiveness of the drug included subjective complaints, results of bimanual study, laboratory data (biochemistry, hematological, microbiological, immunological etc.) and instrumental studies (laparoscopy, chormohydrotubation, colposcopy, ultrasound etc.).

Based on the results of the dynamic of the disease positive therapeutic effect was observed in 90.2-100% patients. Effect included: disappearance of low-abdominal pain (100%), restoration of active sexual life (100%), disappearance of pain during bimanual investigation (90.6%), restoration of menstrual function (100%), increase in vaginal secretion (90.2%). In patients received Microbial hyaluronidase before surgery in 4-7 days after onset of treatment vaginal secretion became liquid, clear, vaginal volume increased due to increased wall elasticity, mucous became more normotrophic. Studies of vaginal secretion demonstrated that by 3-5 day of the drug application vaginal pH changed form acidic to neutral that also was important for decrease of painful sensations and restoration of normal sexual life. In some patients, administration of microbial hyaluronidase led not only to decrease of amount of conditional pathogenic microflora in vagina (enterococci decreased by 75.9%, staphilococcus by 54.1%, candid—by 50%) but also completely eliminated it in 16.7% cases that indicate bactericide action of the drug. Analysis also indicates positive action of microbial hyaluronidase on the reparative processes in the period after surgery on abdominal wounds as well as vaginal wounds. Administration of microbial hyaluronidase decreased inflammatory reaction and tissue edema accelerates wound healing with subsequent development of soft and small scar and decreased by 23%. Administration of microbial hyaluronidase from the first day after surgery allowed to decrease aftersurgery hospitalization period by 12%. Both ways of drug, administration were equally effective.

Along with good tolerance was noted and lack of side effect. In spite of large percentage of previous allergic reactions among patients only in one patient (1.7%) unpleasant sensations appeared in vagina, itching and burning that completely disappeared soon after administration was disrupted. Based on the data showing, high effectiveness of microbial hyaluronidase and good tolerance drug was recommended by the Hospital for clinical use in gynecology as part of therapeutic complex therapy.

Study 2

Microbial hyaluronidase was administered in 50 patients 19 to 68 years of ages. First group (38 patients) consisted of female with chronic adnixitis. In 18 of them it was combined with colpitis, endocervocitis and parametritis. Second group (12 patients) consisted of female after different reconstructive-plastic surgical interventions in which microbial hyaluronidase was used to prevent development of scar deformations starting form the $3^{rd}$ postoperative day. Drug was administered in vaginal tampons for 10 days or by electrophoresis for 14 days. Single dose was 300+60 IU. In both groups administration of microbial hyaluronidase was combined with standard antibacterial, anti-inflammatory, desintoxicating and symptomatic therapy.

Using objective observations, laboratory data and results of bimanual investigation made evaluation of clinical effectiveness. Therapeutic effectiveness of microbial hyaluronidase in the first group (chronic adnixitis) was 100%. In 75% of patients positive effect was obvious by the end of the first week of treatment Clinical effect included disappearance of pain syndrome, significant decrease in inflammatory changes in parametrium, painless palpation, increase of movability of uterine corpus and cervix. Decrease in leukocytes and erythrocyte sedimentation rate. In the second group of patients, administration of microbial hyaluronidase decreased pain syndrome in the area of surgery due to decrease in after surgery edema of vagina and cervix. By the end of the first week due to microbial hyaluronidase administration tissue in the area of the scar softened and by the end of the second week elasticity of the tissue in the scar area increased significantly that provided good cosmetic effect especially in patients after reconstructive-plastic surgery.

Hospital indicates high therapeutic effectiveness of microbial hyaluronidase for the treatment of chronic inflammatory diseases and prophylactic of scar deformation after reconstructive-plastic surgery in female reproductive organs. No local side effects on vaginal mucous, abdominal wall, cervix were observed. Hospital noted good tolerance, lack of side effects and easiness of administration. Microbial hyaluronidase was recommended for clinical use in gynecology as part of standard complex therapy.

To summarize, microbial hyaluronidase was studied in gynecological practice in 107 patients 18 to 68 years of age. Drug was used mostly to prevent scar deformation after different types of reconstructive-plastic or other surgery and treatment of chronic inflammatory diseases (colpitis, cervicitism endocervitis, adnixit, oophoritis etc.) Microbial hyaluronidase was administered in dose of 300+60 IU every day as vaginal tampons or electrophoresis. Duration of the course was 6-15 days (Table 2), Microbial hyaluronidase was combined with standard anti-inflammatory, antimicrobial, desintoxication and symptomatic therapy. Analysis of the results of clinical studies indicates high therapeutic effectiveness observed in all 107 patients and by separate symptoms 90.2-100% cases. Effect of microbial hyaluronidase was obvious in 4-7 days and expressed in decrease or disappearance of pain syndrome. Significant decrease of inflammatory reaction in the area of pathological source, painless palpation, increase in uterine moveability, vaginal secretion became liquid and clear, elasticity of vaginal walls increased and volume of vagina increased, pH increased from very low to neutral. Menstrual function restored as well as sexual life, leukocytosis decreased and erythrocyte sedimentation decreased.

As studies demonstrated microbial hyaluronidase had regulatory effects on phagocytes of vagina and abdominal cavity by restoring and activating oxygen-dependent function of phagocytes. Microbial hyaluronidase also exerted antimicrobial action decreasing vaginal conditional pathogenic microflora (enterococc, *staphylococcus*, candid). Moreover, administration of the microbial hyaluronidase before and after surgery was beneficial for reparative processes in aftersurgery period in abdominal or vaginal wounds. Administration of microbial hyaluronidase decreased edema, tissue inflammation, intensity of pain syndrome, increase in elasticity in the area of wound that accelerated its healing, and made following scar more thin and tender, decrease by 23% and decreased period of after-surgery hospitalization by 12%. Both was of administration of microbial hyaluronidase (application in tampons or electrophoresis) were equally effective. Good tolerance and practical lack of side effects (0.93%-1 patient out of 107 patients) and convenience of administration were noted.

EXAMPLE 12

Determination of the *Streptomyces actinocidus* Hyaluronidase Sequence

A 449 by gene fragment (SEQ ID NO:3) of the *Streptomyces actinocidus* hyaluronidase gene was cloned, isolated and sequenced according to the following procedure.

A protein sequence was back translated into its nucleotide sequence and used to design degenerate PCR primers for the amplification of the *Streptomyces actinocidus* hyaluronidase gene. Primer sequences are provided below.

```
Forward Primer    GGCGAGTACACSCTCTACACSWSSCCSGCSCAG
                  TTCTA

Reverse primer 1  GTGSATCTCSWWCTCCTCSGGSGTGTCGCC

Reverse primer 2  SATSATSGCSSWSGGSGCGCCSGCSGCSGCSACS
                  AC

Reverse primer 3  GAASATGCCCTGSGCSGCSGTGCC

Reverse primer 4  CTTSACSACGCCGTCSGTSGCSGTSACGAA
```

Template genomic DNA was prepped from a fresh growth of bacteria containing plasmids expressing *Streptomyces actinocidus* genomic DNA sequences. PCR was performed using low annealing temperatures to ensure maximum coverage and hybridization of the reverse primer sequences. PCR amplicons using the degenerate primers generated sequences from 300-450 bases in length Note that W=A or T and S=G or C, in terms of nucleic acid identity.

A 449 base segment was produced with the forward primer and reverse primer 2. The translated protein sequence (SEQ ID NO:4) was found to be homologous with a *Streptococcus pyrogenes* hyaluronidase encoded by a phage. The protein and nucleic acid sequences are given in FIG. 15.

The degenerate PCR amplicons were randomly cloned and 18 positive clones sequenced. Fourteen of these clones aligned with each other and contained both forward and reverse pr mer sequences. When the DNA sequence was translated into protein, several other experimentally determined protein stretches matched up with the translated sequence. In addition, the protein translation aligned with homology to bacteriophage hyaluronidases in the database.

The 449 base sequence encoded a portion of a single open reading frame and its amino acid sequence is given at SEQ, ID NO: 4. The open reading frame did not exhibit either an in-frame start or stop codon, implying that there was gene sequence extending (upstream and downstream) beyond the "known" 449 bases. In addition, the proem data supported the existence of a larger gene.

\* \* \*

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application and in the appended bibliography, the disclosures of which are incorporated herein by reference in their entireties for all purposes.

What is claimed is:

1. An isolated hyaluronidase protein comprising an amino acid sequence as set forth in SEQ ID NO:1, SEQ ID NO:2 or SEQ ID NO:4.

2. The isolated hyaluronidase protein of claim 1, comprising the amino acid sequence of at least one of SEQ ID NO:1, SEQ ID NO:2 and SEQ ID NO:4.

3. The isolated sequence of claim 1, comprising a full-length hyaluronidase from S. actinocidus 77.

4. A pharmaceutical formulation comprising the isolated hyaluronidase of claim 1 and a pharmaceutically acceptable excipient, carrier, diluent, or auxiliary agent.

5. The pharmaceutical formulation of claim 4, wherein the excipient is mannitol.

6. A transdermal delivery article comprising the pharmaceutical formulation of claim 4.

* * * * *